(12) United States Patent
Howard

(10) Patent No.: US 11,950,924 B2
(45) Date of Patent: *Apr. 9, 2024

(54) FUNDAMENTAL CODE UNIT OF THE BRAIN: PHOTORECEPTOR PROTEIN-MEDIATED PHOTONIC SIGNALING WITHIN NEURAL TISSUE AND ITS USES IN BRAIN CO-PROCESSOR

(71) Applicant: Newton Howard, Providence, RI (US)

(72) Inventor: Newton Howard, Providence, RI (US)

( * ) Notice: Subject to any disclaimer, the term of this patent is extended or adjusted under 35 U.S.C. 154(b) by 334 days.

This patent is subject to a terminal disclaimer.

(21) Appl. No.: 16/847,625

(22) Filed: Apr. 13, 2020

(65) Prior Publication Data
US 2020/0237299 A1    Jul. 30, 2020

Related U.S. Application Data

(63) Continuation of application No. 15/988,292, filed on May 24, 2018, now Pat. No. 10,617,348.
(Continued)

(51) Int. Cl.
*A61B 5/00* (2006.01)
*A61B 5/055* (2006.01)
(Continued)

(52) U.S. Cl.
CPC ............ *A61B 5/4839* (2013.01); *A61B 5/055* (2013.01); *A61B 5/112* (2013.01); *A61B 5/24* (2021.01);
(Continued)

(58) Field of Classification Search
CPC .............................. A61B 5/4839; A61B 5/369
(Continued)

(56) References Cited

U.S. PATENT DOCUMENTS 4,362,164 A    12/1982 Little et al.
4,644,959 A    2/1987 Calmonovici
(Continued)

FOREIGN PATENT DOCUMENTS

WO    2015008154 A2    1/2015
WO    2017040741 A1    3/2017
(Continued)

OTHER PUBLICATIONS

Non-final Office Action dated Apr. 18, 2013 issued in U.S. Appl. No. 12/880,042.
(Continued)

*Primary Examiner* — Nicole F Lavert
(74) *Attorney, Agent, or Firm* — Michael A. Schwartz

(57) ABSTRACT

Embodiments of the present systems and methods may relate to a non-invasive system with diagnostic and treatment capacities that use a unified code that is intrinsic to physiological brain function. For example, in an embodiment, a computer-implemented method for affecting living neural tissue may comprise receiving at least one signal from at least one read modality, the signal representing release of photons from mitochondria of the living neural tissue, computing at least one signal to effect alterations to the living neural tissue based on the received input signal, the computed signal adapted to cause transmission of photons to the living neural tissue, and delivering the photons to the living neural tissue to effect alterations to the living tissue.

18 Claims, 32 Drawing Sheets

Related U.S. Application Data

(60) Provisional application No. 62/510,519, filed on May 24, 2017.

(51) Int. Cl.

| | | |
|---|---|---|
| *A61B 5/11* | (2006.01) | |
| *A61B 5/24* | (2021.01) | |
| *A61B 5/245* | (2021.01) | |
| *A61B 5/30* | (2021.01) | |
| *A61B 5/369* | (2021.01) | |
| *A61M 21/02* | (2006.01) | |
| *A61N 1/00* | (2006.01) | |
| *A61N 2/00* | (2006.01) | |
| *A61N 5/06* | (2006.01) | |
| *A61M 21/00* | (2006.01) | |
| *A61N 1/05* | (2006.01) | |
| *A61N 1/36* | (2006.01) | |
| *A61N 5/10* | (2006.01) | |
| *A61N 7/00* | (2006.01) | |

(52) U.S. Cl.
CPC .............. *A61B 5/245* (2021.01); *A61B 5/30* (2021.01); *A61B 5/369* (2021.01); *A61B 5/407* (2013.01); *A61B 5/4082* (2013.01); *A61B 5/4088* (2013.01); *A61B 5/4803* (2013.01); *A61B 5/4824* (2013.01); *A61B 5/7282* (2013.01); *A61M 21/02* (2013.01); *A61N 1/00* (2013.01); *A61N 2/006* (2013.01); *A61N 5/0618* (2013.01); *A61N 5/0622* (2013.01); *A61B 5/4076* (2013.01); *A61B 2576/026* (2013.01); *A61M 2021/0027* (2013.01); *A61M 2021/0044* (2013.01); *A61N 1/0534* (2013.01); *A61N 1/36014* (2013.01); *A61N 1/36071* (2013.01); *A61N 2005/0661* (2013.01); *A61N 2005/1087* (2013.01); *A61N 2007/0026* (2013.01)

(58) Field of Classification Search
USPC .......................................................... 607/88
See application file for complete search history.

(56) References Cited

U.S. PATENT DOCUMENTS

| | | | |
|---|---|---|---|
| 6,159,015 | A | 12/2000 | Buffington et al. |
| 6,338,628 | B1 | 1/2002 | Smith |
| 7,346,174 | B1 | 3/2008 | Smith |
| 7,648,498 | B2 | 1/2010 | Hempel |
| 8,535,361 | B2 | 9/2013 | Lim et al. |
| 2002/0072686 | A1 | 6/2002 | Hoey et al. |
| 2002/0111777 | A1 | 8/2002 | David |
| 2003/0040080 | A1* | 2/2003 | Miesenbock .... C07K 14/43581 435/69.1 |
| 2003/0195584 | A1 | 10/2003 | Dawson |
| 2004/0019370 | A1 | 1/2004 | Gliner et al. |
| 2004/0186719 | A1 | 9/2004 | Polanyi et al. |
| 2004/0220487 | A1 | 11/2004 | Vyshedskiy et al. |
| 2005/0118558 | A1 | 6/2005 | Wallis et al. |
| 2005/0142524 | A1 | 6/2005 | Simon et al. |
| 2005/0250082 | A1 | 11/2005 | Baldwin et al. |
| 2006/0004279 | A1* | 1/2006 | Ikeda ..................... A61B 6/507 600/411 |
| 2006/0095251 | A1 | 5/2006 | Shaw |
| 2006/0212097 | A1 | 9/2006 | Varadan et al. |
| 2007/0117073 | A1 | 5/2007 | Walker et al. |
| 2007/0225674 | A1 | 9/2007 | Molnar et al. |
| 2008/0091089 | A1 | 4/2008 | Guillory et al. |
| 2008/0146890 | A1 | 6/2008 | LeBoeuf et al. |
| 2008/0183226 | A1 | 7/2008 | Buras et al. |
| 2008/0232604 | A1 | 9/2008 | Dufresne et al. |
| 2009/0157389 | A1 | 6/2009 | Shaw |
| 2011/0015538 | A1 | 1/2011 | Matthews, Jr. |
| 2011/0027765 | A1 | 2/2011 | Nader |
| 2011/0190665 | A1 | 8/2011 | Bedingham et al. |
| 2012/0219934 | A1 | 8/2012 | Nakane et al. |
| 2012/0221075 | A1 | 8/2012 | Bentwich |
| 2013/0116584 | A1 | 5/2013 | Kapoor |
| 2013/0338526 | A1* | 12/2013 | Howard ............... A61N 5/0618 607/3 |
| 2014/0358199 | A1 | 12/2014 | Lim |
| 2015/0164340 | A1 | 6/2015 | Bedingham et al. |
| 2015/0313496 | A1 | 11/2015 | Connor |
| 2016/0262717 | A1 | 9/2016 | Smith |
| 2017/0027812 | A1 | 2/2017 | Hyde |
| 2017/0065229 | A1 | 3/2017 | Howard |
| 2017/0231597 | A1 | 8/2017 | Howard |
| 2017/0251985 | A1 | 9/2017 | Howard |
| 2017/0258389 | A1 | 9/2017 | Howard |
| 2017/0258390 | A1 | 9/2017 | Howard |
| 2018/0028144 | A1 | 2/2018 | Chen et al. |
| 2018/0093092 | A1 | 4/2018 | Howard |
| 2018/0256917 | A9 | 9/2018 | Lim |
| 2018/0289318 | A1 | 10/2018 | Howard |
| 2018/0333587 | A1 | 11/2018 | Howard |
| 2018/0338715 | A1 | 11/2018 | Howard |

FOREIGN PATENT DOCUMENTS

| | | |
|---|---|---|
| WO | 2017115368 A1 | 7/2017 |
| WO | 2017190049 A1 | 11/2017 |

OTHER PUBLICATIONS

Response filed Oct. 18, 2013 in U.S. Appl. No. 12/880,042.
Final Office Action dated Jan. 30, 2014 issued in U.S. Appl. No. 12/880,042.
Amendment filed Jul. 30, 2014 in U.S. Appl. No. 12/880,042.
Non-final Office Action dated Sep. 10, 2014 issued in U.S. Appl. No. 12/880,042.
Amendment filed Feb. 10, 2015 in U.S. Appl. No. 12/880,042.
Final Office Action dated Jun. 4, 2015 issued in U.S. Appl. No. 12/880,042.
Amendment filed Dec. 3, 2015 in U.S. Appl. No. 12/880,042.
Non-final Office Action dated Jan. 15, 2016 issued in U.S. Appl. No. 12/880,042.
Amendment filed Jul. 15, 2016 in U.S. Appl. No. 12/880,042.
Final Office Action dated Nov. 1, 2016 issued in U.S. Appl. No. 12/880,042.
Amendment filed May 1, 2017 in U.S. Appl. No. 12/880,042.
Non-final Office Action dated Sep. 22, 2017 issued in U.S. Appl. No. 12/880,042.
Final Office Action dated Jul. 5, 2018 issued in U.S. Appl. No. 12/880,042.
Amendment filed Mar. 20, 2018 in U.S. Appl. No. 15/219,255.
Notice of Allowance dated Jun. 20, 2018 issued in U.S. Appl. No. 15/219,255.
Notice of Allowance dated Sep. 19, 2018 issued in U.S. Appl. No. 15/219,255.
Notice of Allowance dated Mar. 20, 2019 issued in U.S. Appl. No. 15/988,292.
Notice of Allowance dated Apr. 23, 2019 issued in U.S. Appl. No. 15/988,292.
Notice of Allowance dated Jul. 18, 2019 issued in U.S. Appl. No. 15/988,292.
Non-final Office Action dated Mar. 29, 2019 issued in U.S. Appl. No. 12/880,042.
Restriction Requirement dated Jan. 31, 2014 issued in U.S. Appl. No. 13/747,448.
Non-final Office Action dated Sep. 21, 2020 issued in U.S. Appl. No. 12/880,042.
Final Office Action dated Dec. 19, 2019 issued in U.S. Appl. No. 12/880,042.
Amendment filed Nov. 5, 2018 in U.S. Appl. No. 12/880,042.
Notice of Abandonment dated Apr. 9, 2021 issued in U.S. Appl. No. 12/880,042.

(56) References Cited

OTHER PUBLICATIONS

Amendment filed Jun. 17, 2020 in U.S. Appl. No. 12/880,042.
Amendment filed Sep. 25, 2019 in U.S. Appl. No. 12/880,042.
Notice of Allowance dated Jun. 1, 2023 received in U.S. Appl. No. 16/841,515.
Final Rejection dated Jan. 5, 2023 received in U.S. Appl. No. 16/841,515.
Response to Non-Final Rejection dated May 16, 2022 received in U.S. Appl. No. 16/841,515, filed Oct. 17, 2022.
Non-Final Rejection dated May 16, 2022 received in U.S. Appl. No. 16/841,515.
Response to Non-Final Rejection dated Jan. 3, 2022 received in U.S. Appl. No. 16/841,515, filed Apr. 4, 2022.
Non-Final Rejection dated Jan. 3, 2022 received in U.S. Appl. No. 16/841,515.
Response to Final Rejection dated Jan. 5, 2023 received in U.S. Appl. No. 16/841,515, filed May 2, 2023.
Response to Final Office Action dated Jun. 19, 2019, filed Oct. 21, 2019 in U.S. Appl. No. 15/431,221.
Final Office Action dated Jun. 19, 2019 in U.S. Appl. No. 15/431,221.
Response to Non-final Office Action dated Oct. 1, 2018, filed Jan. 29, 2019 in U.S. Appl. No. 15/431,221.
Non-final Office Action dated Oct. 1, 2018 in U.S. Appl. No. 15/431,221.
Final Office Action dated Mar. 28, 2019 in U.S. Appl. No. 15/431,283.
Response to Non-final Office Action dated Jul. 6, 2018, filed Dec. 20, 2018 in U.S. Appl. No. 15/431,283.
Non-final Office Action dated Jul. 6, 2018 in U.S. Appl. No. 15/431,283.
Final Office Action dated Jun. 14, 2019 in U.S. Appl. No. 15/431,550.
Response to Non-final Office Action dated Oct. 2, 2018, filed Feb. 28, 2018 in U.S. Appl. No. 15/431,550.
Non-final Office Action dated Oct. 2, 2018 in U.S. Appl. No. 15/431,550.
Response to Non-final Office Action dated Feb. 25, 2019, filed Jul. 24, 2019 in U.S. Appl. No. 15/458,179.
Non-final Office Action dated Feb. 25, 2019 in U.S. Appl. No. 15/458,179.
Final Office Action dated Jun. 27, 2019 in U.S. Appl. No. 15/257,019.
Response to Non-final Office Action dated Nov. 29, 2018, filed May 29, 2019 in U.S. Appl. No. 15/257,019.
Non-final Office Action dated Nov. 29, 2018 in U.S. Appl. No. 15/257,019.
Restriction Requirement dated May 17, 2018 issued in U.S. Appl. No. 15/257,019.
Response to Non-final Office Action dated Mar. 29, 2019, filed Sep. 25, 2019 in U.S. Appl. No. 12/880,042.
Response to Final Office Action dated Jul. 5, 2018, filed Nov. 5, 2018 in U.S. Appl. No. 12/880,042.
Non-final Office Action dated Sep. 22, 2017 in U.S. Appl. No. 12/880,042.

* cited by examiner

| Element | Atomic# | 1st ion. energy, kJ/Mole | 2nd ion, energy, kJ/Mole | 3rd ion, energy, kJ/Mole |
|---------|---------|--------------------------|--------------------------|--------------------------|
| H  | 1  | 1312   | Nil    | Nil    |
| C  | 6  | 1086.4 | 2352.6 | 4620.4 |
| N  | 7  | 1402.3 | 2856   | 4578   |
| O  | 8  | 1313.9 | 3388.2 | 5300.3 |
| Na | 11 | 495.8  | 4562.4 | 6912.2 |
| Al | 13 | 577.6  | 1816.6 | 2744.7 |
| Si | 14 | 786.4  | 1577   | 3231.5 |
| P  | 15 | 1011.7 | 1903   | 2911.9 |
| S  | 16 | 999.6  | 2251   | 3360.6 |
| K  | 19 | 418.8  | 3051.3 | 4411.3 |
| Cr | 24 | 652.8  | 1592   | 2987.2 |
| Fe | 26 | 759.3  | 1561   | 2957   |
| Ni | 28 | 736.7  | 1752.9 | 3393.4 |
| Cu | 29 | 745.4  | 1957.9 | 3553.3 |
| Zn | 30 | 906.4  | 1733.2 | 3832.6 |
| As | 33 | 946.5  | 1797.8 | 2797.4 |
| Se | 34 | 940.9  | 2044.5 | 2973.7 |
| Cd | 48 | 867.7  | 1631.4 | 3616.2 |
| I  | 53 | 1008.4 | 1845.8 | 3184   |
| Pb | 82 | 715.6  | 1450   | 3082   |

Chemical action potentials, by orbital

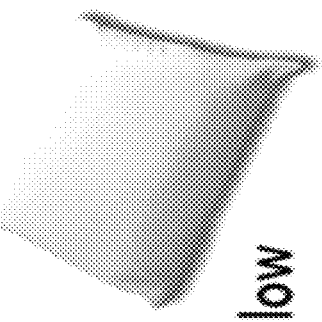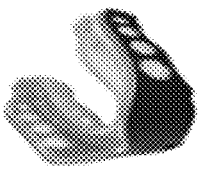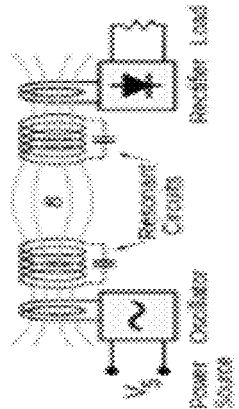
FIG. 22

| Laser Advantages | Laser Disadvantages |
|---|---|
| ● Narrow spectral linewidth of 0.1 nm or better means that there is no chance of cross-talk and no need for additional filtering.<br>● Directional output results in high coupling efficiency in the range of 85-90%. Allows for additional optical components in the beam path.<br>● If not using fiber optics for beam delivery, it is easy to direct high intensity light to the target site in free space.<br>● Best choice when high intensity or wavelength specificity is required | ● Laser modules are more bulky than LEDs and cannot be mounted directly to a subject animal.<br>● Instability in the pulse shape when directly modulating sometimes necessitates an external modulator.<br>● Size of hardware and connectors |
| LED Advantages | LED Disadvantages |
| ● Can be directly modulated at high speed with little degradation in pulse shape.<br>● Very small and light, can be mounted directly on an animal's head for direct stimulation.<br>● Specifications for stability and optical noise are inherently low<br>● Small size required for extremely high density probe. | ● LEDs output in all directions, so it is much harder to couple high power levels into optical fiber. 20-30 mW is a typical maximum throughput for a multi-Watt blue LED coupled to optical fiber. This figure is even lower for green and yellow LEDs.<br>● Wide spectral linewidth of 10-30 nm makes it harder to eliminate cross-talk.<br>● Additional filters may be required to remove unwanted wavelengths, but these will reduce the total power even further. |

FIG. 23

| CNT Advantages | CNT Disadvantages |
|---|---|
| • Electrical conductor/optical fiber dual functionality.<br>• Small size required for extremely high density probe.<br>• Excellent conducting properties<br>• CNT are nanoscale, strong, tough, flexible, biocompatible and non-faradaic while also having both high electrical conductivity and high surface area (Bareket-Keren, L. & Hanein, Y., 2012; Bareket-Keren, L. & Hanein, Y., 2014a; Kotov, N.A. et al., 2009; Voge, C.M. & Stegemann, J.P., 2011).<br>• CNT can allow for the use of smaller electrodes by reducing impedance, thus improving signal-to-noise ratios (Minnikanti, S. & Peixoto, N., 2011). | • Fragile and potentially difficult to handle in a clinical setting<br>• Probe density doesn't have to be a problem (see Lind, G. et al., 2012 for example ), but needs to be addressed<br>• There may be harmful effects of CNT. Most nanotube solutions contain metal catalysts involved in their manufacture that are not removed by the purification process. Some of these, such as yttrium, are known to inhibit the function of ion channels in brain cells (Smith, K., 2008).<br>• We've seen nanorods being phagocytized and carried off by monocytes and suspect this is size-rather than material-dependent. Mention this, ?http://www.ncbi.nlm.nih.gov/pubmed/19845389<br>• It's possible that a lot of the benefit of CNT could be lost to tissue reactions within 50 μm from the implant. |
| Free-floating implant Advantages | Free-floating implant Disadvantages |
| • Reduced astroglial scarring and foreign body response.<br>• No transcranial or transdermal wiring prone to malfunctioning and infection. | • Power supply made more difficult.<br>• Explantation procedures in case of negative effects on patient possibly made more difficult. |

*FIG. 24*

FUNDAMENTAL CODE UNIT OF THE BRAIN: PHOTORECEPTOR PROTEIN-MEDIATED PHOTONIC SIGNALING WITHIN NEURAL TISSUE AND ITS USES IN BRAIN CO-PROCESSOR

CROSS-REFERENCE TO RELATED APPLICATIONS

This application is a continuation of U.S. patent application Ser. No. 15/988,292, filed May 25, 2018, now U.S. Pat. No. 10,617,348, issued Apr. 14, 2020, which claims the benefit of U.S. Provisional Application No. 62/510,519, filed May 24, 2017, the contents of all of which are incorporated by reference herein in their entirety.

BACKGROUND

The present systems and methods relate to devices, methods, and systems for detecting disorders of, and positively affecting the functioning of living tissues such as the brain and spinal cord.

The successful development of new clinical concepts and interventions for neurological diseases of the brain require, first and foremost, a strong theoretical framework for understanding healthy brain function and the brain's capacity for intelligent action. Unfortunately, attempts to understand and explain brain function and dysfunction have been fragmented into several narrow fields of study. In order to study brain function, some researchers (for example, see www.alleninstitute.org) have attempted to reverse-engineer neuronal networks and even the brain itself. This approach was based on the assumption that neurons in-vivo acted just like simple transistors in-silico. Unfortunately, both network and whole-brain modeling have led to very little insight into actual brain function. This is largely because transistor-based computing reacts to static events whilst neurons can react to processes. In contrast to transistors, neurons can establish and change their connections and vary their signaling properties according to a variety of rules, allowing them to adapt to circumstances, self-assemble, auto-calibrate and store information by changing their properties according to experience (Laughlin & Sejnowski, 2003). Consequently, a detailed understanding of neuronal function and network organization is required prior to neuronal network modeling attempts.

Block (1962) describes the "perceptron," or a series of sensory and associator units connected to resemble sensory and analytical components into a machine that vaguely models human response to sensory stimuli. Stimuli of a certain threshold trigger activity in specific associator units, which then activate those to which they are directly connected. Thus, different types of stimuli activate different networks of associator components. In this sense, Block's perceptron approach to modeling brain function privileges the connections between components rather than the components themselves as the primarily important in decoding human thought (Block 1962). However, there still remains the question of what constitutes a basic unit of connectivity. Does a single connection between two associates constitute a fundamental unit of perceptron "thought?" Studying the structure and function of different types of neural connections promises significant contributions, but this still doesn't answer the question of whether these connections constitute a "thought".

Lamb (2010) introduces the concept of the functional web, in which he posits that cognitive concepts such as single words and ideas (analogous to semantic primitives) are in fact spatially distributed across parts of the brain such as the cerebral cortex. Lamb splits these concepts into conceptual, motor, phonological image, tactile, and visual components, or components that roughly align with the senses. This approach not only applies to cognition but also to the concepts that comprise it, and is intuitive since its criteria are empirically grounded. In addition, it unifies behavioral and linguistic activity with neurological activity. Lamb's approach is more focused on response and activation, but the nature of cognition is such that thought can beget more thought; an external agent is not consistently necessary. Tying cognition not just to specific sensory activity but also to brain activity in itself is also a requirement for successful modeling.

Blais et al. (2000) argue that modeling cognitive activity based on synaptic modification depends in large part on how synapses are stabilized after firing. With respect to synaptic activity, there are numerous types of "learning," each of which has a different neuronal effect. Hebbian learning, for instance, occurs when the connectivity between two neurons increases after one produces an action potential in the other. The selectivity-learning rule, on the other hand, incorporates a variable threshold of activation because it modulates the type and level of response to sensory stimuli (for instance, the difference between looking at the sun or at the night sky).

Blais et al. demonstrate an important mathematical connection between biology and temporality, or the idea that modeling such processes as cognition involves the accounting for change rather than for absolute physical values, and in doing so demonstrates the process parallelism that pervades natural phenomena.

There is a need for a new class of brain diagnostics and therapeutic devices. There is a need to unify the "read" and "write" aspects of clinical neuroscience. There is a need for detecting disorders of and positively affecting the functioning of living tissues such as the brain and spinal cord.

SUMMARY

The present invention relates to a non-invasive system with diagnostic and treatment capacities that use a unified code that is intrinsic to physiological brain function. In an embodiment of the present invention, an approach to the treatment of disorders that supplements existing diagnostic and treatment methods with robust quantitative data analysis is presented. This is achieved by a unification of cognitive and neural phenomena known as the Fundamental Code Unit (FCU), representing identifiable patterns of brain activity at the submolecular, molecular, and cellular levels (intra-brain communications), as well as their manifestations in thought and language (inter-brain communications). In an embodiment of the present invention, a Medical CoProcessor (MCP) device correlates multiple data streams temporally using one or more read modalities, determines the patterns which are deleterious or sub-optimal, and uses a set of write modalities, or means to modify cognitive activity, to neutralize the negative effects of these patterns and stimulate patterns of activity which will have positive short- and long-term effects.

For example, in an embodiment, a computer-implemented method for affecting living neural tissue may comprise receiving at least one signal from at least one read modality, the signal representing release of photons from the living neural tissue, computing at least one signal to effect alterations to the living neural tissue based on the received input signal, the computed signal adapted to cause transmission of photons to the living neural tissue, and delivering the photons to the living neural tissue to effect alterations to the living tissue.

In embodiments, the received photons and the delivered photons may comprise at least one of near ultraviolet photons, blue photons, or green photons. The near ultraviolet photons may be a free radical reaction byproduct from mitochondria of the living neural tissue, the blue photons may be emitted by NAD(P)H upon absorption of near-UV photons, and the green photons may be generated by NAD (P)H oxidases, upon absorption of a (NAD(P)H-generated) blue photon. The near ultraviolet photons may have a wavelength of about 380 nm, the blue photons may have a wavelength of about 470 nm, and the green photons may have a wavelength of about 530 nm. The delivered photons may cause formation of at least one memory pattern in the neural tissue. The computed signal may be computed so as to cause the delivered photons to cause formation of at least one memory pattern in the neural tissue.

In an embodiment, a system for affecting living neural tissue may comprise at least one photonic read modality adapted to receive photons from mitochondria of the living neural tissue and generating a signal representing the released photons, at least one photonic write modality adapted to deliver photons to the living neural tissue to effect alterations to the living tissue based on at least one computed signal, and computing circuitry comprising a processor, memory accessible by the processor, and computer program instructions stored in the memory and executable by the processor to compute the at least one signal.

In an embodiment, a computer program product for affecting living neural tissue may comprise a non-transitory computer readable storage having program instructions embodied therewith, the program instructions executable by a computer, to cause the computer to perform a method comprising receiving at least one signal from at least one read modality, the signal representing release of photons from mitochondria of the living neural tissue, computing at least one signal to effect alterations to the living neural tissue based on the received input signal, the computed signal adapted to cause transmission of photons to the living neural tissue, and delivering the photons to the living neural tissue to effect alterations to the living tissue.

BRIEF DESCRIPTION OF THE DRAWINGS

The details of the present invention, both as to its structure and operation, can best be understood by referring to the accompanying drawings, in which like reference numbers and designations refer to like elements.

FIG. 22 is an exemplary illustration of an inductive powering system.

FIG. 23 is an exemplary table of advantages of aspects of technologies that may be utilized by embodiments.

FIG. 24 is an exemplary table of advantages of aspects of technologies that may be utilized by embodiments.

DETAILED DESCRIPTION

Figure 1:
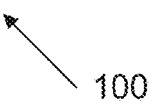
FIG. 1 is an exemplary illustration of chemical action potentials, by orbital.

The present invention relates to a non-invasive system with diagnostic and treatment capacities that use a unified code that is intrinsic to physiological brain function. In an embodiment of the present invention, an approach to the treatment of disorders that supplements existing diagnostic and treatment methods with robust quantitative data analysis are presented. This is achieved by a unification of cognitive and neural phenomena known as the Fundamental Code Unit (FCU), representing identifiable patterns of brain activity at the submolecular, molecular, and cellular levels (intra-brain communications), as well as their manifestations in thought and language (inter-brain communications). The FCU is further described in the following applications, which are incorporated by reference herein in their entirety: U.S. Provisional Application No. 61/241,314, filed Sep. 10, 2009, U.S. Provisional Application No. 61/322,158, filed Apr. 8, 2010, U.S. Provisional Application No. 61/588,666, U.S. patent application Ser. No. 12/880,042, filed Sep. 10, 2010, US Publication No. 2011-0060377 A1 published Mar. 10, 2011, now abandoned, U.S. patent application Ser. No. 13/083,352, filed Apr. 8, 2011, US Publication No. 2012-0064493 A1 published Mar. 15, 2012, now abandoned, and U.S. Pat. No. 9,399,144, filed Jan. 22, 2013, issued Jul. 26, 2016. Further the following applications are incorporated by reference herein in their entirety: U.S. patent application Ser. No. 13/747,448, filed Jan. 22, 2013, now U.S. Pat. No. 9,399,144, issued Jul. 26, 2016, U.S. Provisional Application No. 61/588,666, filed Jan. 20, 2012, U.S. patent application Ser. No. 13/083,352, filed Apr. 8, 2011, U.S. patent application Ser. No. 12/880,042, filed Sep. 10, 2010, U.S. Provisional Application No. 61/322,158, filed Apr. 8, 2010 and U.S. Provisional Application No. 61/241,314, filed Sep. 10, 2009.

The FCU utilizes read and write modalities to affect living tissue, such as neural tissue of the brain. The above-referenced documents describe a number of such modalities that may be utilized by the FCU. Embodiments of the present systems and methods may include modalities that operate by way of Photonic Signaling, as described below.

The Fundamental Code Unit (FCU) aims to unify the molecular, cellular, neural, cognitive, and linguistic layers of neurophysiological operation and postulates that all output of the brain originates from a single unit. These fundamental units are indivisible, reconfigurable, parallel, and recursive. Like the four nitrogenous bases comprising DNA, units are relatively simple when compared to the structures they create. These structures and their operations are governed by a golden mean energy ratio that applies to all levels of the body and brain. FCU units are transformed into brain function through mechanisms powered by unitary operators "unary plus" (+) and "unary minus" (−). In this paper, we explain the FCU theory and provide a detailed example of its operation within neocortical networks. Information is transmitted by several means within the neocortex, including chemical, electrical, mechanical, and optical. While each of these transmission systems runs the FCU code, we will specifically discuss photonic activity within the neocortex that is transduced into synaptic membrane potential changes via a cGMP-dependent mechanism, similar to that in the retina. In parallel to this process, the G protein/cGMP phosphodiesterase pathway is catalyzed via photostimulation and regulates membrane potentials through cGMP-gated ion channels, using a system of unitary operators. These systems are mediated by neuropsin (OPN5), a bistable photopigment. Observations of photonic signaling suggest that this self-regulating cycle may regulate neuroplasticity, both during memory formation and in adaptive responses.

Introduction. Fundamental Code Unit (FCU) theory postulates that all output of the brain originates from single units. These fundamental units are reconfigurable, recursive, and indivisible. Moreover, they exist in parallel, a characteristic integral to the complexity of cognition. Like building blocks, these units combine in many different patterns to produce thought and behavior. As with DNA, fundamental code units are themselves simple when compared to the complex structures they create. We posit that units are transformed into brain computation through mechanisms powered by unitary operators—binary schematics, "unary plus' (+) and "unary minus" (−). These operators are analogous to optic transistors which absorb and emit light according to a golden mean energy ratio of 3:5, which we propose applies at all levels of the body and brain. In this paper, we will discuss Fundamental Code Unit theory in detail and give a practical example of this theory operating in neocortical networks.

Information is transmitted by chemical, electrical, mechanical and, as we emphasize herein, optical means within neocortical networks. We show that each of these layers and mechanisms adheres to FCU theory. We will specifically discuss photonic activity, which is transduced into synaptic membrane potential changes via a cGMP-dependent mechanism similar to that in the retina. In parallel, the G protein/cGMP phosphodiesterase pathway is catalyzed via photostimulation and regulates membrane potential through cGMP-gated ion channels, using a system of unitary operators. Photonic control is mediated by the bistable photopigment neuropsin (OPN5) in neocortical synapses. Recently, photonic signaling has been observed which may help regulate neuroplasticity.

This optical circuit is a self-regulating cycle of photon-mediated events in the neocortex involving sequential interactions among 3 mitochondrial sources of endogenously-generated photons during periods of increased neural spiking activity: (a) near-UV photons (~380 nm), a free radical reaction byproduct; (b) blue photons (~470 nm) emitted by NADPH upon absorption of near-UV photons; and (c) green photons (~530 nm) generated by NADPH oxidases, upon NADPH-generated blue photon absorption. The bistable nature of this process provides evidence that an on/off (UNARY +/−) coding system exists at the most fundamental level of brain operation. As such, it provides a solid neurophysiological basis for FCU theory. The unique characteristics of these quantum-scale phenomena also provide explanations for how the brain is able to process such volumes of complex information using so little energy.

The Fundamental Code Unit Theory. Today, we understand the brain as a densely-wired, multidimensional system comprising up to about 100 billion neurons, all interacting on a millisecond timescale. Each of these neurons is connected by a myriad of transmission points that collectively generate complex outputs, such as sensation, thought, behavior, and learning. Each neuron can send and receive signals from up to $10^5$ synapses and can combine and process these synaptic inputs to implement a rich repertoire of operations. To better understand brain function, researchers have attempted to reverse-engineer neuronal networks and even to model the brain in its entirety. This approach is based on the assumption that neurons in-vivo act just like simple transistors in-silico. Unfortunately, transistor-based computing only reacts to static events whilst neurons can react to dynamic processes, so neither network nor whole-brain modeling have yet led to any deep insights into how the brain actually works. Unlike transistors, neurons are able to establish and change their connections and to vary their signaling properties according to natural rules, thus enabling them to encode experience (citation). The components of the brain are not static and biology does not operate at random; natural systems evolve according to the laws of physics and so can be both understood and anticipated.

To understand how complex brain functions result from observed neurobiological phenomena, multimodal investigation must be employed to explicate the physiologic and molecular mechanisms underpinning information storage and signaling, and those data reconciled with the reality of how neural networks self-establish and subsequently behave. FCU attempts to describe how brain activity is encoded and decoded hierarchically, first at a molecular, then at the cellular, network, cognitive, and behavioral levels.

It is widely accepted that neurons are responsible for action potential firing, release of neurotransmitters, and synaptic activity, but if we deconstruct the neuron we find dendrites, axon, myelin sheath, and other structures. Further magnification reveals that these are made up of molecules, which are in turn made up of atoms. Finally, it becomes apparent that neurons, like all matter, consist of specific arrangements of subatomic, quantum particles which nucleate according to entropic law to form the basis of our observable world. Interaction between photons and electrons are events which occur continuously and which obey consistent temporal and energetic rules. Photons and electrons always interact at a fixed ratio of 5:3, and this quantum level exchange propagates universally throughout all mechanisms of the brain and at every scale from subatomic to network-level. The ubiquity of this ratio within the nervous system highlights it as a constitutive characteristic of cognitive mechanics and which helps elucidate the nature of the mind's integral code.

Herein we offer a model for uniting our present understanding of behavior and cognition with the emerging body of literature which implicates these femtoscopic phenomena as constitutive elements of the same. FCU theory models the brain as a linguistic computation engine which translates fundamental units of photic, electric, and chemical interaction into observable behavior. By describing the transformational functions governing this engine, we may gain unprecedented insight into the brain's function, its dysfunction, and into approaches for modulating the same.

The Unitary System. The FCU theory posits that the physical phenomena of brain function are mapped to a unitary system and also that the brain communicates within itself and with the rest of the body via unitary operators. It is via this unitary system that quantum-level phenomena translate to biological processes and behavior. Although the physical processes which encode these phenomena vary across different levels of magnification, the processes can be described as sets of related algorithms, rooted in number theory, which in turn reflect the most basic patterns and sequences of our biology.

Photon-driven conformational changes in protein neurotransmitters form one of the primary mechanisms by which information is transferred and stored within the brain. Apart from controlling the concentration and neural regions affected by controlled neurotransmitter release or inhibition, electromagnetic radiation can be used to a similar effect, by inducing conformational changes in the proteins already present near the synapse site of neurons.

A powerful write modality can be built using FCU-based mechanism for exchanging information within the brain: endogenous photon-triggered neuropsin transduction, followed by conformational changes in protein neurotransmitters. By mimicking the causal process by which the brain writes new information to neural networks, FCU/MCP can co-opt existing chemical processes to achieve control over this activity.

In a neuropsin-mediated unary-coded photonic signaling scheme, neuropsin plays a role of a unary +/− encoder, capable of producing patterns of LTP in synaptic ensembles, and wiring changes in local synaptic circuits. Both phenomena may be reflective of and serve as a coded reporter of, each of neuropsin's two stable conformational states: i.e., incremental unary (+/−) switches based on value structure of a non-deterministic state, with or without linear or potential pathway. The incremental unary "+" switch is near UV photon absorption by neuropsin, producing its incremental unary "+" state which is G-protein activation. The incremental unary "−" switch is blue (.about.470 nm) photon absorption, which converts into the conformation incapable of G-protein activation.

Multiphoton absorption by neuropsin may be possible, if neuropsin is in close proximity to a photon source, therefore free radical reactions can generate photons of longer wavelength, >600 nm. Multiphoton absorption of two or more of such (red) photons can provide energy equivalent to that of a single UV photon; this means that if two red photon absorptions occur, it may also serve as the incremental unary "+" switch, substituting for a single UV photon. An advantage of longer wavelength photons is that they travel longer distances in brain tissue than do UV photons.

Other key regulatory enzymes, like NAD(P)H oxidases (NOXs), may be used to create such incremental unary switches. Flavoproteins like NOXs absorb blue photons, which cause them to emit green photons. Like NAD(P)H, it is autofluorescent, but is higher on the wavelength spectrum. The photons which NOXs absorb are the same photons that the UV-stimulated NAD(P)H emits: about 470 nm (blue). These photons trigger the production of photons of even longer wavelength, by NOXs' well-documented ability to autofluoresce: 520 nm green photons are emitted.

Quantally controlled, unary incremental switches in the brain may use a multiplicity of other(+/−) switches in the brain, as NOX's photonic (+/−)unary coding may serve as switches for yet another regulatory process, such as reactive free radical generation, which produces UV photons that start the scheme, involving NADH, neuropsin in the first place. Therefore, NOX can complete the photonic scheme of the brain's infinite "do loop", reaching quantum tunneling & entanglement, which open the door for long-distance signaling, even from outside the brain.

Downstream consequences of neuropsin's ability to produce spatia-temporal distribution patterns of "+" and "−" states in synaptic domains are potentially profound, in their implications for memory formation, both short- and long-term, each of which are semi-independent processes.

Long Term: There exists a link between long-term memory (LM) and cellular/synaptic processes such as long-term potentiation/depression (LTP/LTD). Furthermore, LTP/LTD requires some sort of structural changes/protein synthesis: 1. changing neurotransmitter receptor expression, 2. increasing synapse size, 3. changing synapse anchoring, which makes ADP/ATP, being the major energy source in neurons and glial cells, required for LM.

Short Term: There is good evidence that persistent neuronal firing of those populations of neurons that encode the memory is required, similarly to refreshing computer's rapid-access memory. Apart from ATP/ADP fueling persistent activity by driving ATP/ADP dependent ionic pumps and the maintenance of synaptic receptors, ATP/ADP has also been linked directly to the emergence of persistent activity through its modulation of ATP modulated potassium channels.

Since the discovery of purinergic signaling the involvement of ATP/ADP-mediated signaling through neuronal and glial receptors is seen in almost every aspect of brain function. FCU/MCP, can guide purinergic signaling, including its effects on learning and memory, focused more on the therapeutic potential of purinergic modulation in various CNS disorders.

The electrochemical action potentials that drive neuronal communication show this unitary system at work, dominated by the photoelectric exchange ratio. Examples of chemical action potentials, by orbital, are shown in FIG. 1. This ratio (modeled by the unitary system) can be correlated with specific cognitive activities. For instance, a quantum logical gate can be described as a unitary operator, assuming arguments and values in a product-Hilbert space. The gate can be viewed as a truth table that transforms+ and m; likewise the gate can be represented as a matrix. One can observe the same quantum physics at work when we consider cognition at the meso-level by examining the physiology of the brain; this demonstrates the multi-level applicability of the unitary system.

The unitary model can also explain the behavior of a neuron. A neuron adds and subtracts excitatory and inhibitory inputs until it reaches a threshold, at which point it fires a single impulse or action potential. At the neuromuscular junction, virtually every action potential in the presynaptic motor neuron triggers an action potential in the postsynaptic muscle cell. However, the situation at synapses between neurons is much more complex because the postsynaptic neuron commonly receives signals from many presynaptic neurons. A single neuron can be affected simultaneously by signals received at multiple excitatory and inhibitory synapses. Just as the brain continuously integrates countless signals, neurons likewise continuously integrate signals to determine whether or not to generate an action potential based on the unitary system.

At a synapse, a neuron releases neurotransmitters that excite or inhibit another cell or alter its response to other inputs. Excitatory neurotransmitters increase firing rate. Inhibitory neurotransmitters decrease the chances of the neuron firing. Each neuron is influenced via multiple neurotransmitters acting at multiple synapses by dozens of other neurons. Following the release of a neurotransmitter and the subsequent activation of a receptor, it is important that the response is terminated and the system reset so that a subsequent activation can occur. This is achieved through the removal of the neurotransmitter by metabolic enzyme activity and by passive or active uptake activities. Increased concentration of the transmitter at a synapse for a longer period of time occurs if the uptake mechanism is blocked. Therefore, a neurotransmitter uptake blocker may have an effect similar to a postsynaptic agonist of that transmitter. For uptake to take place, the neurotransmitter must be recognized by an uptake mechanism and so it is common for structural analogs of the neurotransmitter in these processes (noradrenaline, serotonin, and dopamine, for example) to be used clinically. Once again, we see the unitary system at work in the form of chirality. That is to say, a molecule may 'fit' or 'not fit', each of these two possibilities representing unary+ or unary –.

The Neurophotonic Cycle. Presently, we turn our attention to the proposal that there exists in the brain an endogenous photonic signaling system. This system appears to exploit the photopigment neuropsin's bistability as a biological switch, a transistor of sorts. The existence of such a mechanism provides a plausible neurophysiological basis for elements of the FCU theory and would further lend support for the universal use of unitary operators. Here we examine a chain of evidence supporting the hypothesis that endogenously generated photons, tied to the metabolic state of brain cortical synapses, transmit useful information to both neuronal growth cones and tripartite synapses connected to astrocyte networks. Such networks have recently been shown to express the bistable rhodopsin-like photopigment neuropsin (OPN5), amongst other components that are similar to those employed in retinal rod phototransduction. Here, rhodopsin photostimulation triggers transducin activation and release of the a subunit, which is involved in the regulation of cyclic GMP (cGMP)-gated ion channels. These components are related to transduction cascades in the visual and olfactory systems, which powerfully amplify and transduce non-electrical stimuli into local electric field changes.

This novel signaling scheme, underpinned by a cascade of photonic emission and absorption of photons at discrete wavelengths, may offer a mode of coded information transmission that parallels the known pathways of neural network communication. This hypothesized dimension of control of neural plasticity may be of significance for effective neuroplasticity-driven processes, such as memory and adaptive responses to experience. The two photon-interconvertible conformations of neuropsin (UV-photon-absorbing, and blue photon-absorbing), demonstrate the unitary +/– operators of the FCU theory in action. If such activity does exist, it would better explain the dynamicity and complexity of cognition that present models of neural plasticity do not account for. Moreover, similar unitary, light-mediated activity has been observed in retinal neurons.

Structurally homologous rhodopsin, a photopigment termed neuropsin (OPN5) has been identified in the brains of mammals, including humans. This pigment is also found in retinal ganglion cells (Nieto, P. S. et al., 2011), where neuropsin absorbs photons produced by ambient sunlight to influence photoperiodic responses and in the avian brain hypothalamus (citation). Neuropsin also plays a functional role in the mammalian cerebellum and hippocampus and has been implicate din the formation of long term synaptic potentiation (LTP), known to be a key step in long-term memory formation and other adaptive neuroplastic responses. Neuropsin has also been shown to trigger proteolytic cascades involving neuregulin activation, yet the neurophysiological role of neuropsin (and other bistable opsins), along with their potential for photon absorption and regulation within deep brain structures, remains unknown.

This paper discusses the possibility of a photonic signaling scheme within the human brain, energized by an endogenous source of UV photons. It also reports recent findings that support the existence of these photons, which seem to be natural byproducts of reactive free radicals, generated by mitochondrial metabolism. Since the regulated activity of NAD(P)H oxidases purposely generates free radicals as a means of metabolic control, these processes comprise a cyclical chain that supports a novel signaling mechanism within the brain.

Figure 2:
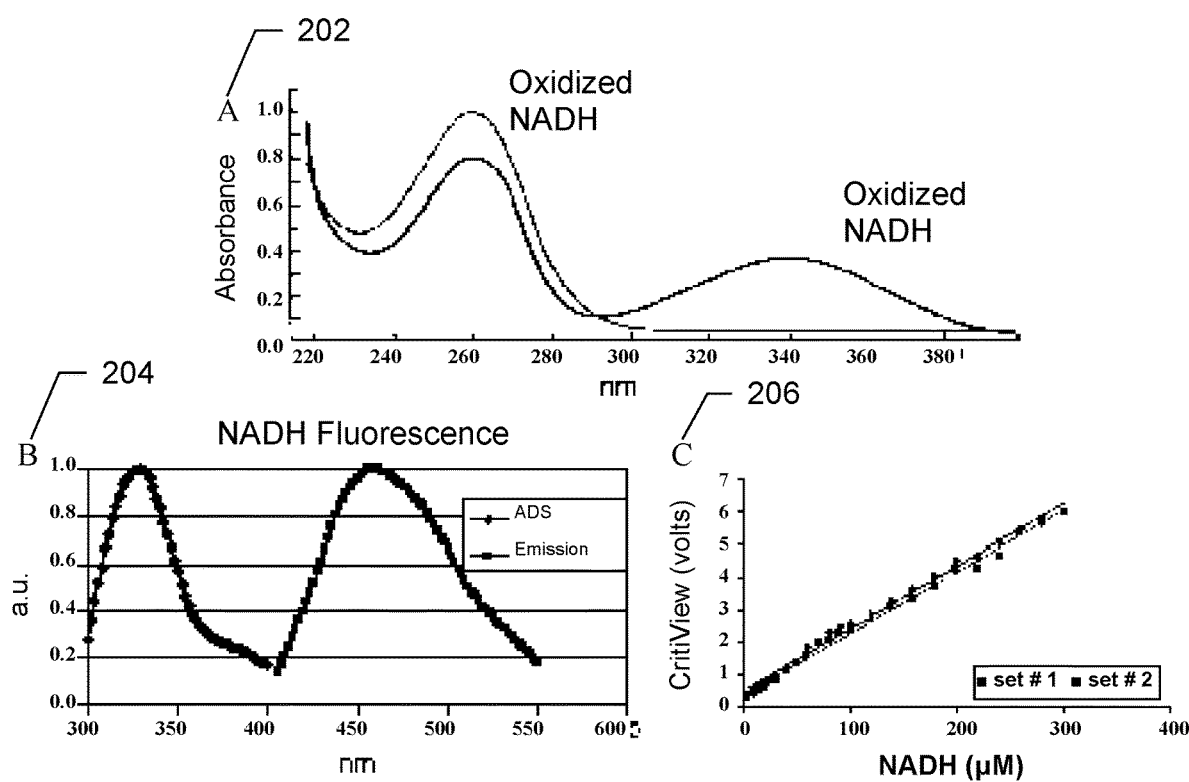
FIG. 2 is an exemplary illustration of the absorption and fluorescence spectra of NADH.

The proposed sources of these endogenous photons are: (a) NAD(P)H, which auto-fluoresces upon UV (~380 nm) photon absorption, producing blue (~470 nm) photons; and (b) mitochondrial NAD(P)H oxidases, flavoproteins which emit green photons (~520 nm) upon absorption of blue photons (such as those emitted by UV-stimulated NAD(P)H). The auto-fluorescent properties of NAD(P)H and mitochondrial flavoproteins have both been shown to depend on the cellorption. Examples of the absorption spectrum of oxidized and reduced NADH 202 are shown in FIG. 2, as are NADH absorption and fluorescence spectra 204 and the effect of NADH concentration in solution 206 on the fluorescence intensity measured in 2 sets of NADH samples.

All components of this transduction cascade are closely juxtaposed within synaptic regions where they can efficiently absorb photons emitted during mitochondrial metabolism. As such, this cascade is responsive to the synaptic domaiynaptic domainetab. This system is quite similar to the phototransduction mechanism occurring in retinal rods.

This photonic signaling cycle runs as follows:

1. Characteristic local field potential (LFP—used for storing long-term memory) oscillations enhance the metabolism of mitochondrial electron transport activity and create free radicals in a process that generates NEAR-UV photons (~380 nm).

2. These NEAR-UV photons (~380 nm) are absorbed by NEUROPSIN and NAD(P)H.

3. NEUROPSIN absorption of NEAR-UV catalyzes the stable conformational change of NEUROPSIN into a G-protein-activating form ("UNARY+").

3a. The active G-protein contains a cGMP phosphodiesterase, which catalytically degrades cGMP. The result of phosphodiesterase activation is a lowering of cGMP levels in microdomains of neuroglial networks.

3b. This lowering of cGMP amplifies the initial photonic signal, and closes cGMP-gated cation channels.

3c. This exerts a hyperpolarizing (inhibitory) influence on cGMP-gated channel-containing synapses, affecting the neural networks in ways that could be complex. For example, if those synapses are on GABAergic neurons, the result could be disinhibition of GABAergic input, thus tending to activate the network (Tamura, H. et al., 2012)

4. NAD(P)H absorption of NEAR-UV triggers BLUE (~470 nm) photon emission another metabolically-stimulated source of photons.

4a. These BLUE photons (~470 nm) are absorbed by NEUROPSIN, causing a GREEN photon (~520 nm) emission, triggering a stable conformational shift to the inactive state ("UNARY−").

4 b. Evidence indicates that GREEN (~520 nm) photon absorption targets regulate cell proliferation (REF). The precise targets and mechanism are hypothesized to involve interleukins, known neurotrophic and survival-promoting agents in the hippocampus.

4c. GREEN (~520 nm) photon emission also inhibits free radical generation, the hypothesized result of inhibitory auto regulation of NAD(P)H OXIDASES ("NOX"). This serves as a homeostatic mechanism, resulting in dual (+/−) control of UV photon dual (+/ostatic ibits free radical generation, the photon-driven control mechanism for neuropsin regulation.

The end result of this cyclical photonic regulatory scheme is that neuropsin's active/inactive state ratio is controlled in local microdomains, to determine the pattern of cGMP levels in larger synaptic ensembles. This cycle constitutes a powerful mechanism for amplification of weak photon emissions and control of downstream transduction events. Further, it is to be noted that Endogenously-generated near-UV (~380 nm) and blue (~470 nm) photons trigger, in turn, stable conformational shifts in neuropsin corresponding to "on/off" (unary +/−) states for activation of a cyclic GMP-dependent transduction and amplification cascade.

Photon sources are proximal to one another, with UV photons being produced from free radical reactions and blue photons being produced by NAD(P)H, connecting FADnd control of downstream transduction events and duneuropsin within several microns (the synaptic cleft and nerve terminal). The targets ensure a high capture rate for locally emitted photons, as all these events are taking place in or near the synaptic regions containing mitochondria, which are the main source of free radical-generated near UV photons (~380 nm). The processes regulated by this unary (+/−) mechanism include growth cone routing, synaptic strength and LTP, all essential events guiding adaptive neuropl asti city.

Figure 3:
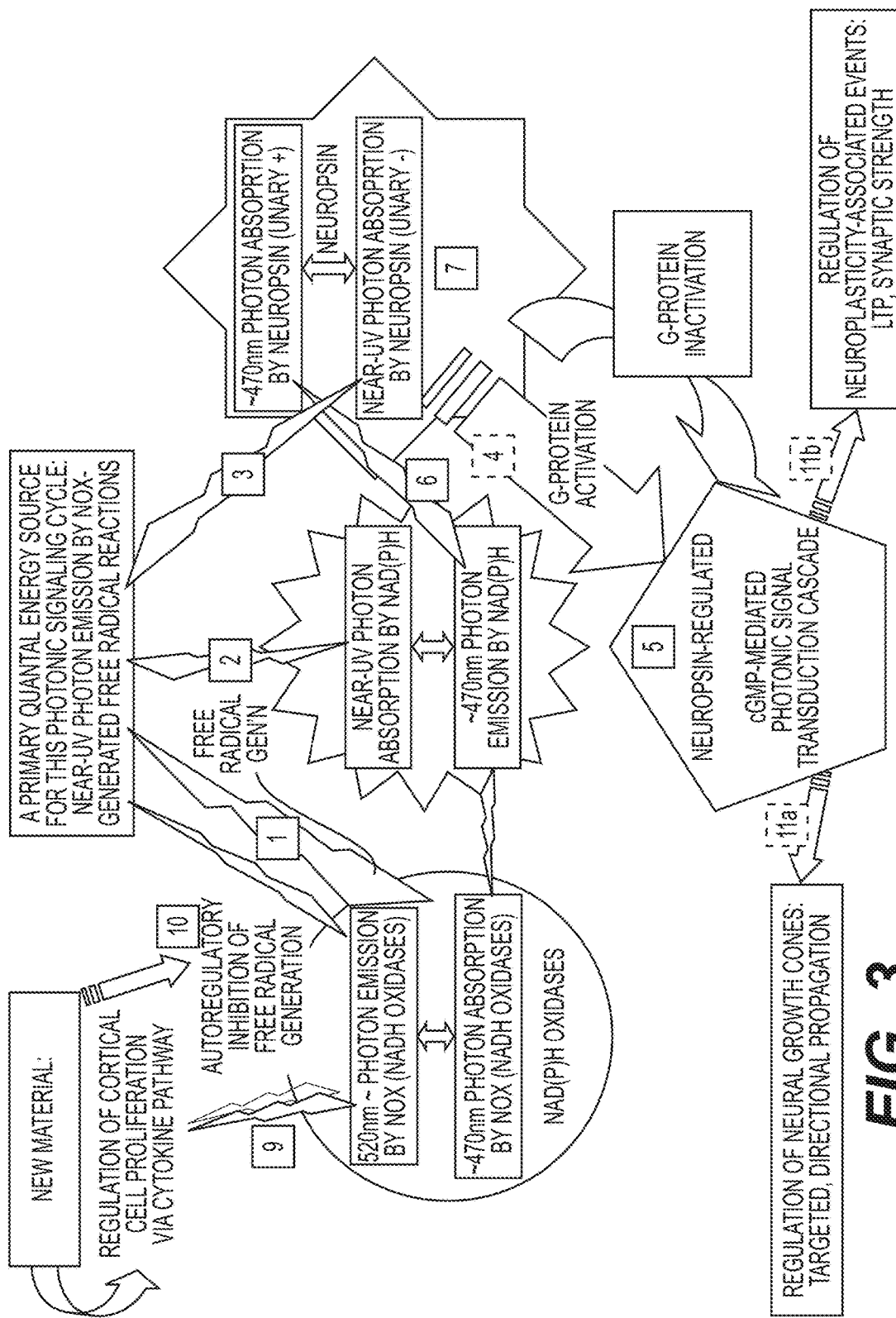
FIG. 3 is an exemplary schematic of a series of steps in a neuropsin-controlled cGMP-mediated transduction cascade cycle.

FIG. 3 is a schematic of a series of steps in this neuropsin-controlled cGMP-mediated transduction cascade cycle, linked to neuroplastic brain changes such as memory pattern formation in the hippocampus. In relation to FIG. 4, we will: (a) Define the relevant properties of the three key components of this proposed photon transfer scheme: neuropsin (OPN5), the reduced form of the nicotinamide adenine dinucleotide (NADH and NAD(P)H) and the NAD(P)H oxidases, which are auto fluorescent flavoproteins that generate reactive oxygen species (en species (enerte the evidential linkages that support this cGMP-mediated neuropsin-switchable phototransduction cascade; and (c) discuss the evidence supporting a key role for this photonic mechanism in regulating synaptic responses, neural survival and proliferation, and growth cone guidance.

A. Neuropsin: Phototransduction Properties. Light is potentially the most important signal for living organisms, as most life on Earth ultimately depends on sunlight energy. Opsins are the universal photoreceptor molecules of all visual systems in the animal kingdom and are the primary class of molecules with the ability to undergo conformational changes in response to photon absorption. These provide the molecular basis for visual and nonvisual photoreception. Many animals utilize light cues to regulate biological processes, including vision and circadian clock regulation, and seasonal photoperiodic responses in birds and mammals. Rhodopsin is the key photoreceptive protein in the visual system but many similar types of opsin are also present within and throughout the mammalian brain; most of these have yet to be found functions. To date, researchers have largely ignored the photoreceptive capabilities of opsins situated deep in the brain, as it has been assumed that they never encounter light.

Figure 4:
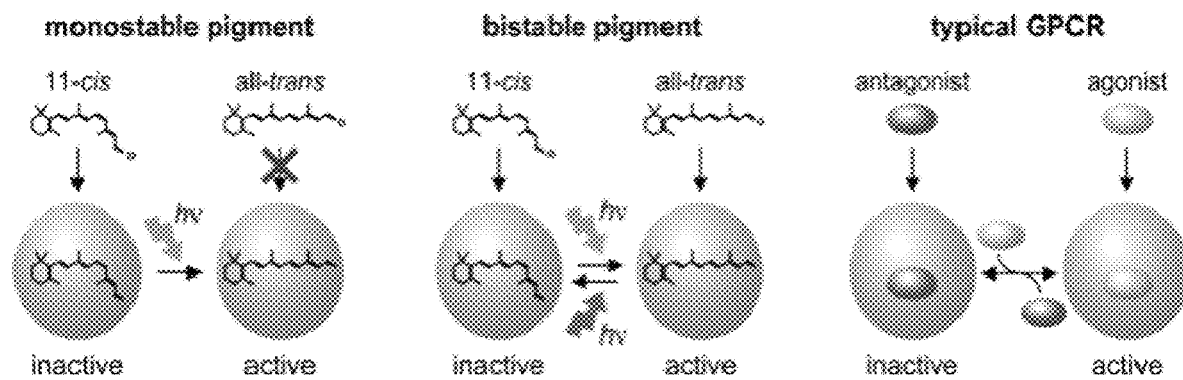
FIG. 4 is an exemplary illustration of a comparison of activation schemes among monostable and bistable pigments and typical GPCRs.

All known members of the opsin family exhibit chromophore binding via a Schiff base linkage even if they never encounter light sensitive capabilities. Retinal, as yet the only known chromophore for all opsins, exists in two forms: 11-cis retinal and all-trans retinal, the latter formed by photon absorption by the 11-cis form. In the retina and in certain other cases, the all-trans form induces a conformational change in the opsin moiety that enables G-protein activation. FIG. 4 illustrates a comparison of activation schemes among monostable and bistable pigments and typical GPCRs.

Neuropsin exists in two relatively stable, light interconvertible forms: vertible forms: y interconvertible by UV and visible light irradiations, respectively, indicating that cOpn5m is a bistable pigment. The absorption maxima of each of these forms were ~360 nm and ~474 nm, respectively. A GTPgm binding assay clearly showed that the visible light-absorbing form having all-trans retinal activates Gi type of G protein, whereas no Gt or Gq activation ability was observed or Gq activation was observed all-neuropsin (photo-regulated G-protein activation) qualitatively parallels the behavior of rhodopsin in retinal rod outer segments; in rods, rhodopsin-catalyzed activation of a G-protein (transducin) is also triggered by photon absorption. While rhodopsin is monostable, neuropsin is bistable and may provide advanced switching capability.

These properties of neuropsin define an important difference between neuropsin and rhodopsin: its well characterized photoreceptive relative; rhodopsin decays spontaneously after photostimulation, returning to its original conformation, while neuropsin, on the other hand, is bistable. Each of the two conformations: (a) the ~470 nm (visible light) absorbing form activates a G-protein mediated phototransduction cascade, and (b) the ~380 nm (UV) absorbing form, is long-lasting. Notably, an active event (rather than spontaneous decay) is required for each of the following (a) the following (a/b) transitions, below:

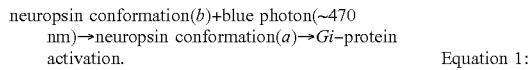

neuropsin conformation(b)+blue photon(~470 nm)→neuropsin conformation(a)→Gi-protein activation.    Equation 1:

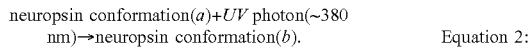

neuropsin conformation(a)+UV photon(~380 nm)→neuropsin conformation(b).    Equation 2:

There is evidence suggesting that these two photon-induced conformational transitions are key components of a photon-regulated switching mechanism that regulates synaptic function in the mammalian brain. To help frame (and support) this hypothesis, we should first review the photosensitive properties of the neuropsins found in retinal ganglion cells and the avian brain.

B. Retinal Ganglion Cells: Localization and Function in Vision Processing

Photoresponsive retinal ganglion cells are involved in many functions in the human brain which do not contribute to conscious visual experience, such as pupillary light responses and photic entrainment of daily rhythms. (Nieto, P. S. et al., 2011). The expression of neuropsin has been detected in a study of the intrinsic photoresponsiveness of the rat retinal ganglion cell line, RGC-5, by testing for the presence of non-visual opsins and assessing changes in intracellular Ca2+ mobilization triggered by brief light pulses. They detected OPN5 immunoreactivity in both RGC-5 cells and in the rat's interior retina in the ganglion cell layer. Furthermore, white light pulses of different intensities and durations elicited changes in both the intracellular Ca2+ levels and also in the induction of c-Fos protein in RGC-5 cell cultures.

Figure 5:
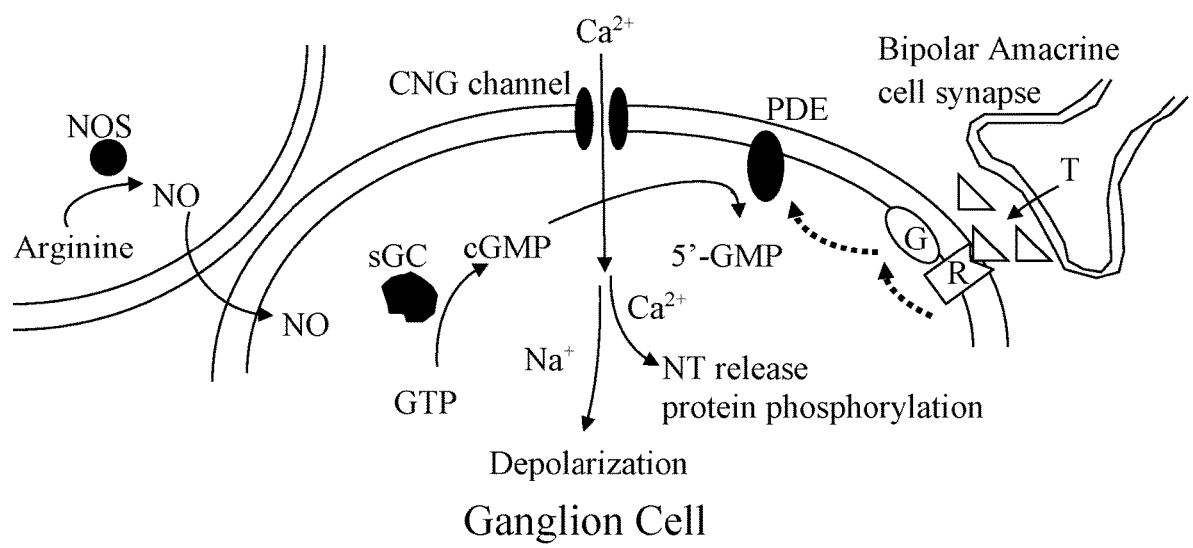
FIG. 5 is an exemplary schematic representation of pathways that might regulate the activity of the cGMP-gated channel in retinal ganglion cells.

FIG. 5 is a schematic representation of pathways that might regulate the activity of the cGMP-gated channel in retinal ganglion cells. Activation of cGMP-gated channels increases Ca2+ influx to enhance Ca2+ driven processes.

The results demonstrate that RGC-5 cells expressing diverse putative functional photopigments display intrinsic photosensitivity which accounts for the photic induction of c-Fos proteins and changes in intracellular Ca2+ mobilization. The presence of OPN5 in the GCL of the rat retina suggests the existence of a novel type of retinal ganglion cell containing photoreceptors. Its main projection is to the suprachiasmatic diurnal rhythm generator in the hypothalamus in order to entrain daily rhythms to seasonal changes in light levels.

However, information on the wavelength action spectrum of neuropsin-mediated photoresponse was not available (broad spectrum light stimulation was used). Nonetheless, it does suggest that if neuropsin's light stimulation is mediated by photon-triggered G-protein activation mediation, other key components of retinal rod phototransduction may also be found.

C. Avian Hypothalamus: Localization and Function in Vision Processing. It is known that certain avian species detect light by deep brain photoreceptors to regulate seasonal cycles of reproduction. These photoreceptors are usually found in brain regions distinct from other known light-responsive areas, such as the retina and pineal gland. Neuropsin (OPN5) has been identified as a deep brain photoreceptive molecule in the paraventricular organ of quail brain. Heterologous expression of this avian neuropsin in *Xenopus* oocytes resulted in light-dependent activation of membrane currents.

Figure 6:
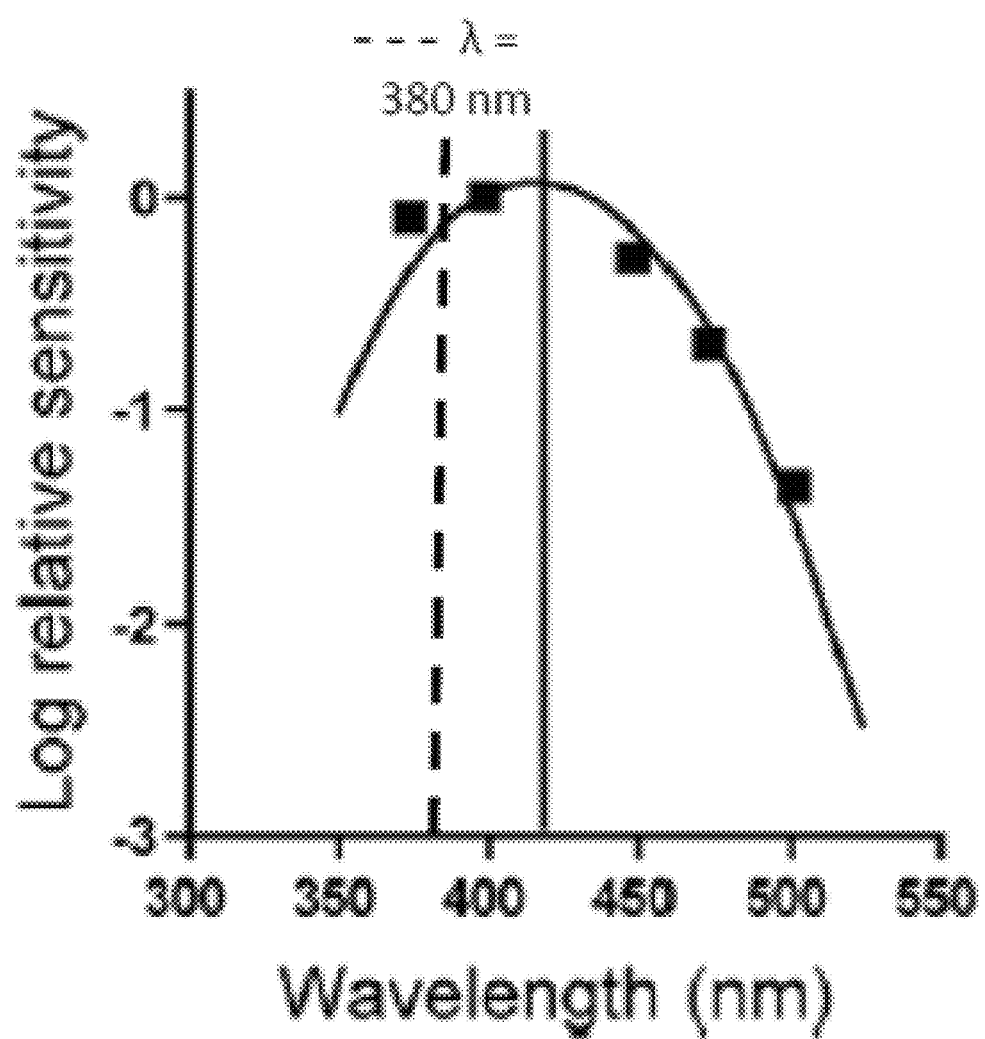
FIG. 6 is an exemplary illustration of an action spectrum for the avian brain OPN5-mediated photocurrent.

FIG. 6 shows an action spectrum for the avian brain OPN5-mediated photocurrent. The dashed line represents 380 nm—peak UV absorbance for mammalian neuropsin. As shown in FIG. 6, the action spectrum of avian showed peak sensitivity m of avian shot activation of membrane neuropsin in mice and humans. This is the form that transitions to conformation (a) and subsequently activates G-protein.

Near UV light subsequently activates G-protein.da, a neuropsin-triggered photocurrent to near UV light subsequently activates pinealectomized quail, ruling out both retina and pineal as the source of the response.

Figure 7:
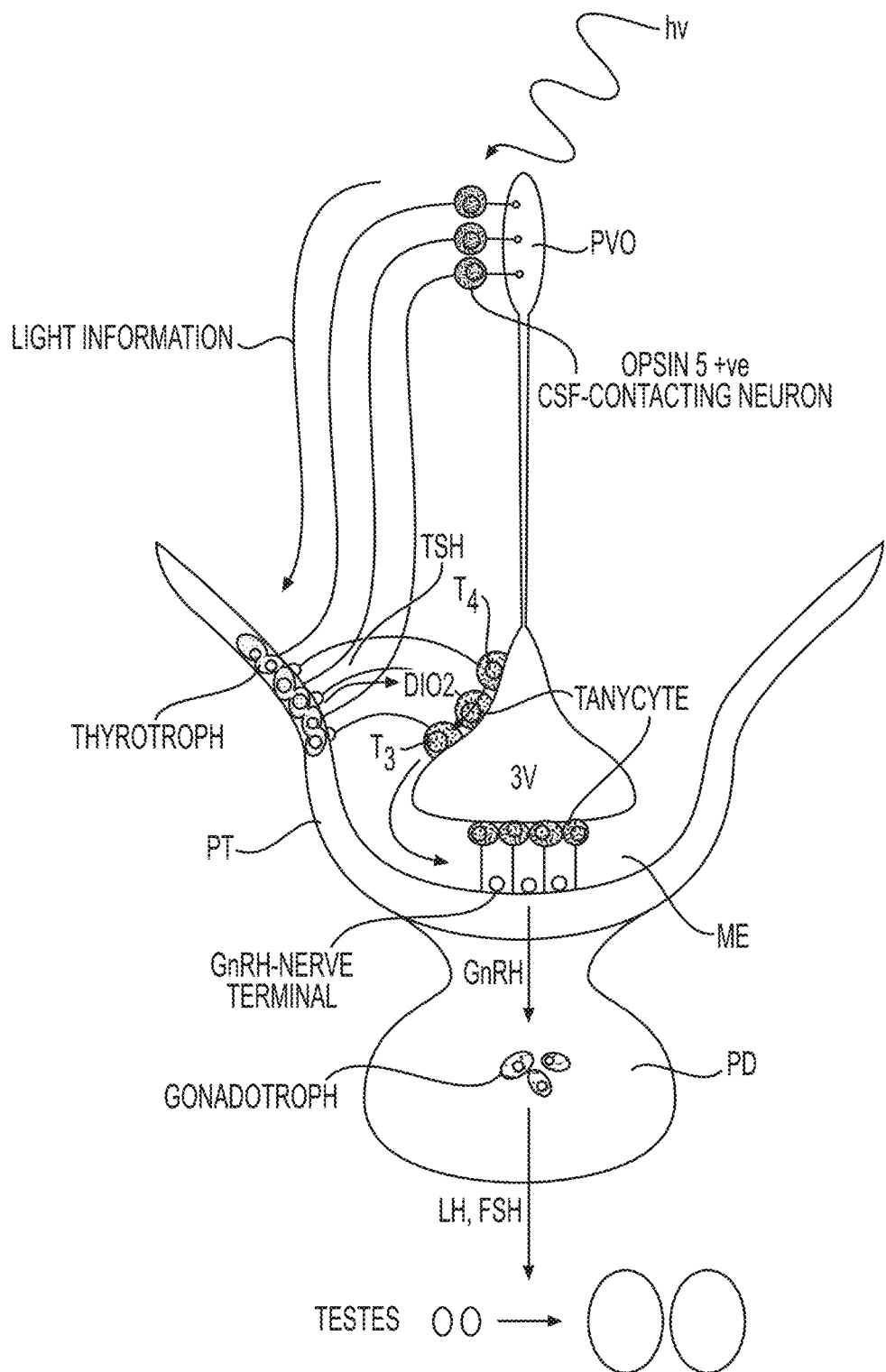
FIG. 7 is an exemplary diagram of an example of a neuropsin UV photon-triggered signal transduction pathway.

Taken together, these findings indicate that in at least some avian species, neuropsin appears to be photoreceptive within deep brain molecules that regulate seasonal reproduction in birds. This response is mediated by a UV photon-stimulated conformational shift of neuropsin to the G-protein activating conformation that initiates a transduction cycle that may resemble in other ways (e.g., powerful signal amplification ability) the retinal rhodopsin-mediated phototransduction cascade, resolved as cell membrane potential modulation. An example of a neuropsin UV photon-triggered signal transduction pathway is shown in FIG. 7, which shows the role of OPN5 in a photoperiodic signal transduction pathway in birds.

Light detected by OPN5 in periventricular organ (PVO) neurons in transmitted to the pars tuberalis (PT) of the pituitary gland. This induces thyroid stimulating hormone (TSH) expression in the pars tuberalis PT. This event induces TSH expression of type 2 deiodinase (DIO2) in tanycytes (cells lining the third ventricle (3V) and contacting cerebrospinal fluid (CSF)). DIO2 converts thyroid prohormone T4 to the bioactive hormone tri-iodothyronine (T3). Long-day ventricle (3V) and contacting cerebrospinal fluid (CSF). DIO2 convernals and glial processes and induce GnRH secretion.

D. Proposed Functions of Neuropsin in Synaptic Modulation and Axon Guidance.

Neuropsin seems to be localized within the synaptic cleft domain of mouse hippocampal synapses, with other concentrations elsewhere in the brain. Recent evidence suggests that neuropsin plays a key role in neuroplasticity-associated and memory-associated events, such as long-term potentiation number and axon guidance during neural circuit formation. Although the evidence for neuropsin role in these events is compelling, to date no claim has been made for finding conformational transitions of neuropsin triggered by photon absorption. To explore the possible role of such deep brain photonic mechanisms, we must first review the proposed mechanism of action believed to be responsible for these neuropsin-mediated regulatory events, in whole or in part.

Immunocytochemical localization studies showed that neuropsin co-localizes with antibodies to the neuregulin isoform NRG-1; the latter is expressed both in excitatory and inhibitory neurons of the hippocampus and the prefrontal cortex. These investigators provided strong evidence for the involvement of neuropsin in the modulation of synaptic plasticity, specifically via regulation of GABAergic transmission, discovering that neuropsin knock-out mice exhibited impairments in formation of long-term potentiation (LTP) within the synapses of hippocampal Schaffer collateral cells. These LTP deficiencies may be attributed to the actions of neuropsin as an extracellular protease and demonstrate neuropsin's ability to activate the known modulator of synaptic plasticity neuregulin. Neuregulin is released from the extracellular matrix, enabling it to phosphorylate its receptor (ErbB4), triggering downstream effects on synaptic plasticity, including LTP facilitation. Signaling molecules are accumulated and associated with HSPGs in the synaptic cleft, where neuropsin cleaves the mNRG-1 form neuregulin at three sites. This cleavage removed the heparin-binding domain of NRG-1, releasing the ligand moiety from the matrix-glycosaminoglycan pool and enabling it to trigger the phosphorylation of the synaptic plasticity regulator, ErbB4.

Figure 8A:
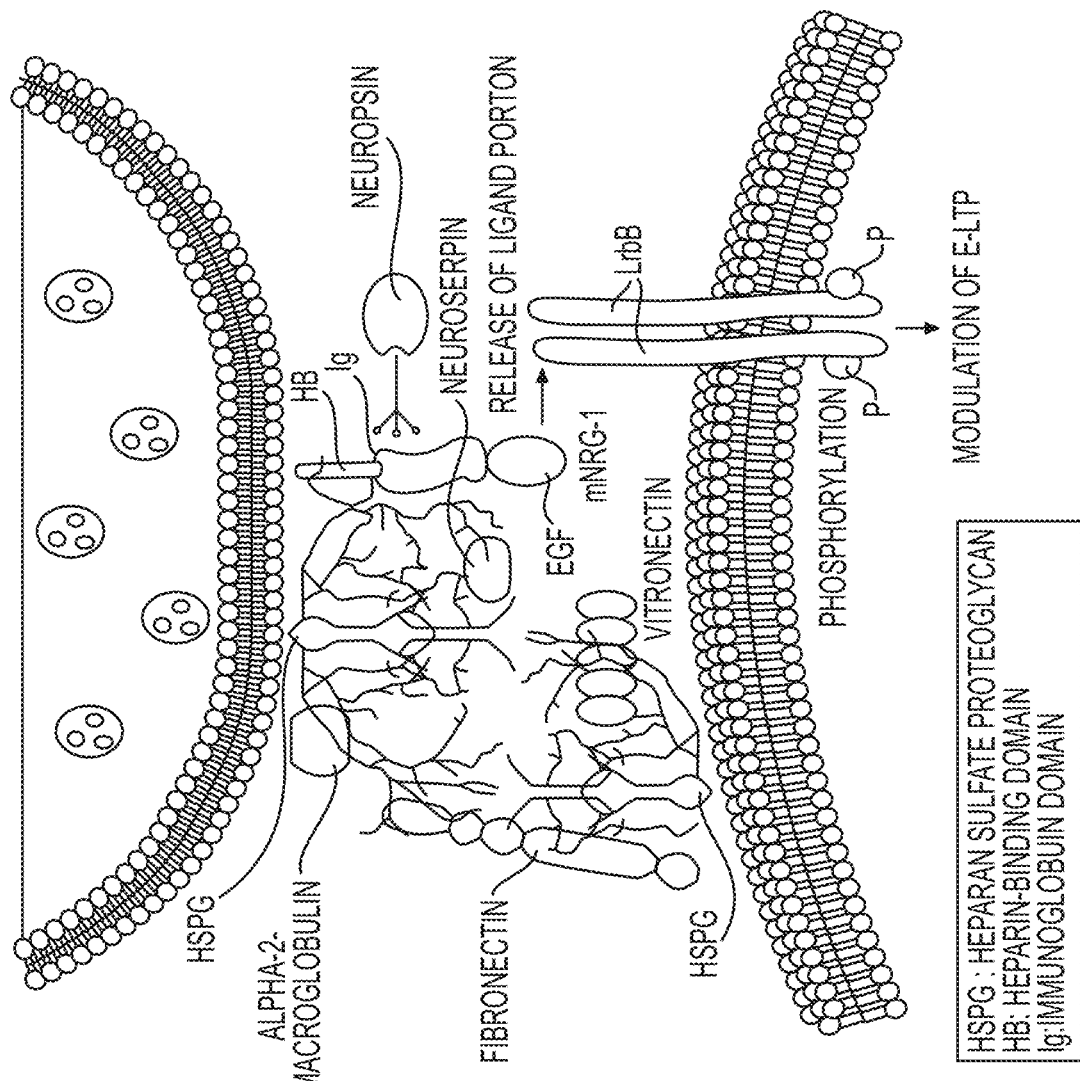
FIG. 8A is an exemplary illustration of neuropsin's role in the activation of neuroplasticity-associated signaling pathways within the synaptic cleft.
Figure 8B:
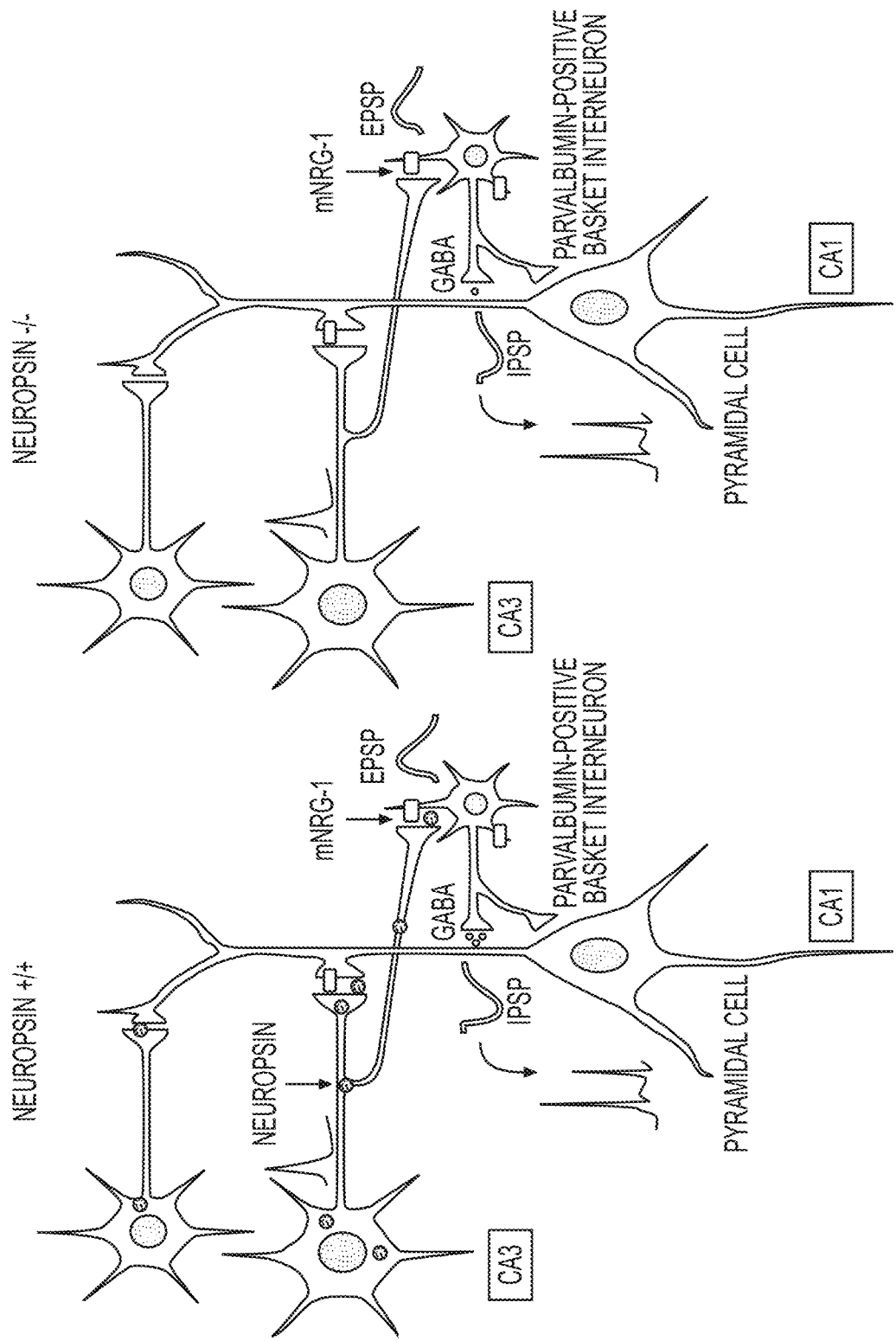
FIG. 8B is an exemplary illustration of neuropsin's role in the activation of neuroplasticity-associated signaling pathways within the synaptic cleft.

FIG. 8 illustrates neuropsin's role in the activation of neuroplasticity-associated signaling pathways within the synaptic cleft.

This neuropsin-triggered, neuregulin-released signaling system may be involved in human cognition and dysfunction within these symptoms may lead to mental disorders such as schizophrenia. Supporting this claim is the observation that the application of recombinant neuregulin (NRG-1) to the aforementioned LTP deficient neuropsin knockout mice reversed the effects of gene knockout, via activation of ErbB4 and GABA-A receptors. NRG-1 acutely depotentiates LTP when induced by theta-frequency stimulation in the hippocampus. Protease activity of neuropsin in the amygdala of mice (also localized within synaptic clefts) plays a critical role in stress-related synaptic plasticity. It does so by regulating the activity of NRG-1 isoform of neuregulin.

Stress, induced by prolonged restraint (6 hours), results in neuropsin-dependent cleavage of the axonal guidance and differentiation factor EphB2 in the amygdala, causing dissociation of EphB2 from the NR1 subunit of the NMDA receptor, thereby enhancing NMDA current. Concomitantly, increased anxiety levels are observed. In parallel, neuropsin cleavage of EphB2 enhances the expression of the microtubule association regulatory Fkbp5, also involved in axon guidance and propagation. Solidifying their case was the observation that neuropsin gene-knockout mice do not show EphB2 cleavage and dissociation from NRG1, correlating with attenuation induction, Fkbp5 gene and lower anxiety-like behavior. From these observations, they conclude that neuropsin is involved in a novel neuronal pathway linking stress-induced proteolysis of EphB2 in the amygdala to anxiety.

Neuropsin affects neuroplasticity and synaptic transmission, mediated by neuropsin's role as a protease. The photoreceptive properties of neuropsin may relate to the following key questions about neuropsin's proteolytic activity: Is neuropsin always active as a neuregulin-cleaving and EphB-cleaving protease, or is neuropsin a member of the class of "switchable" proteases, whose activity triggers or activates the proteolytic actions of neuropsin?

To address this question, it is worth considering both: (a) the rationale for a switchable mechanism regulating neuropsin's proteolytic activity; and (b) evidence supporting the hypothesis that photon absorption by the opsin chromophore retinal (which is known to be associated with the neuropsin protein moiety in retinal ganglion cells and the avian brain) may trigger conformational changes that activate neuropsin's proteolytic activity and/or other neuropsin-triggered mechanisms regulating LTP, neurogenesis, and/or other synaptic events.

Several lines of evidence support the hypothesis that photon absorption by neuropsin may regulate neuropsin in downstream synaptic and/or axon-guiding actions in the hippocampus and elsewhere in the mammalian brain:

In the avian brain, photonic mechanisms underlie neuropsin's role in regulating synaptic activity of paraventricular organ cells, associated with photoperiodic responses.

Cyclic GMP-gated channels similar to those found in retinal ganglion cells and vertebrate retinal photoreceptors have been found to be widespread in the mammalian brain.

These cGMP-gated channels and other known components of the neuropsin-associated cGMP-mediated phototransduction mechanisms of retinal ganglion and avian brain cells (such as the cGMP phosphodiesterase) have been found to regulate LTP in mammalian brain, including the hippocampus.

Switchable proteases are known to be active in other neuroregulatory pathways, such as in the activation of class proteases (the caspases), a key step in the programmed cell death pathway known as apoptosis. Apoptosis is an important pathway for normal organ maintenance and senescence, and is also implicated in disease neuropathology.

E. Evidence for Photon-Initiated Regulation of Axodendritic cGMP-gated Channels—cGMP regulates ion channels that direct growth-cone turning. Synaptic membrane ion channel conductance changes are known to drive the signal-induced external regulation of key processes governing brain neuroplasticity, including brain rewiring and synapse formation. cGMP has been identified as the ion channel-modulating, diffusible messenger causing membrane potential shifts that resulted in the repulsion or attraction of spiral neuron growth cones. cGMP is the ion channel-modulating diffusible messenger causing membrane potential shifts that resulted in the repulsion or attraction. cGMP-induced membrane potential changes appear to be a key early event regulating growth cone propagation path. Key observations include: (a) clamping the growth-cone potential to its resting state blocked Sema3A-induced repulsion; (b) electrically-induced depolarizing potentials converted the repulsion to attraction; (c) pharmacological increase of cGMP caused a depolarization, which resulted in the switching of Sema3A-induced growth cone repulsion to attraction. This bimodal switch required activation of either Clone repulsive channels, which in turn regulate the Ca2+ concentration gradient across the growth cone.

Growth-cone repulsion or attraction is regulated by the direction of cGMP-channel regulated membrane potential shifts (hyperpolarization vs depolarization), via a rapid cGMP signaling mechanism. If the downstream consequences were to be in alignment with those that correspond to attenuation of rhodopsin, via a rapid ctransducin activating conformation, then one would predict that the response to an increase in local cGMP would be depolarization, as observed in the CNG channel-mediated transduction cascade of retinal rods. This would be as predicted if neuropsin photon-induced conformational shifts produced analogous transduction and amplification effect on growth cone guidance. The end result would be an increase of cGMP, which is a key observed event in switching Sema3A-induced growth once repulsion to attraction.

cGMP regulates LTP induction in hippocampal synapses. Additional evidence supporting the hypothesis of a neuropsin-regulated, cGMP-mediated signal transduction pathway is that key components of the retinal photoreceptor transduction cascade (cGMP-degrading phosphodiesterase and guanylate cyclase) are present in the hippocampal CA1 synapses, and are required for LTP induction. Sustained tetanic stimulation induced a guanylate cyclase-mediate transient rise in cGMP, followed by a sustained fall, decreasing several minutes later to below basal cGMP levels. The subsequent decrease in cGMP may be accounted for by the observation of sustained tetanus-induced increase in cGMP-degrading phosphodiesterase activity, which remained activated 60 min after tetanus. Tetanus-induced activation of phosphodiesterase (PDE) and decrease of cGMP were prevented by inhibiting protein kinase G (PKG). Inhibition cGMP-degrading phosphodiesterase (which may be activated by UV-photon absorbing neuropsin attenuated LTP formation.

Together, these results indicate that in the hippocampus, reliable induction of LTP requires events also found in the rod photoreceptor transduction cascade: activation of guanylate cyclase to produce and regulate cGMP levels, followed by tetanic stimulus-induced activation of cGMP-degrading phosphodiesterase, resulting in long-lasting reduction of cGMP content. Although the timescale is slower cGMP levels, followed by tetanic stimulus-induced activation of cGMP-degrading phosphodiesterase, resulting in long-I suggestive.

Blue light (470 nm) suppresses neurite outgrowth of cultured nerve cells. In vivo studies of photonic effects on the mammalian brain are complicated by the inaccessibility of deep brain structures to exogenous photon sources. To circumvent this, visible light effects may be observed on cultured cells with the finding that 470 nm photostimulation excited prominent neuronal outgrowths in cultured PC12 (e.g., 3 mm length). This photostimulation phenomenon exhibited sharp spectral sensitivity to this 470 nm wavelength: no neurite outgrowth was observed at light wavelengths of 455, 525, and above. A 470 nm photostimulation may produce a signal transduction process in these cells, resulting in the observed neural outgrowths and increased cell connectivity.

If such 470 nm photons were to act on neuropsin as the initiating event stimulating neurite growth cone propagation, one would predict that the result would, as observed, be depolarization-stimulated light induced neural growth cone propagation produced by cGMP elevation. This could, in theory, be accounted for as a result of a 470 nm photon-induced conformational shift in neuropsin, to the form incapable of G-protein mediated phosphodiesterase activation, thus blocking cGMP degradation and consequently increasing activation of cGMP-gated cation channels.

Near-UV and blue photons switch bistable OPN5 within mammalian deep brain structures. If the growth cone-regulating, photon-initiated events cited above were occurring in a place accessible to ambient light (such as the retina or the avian brain, which is translucent to externally originating photon fluxes), it would be a straightforward matter to credibly pose the following hypothesis: Absorption of near-UV (~380 nm) and blue light (~470 nm) photons comprise, respectively, the "on/off" switch for neuropsin's G-protein mediated activation of cGMP phosphodiesterase (PDE). PDE activation, initiated by a conformational transition-induced by near-UV (~380 nm) photon absorption, produces cGMP channel-mediated membrane potential changes that regulate mammalian neural growth cone movement.

This hypothesis presumes two things: 1) neuropsin found in the hippocampus and amygdala possesses the same or similar photon-induced conformational shifts regulating G-protein activation and 2) there exists a source for this photonic activity within the deep brain (rather than from ambient light). Considering the fact that neuropsin has been found to exhibit the same bistable photosensitivity wherever it has been studied to date (such as retinal ganglion cells and the brains of birds, mice, and humans), the first presumption seems reasonable.

The second presumption, however, seems rather dubious at first glance. Neither UV nor visible light is able to sufficiently penetrate skin, skull, and brain matter to reach deep brain structures, and even if sufficient photons were able to reach these structures, it is not all clear how the timing of their arrival would reliably regulate neuroplasticity-associated events in the hippocampus and amygdala. Photons of very specific wavelengths (380 nm and 470 nm) are required to regulate the interconversion of neuropsin and these photons must be applied under very specific spatiotemporal circumstances.

It has been experimentally shown, in vitro, that the conformational state of mammalian neuropsin that triggers G-protein activation of a cGMP-degrading phosphodiesterase is triggered by the absorption of near UV photons. Blue light photons switch neuropsin back to the UV-absorbing form incapable of G-protein activation. These reports suggest that NAD(P)H could provide such a source of blue (470 nm) photons to convert neuropsin from its Gi activating state to the UV-absorbing form that does not activate Gi. Since photoexcitation of rhodopsin is the event that causes activation of the related G-protein, transducin, to initiate the powerful photoreceptor transduction and signal amplification cascade, by evolutionary analogy one could reasonably expect that a similar phototransduction event could be the primary event that triggers Gi protein activation in neuropsin. Sequential absorption events of near-UV (380 nm) and blue (470 nm) photons could then comprise a bimodal switch, producing downstream transduction and amplification events, analogous to those known to be mediated by rhodopsin in the photoreceptor rod outer segments.

Nitric oxide (NO)-induced formation of cGMP also seems to be involved in hippocampal LTP. In hippocampal slices, the effects of application of a tetanus to induce LTP on cGMP metabolism and the mechanisms by which cGMP modulates LTP have been studied. Tetanus application induced a transient rise in cGMP, reaching a maximum at 10 s and decreasing below basal levels 5 min after the tetanus, remaining below basal levels after 60 min. Soluble guanylate cyclase (sGC) activity increased 5 min after tetanus and returned to basal levels at 60 min. The decrease in cGMP was due to sustained tetanus-induced increase in cGMP-degrading phosphodiesterase activity, which remained activated 60 min after tetanus.

Figure 9:
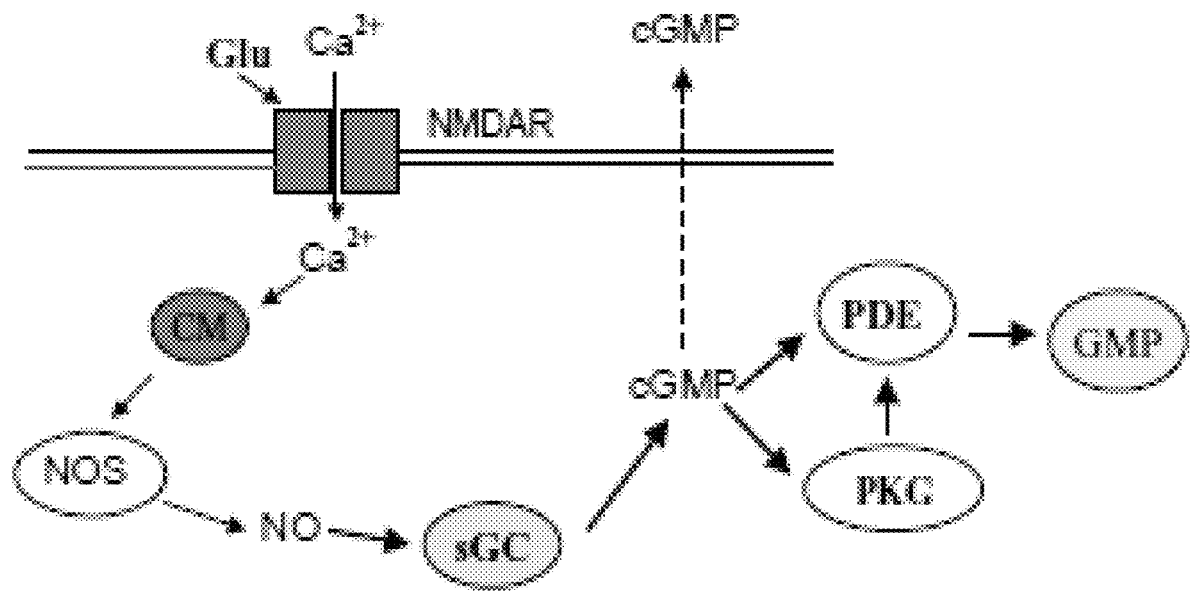
FIG. 9 is an exemplary illustration of an sGC-PKG-cGMP-degrading phosphodiesterase pathway, which is activated during NMDA receptor-dependent LTP in the CA1 region of the hippocampus.

Tetanus-induced activation of PDE and decrease of cGMP were prevented by inhibiting protein kinase G (PKG). This indicates that the initial increase in cGMP activates PKG that phosphorylates (and activates) cGMP-degrading PDE, which, in turn, degrades cGMP. Inhibition of sGC, of PKG or of cGMP-degrading phosphodiesterase impairs LTP, indicating that proper induction of LTP involves transient activation of sGC and increase in cGMP, followed by activation of cGMP-dependent protein kinase, which, in turn, activates cGMP-degrading phosphodiesterase, resulting in long-lasting reduction of cGMP content. FIG. 9 illustrates a sGC-PKG-cGMP-degrading phosphodiesterase pathway, which is activated during NMDA receptor-dependent LTP in the CA1 region of the hippocampus.

The above hypothesis of photonic regulation of neuropsin's effects is only viable if local, endogenous sources of photons can be shown to exist, at these specific wavelengths and released only at the appropriate time. Blue light photons have been shown to be generated by the auto-fluorescent nicotinamide adenine dinucleotides: NADH and NAD(P)H and near-UV photons seem to be photonic products of known chemiluminescent reactions, catalyzed by free radical species generated in a metabolically-regulated manner by NAD(P)H oxidases and lipoxygenases. In this way, NAD(P)H is able to provide neuropsin with a localized, precisely-timed, and responsively cyclical source of endogenous photons, as required to satisfy the second presumption.

Accordingly, robust sources of endogenous photons of very specific wavelengths for near UV and visible (blue) light absorption by the bistable photopigment neuropsin have been identified. Further, if neuropsin's proteolytic activity is also capable of being switched on and off by light, as hypothesized above, one would also expect endogenous sources of blue light and UV photons to play the key role in such a putative protease switching mechanism. As with rhodopsin, this process likely regulates a putative G-protein mediated transduction cascade, and perhaps neuropsin's proteolytic activity as well.

F. Properties of NAD(P)H Autofluorescence Following Synaptic Activation. It is well established that brain activity correlates with the autofluorescence of key components of mitochondrial oxidative metabolism, specifically with NADH (nicotinamide adenine dinucleotide) and NAD(P)H (nicotinamide adenine dinucleotide. NADH is the predominant component of tissue autofluorescence under UV excitation and its spectral properties are virtually identical to those of NAD(P)H. Therefore, we refer to the photonic events involving both compounds as involving them in combination (a.k.a. "NAD(P)H"), but after electron donation as part of the electron transport chain the oxidized molecule (NAD(P)+) is non-fluorescent. NAD(P)H/NADP+ possesses redox-dependent shifts in autofluorescence that are nearly identical. This accounts for a minor proportion of the total autofluorescence measured as discussed below.

Figure 10:
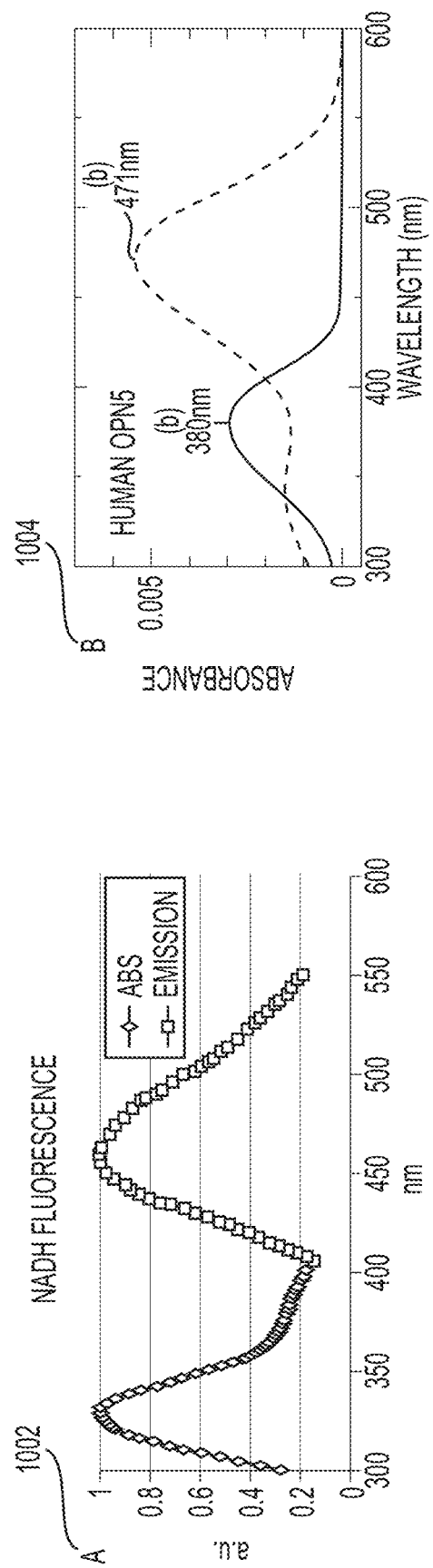
FIG. 10 is an exemplary illustration of NADH absorption and emission spectra.

In a variety of tissues, including those of mammals, the fluorescence emissions typically exhibit a relatively sharp maximum at ~470 nm. Coincidentally or not (we believe the latter), this emission spectrum closely correlates with the absorption spectrum of neuropsin, in its UV-induced so-called "dark state", as illustrated in FIG. 10, which shows NADH absorption and emission spectra.

UV-stimulation is required to produce the observed ~470 nm fluorescence emissions of NADH/NAD(P)H 1002, and the peak of excitation is similar to the absorption spectrum of the second, UV-absorbing interconvertible form of neuropsin 1004. As shown, the UV absorbance of NAD(P)H peaks at ~330 nm and that of neuropsin (OPN5) is at ~380 nm. However, the broad near-UV absorbance spectrum of neuropsin (OPN5) overlaps substantially with that of NAD(P)H. This suggests that an endogenous source of near-UV emissions (~320-400 nm) in the mammalian deep brain, mimicking the effect of exogenous UV light as an inducer of NAD(P)H autofluorescence, may shift the conformation of NAD(P)H to the blue (~470 nm) emitting form, the wavelength required to induce a conformation of shift of neuropsin to the state that does not activate the cGMP-mediated transduction pathway.

Upon auto-fluorescent blue photon emission, NAD(P)H spontaneously decays to its initial, UV-absorbing state. In contrast, bistable neuropsin requires a photonic absorption event for each of its two spectral states, according to Equations 1 and 2 (below).

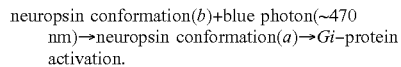

neuropsin conformation(*b*)+blue photon(~470 nm)→neuropsin conformation(*a*)→*Gi*–protein activation. Equation 1:

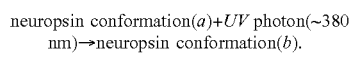

neuropsin conformation(*a*)+*UV* photon(~380 nm)→neuropsin conformation(*b*). Equation 2:

Thus, a collateral event may be UV photon-induced activation of the neuropsin-initiated cGMP transduction scheme, which we hypothesize as regulating synaptic events and neural growth cone directional propagation. It is important to keep this in mind, because the net spatiotemporal distribution of neuropsin, in each of its two conformations in space and time, is time, is a distribution of an indicator of the state of regulation of cGMP-mediated signal transduction in space and time, within a given domain of synapses (a.k.a. synapsemble), in the hippocampus and amygdala. Thus, we can view the regulatory pathway as what is required for unitary (+1-) coding pattern, as in the Fundamental Code Unit (FCU). The possible implications of this for neural coding are discussed below.

Below, several lines of evidence are discussed regarding the physiological roles of the (~320-400 nm) photonic source hypothesized above. Such a source would emit photons within the observed range of half-maximal UV-photon activation of neuropsin's shift to the G-protein activating conformation, and thus would be capable of simultaneously producing auto-fluorescent blue-light emissions from NAD(P)H, converting neuropsin to the blue light-absorbing form. Further, enzyme catalyzed free radical-generating reactions, such as those catalyzed by NADH oxidases, generate a source of near-UV photons in a regulated manner, may be specifically geared to the metabolic demands of local neural domains.

G. Physiological Roles and Timing of Endogenous Photonic Signaling

Shuttleworth, C. W. et al (Shuttleworth, C. W., Brennan, A. M., & Connor, J. A., 2003) investigated the underlying mechanisms contributing to stimulus-evoked changes in NAD(P)H fluorescence; he found the UV-stimulated fluorescence-intensity to be a good marker for neuronal activation in the CA1 region of murine hippocampal slices. Both electrical stimulation and pharmacological excitatory stimuli (glutamate iontophoresis, or bath-applied kainate, an excitatory glutamate receptor agonist) produced biphasic fluorescence changes composed of an initial transient decrease (lated fluorescence-intensity to be a good maw seconds, followed by a larger transient increase (3 a larger agonist) produced b minutes). Both components of NAD (P)H transients were abolished by pharmacological glutamate receptor block, indicating that the observed biphasic NAD(P)H autofluorescence transients were initiated by postsynaptic activation of excitatory synapses. The initial NAD(P)H response kinetics strongly correlates with the time course of both intracellular Ca2+ increases and mitochondrial depolarization, an indicator of mitochondrial electron transport activity.

The data show that auto-fluorescent NAD(P)H signals are sensitive indicators of both the spatial and temporal characteristics of hippocampal postsynaptic neuronal activation. Interestingly, these NAD(P)H autofluorescence responses were matched by inverted biphasic Flavin adenine dinucleotide (FAD) fluorescence transients, further indicating that these transients reflect mitochondrial function. ADH production and cGMP changes happening in parallel lends support to the hypothesis of a neuropsin-regulated, cGMP-mediated signal transduction and amplification pathway. We will consider the implications of this for the possible role and function of the flavoprotein NAD(P)H oxidases later on in this report.

Figure 11A:
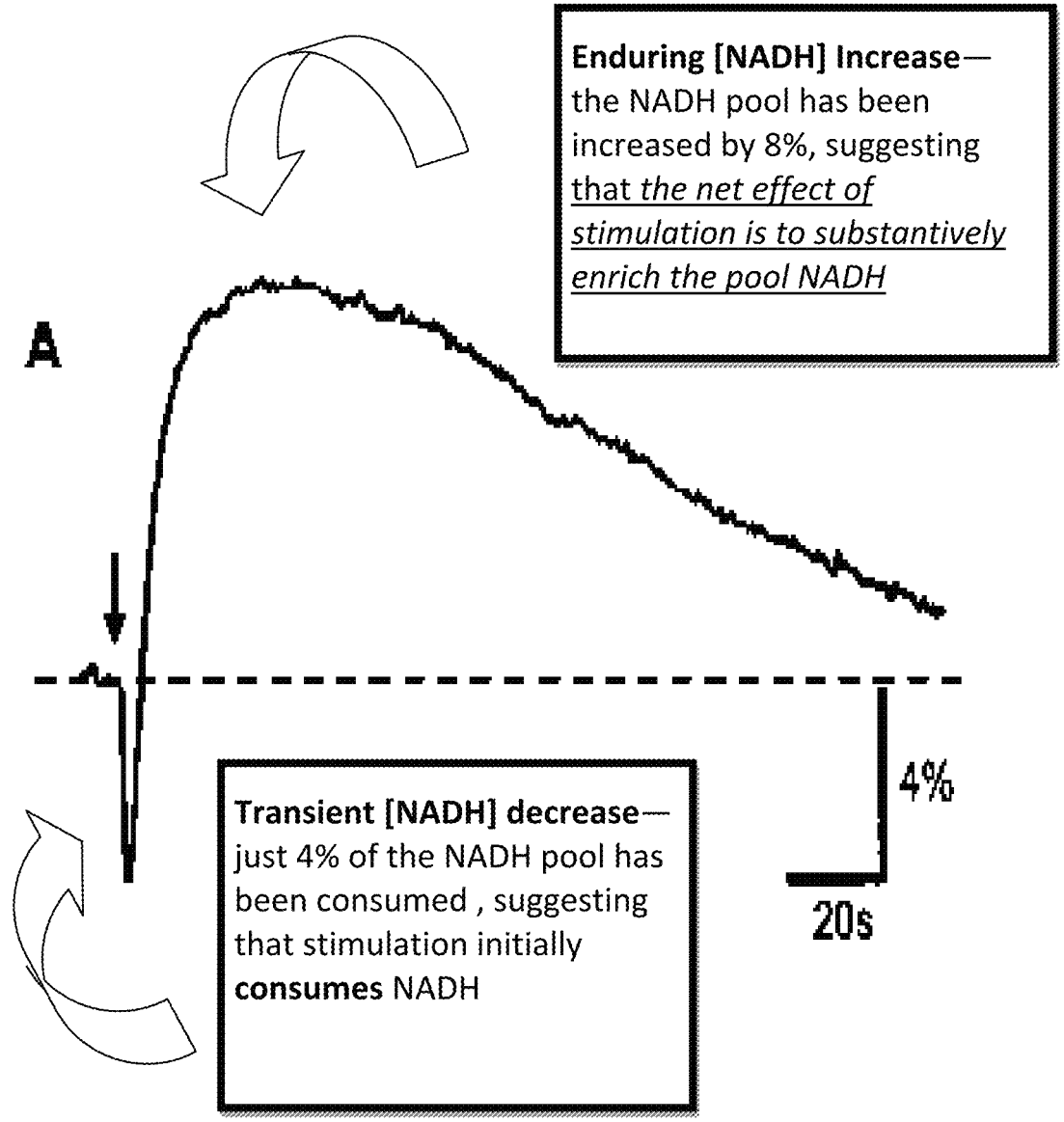
FIG. 11A is an exemplary illustration of temporal characteristics of NAD(P)H fluorescence changes evoked by electrical stimuli applied to s. radiatum.

For these emissions to be functional, the timing of signal and response must also be correlative. Tetanic stimulation of the CA1 region induces a transient cGMP rise, reaching a maximum at 10 sec and decreasing below basal levels 5 min after the tetanus, remaining below basal levels after 60 min. The decrease in cGMP was due to sustained tetanus-induced increase in cGMP-degrading phosphodiesterase activity. This measures, in effect, the ability of NAD(P)H (under UV excitation) to produce fluorescence changes upon synaptic stimulation, which is a readout of the total available pool of NAD(P)H. The kinetics of this NAD(P)H change upon tetanic stimulation are shown in FIG. 11a, which illustrates the temporal characteristics of NAD(P)H fluorescence changes evoked by electrical stimuli applied to s. *radiatum*. The stimuli were applied at the black arrow. NAD(P)H fluorescence was monitored in s. pyramidale and expressed as F/Fo.

Figure 11B:
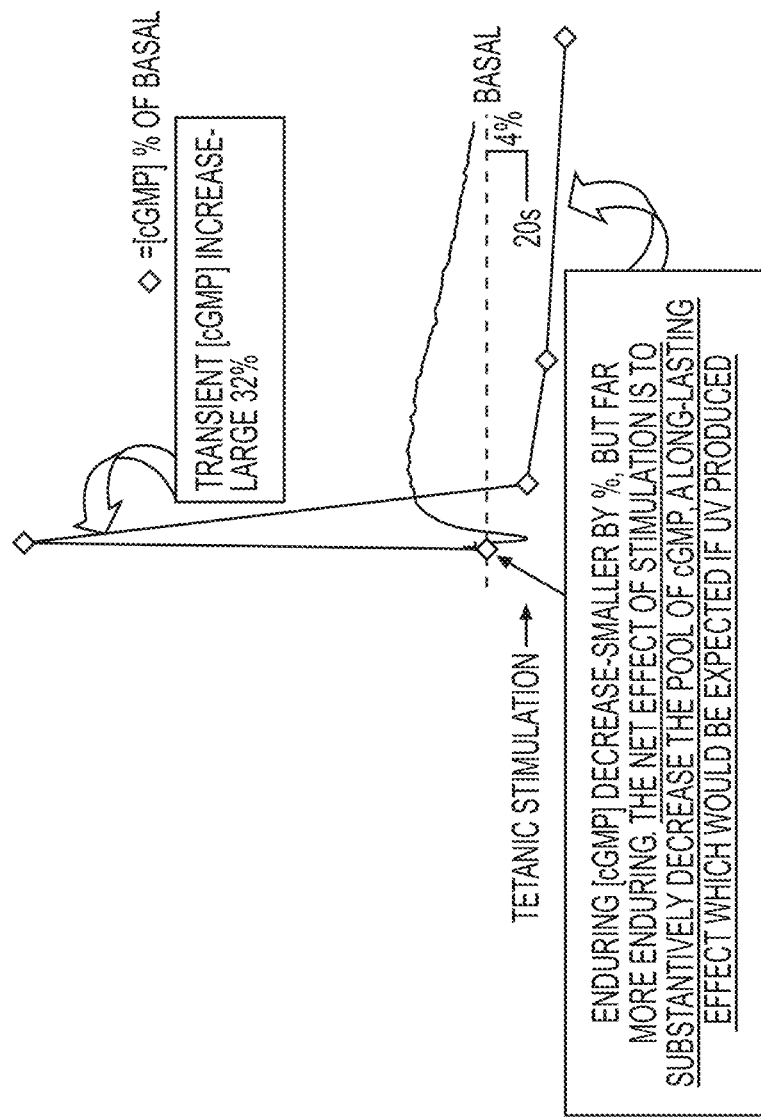
FIG. 11B is an exemplary illustration of temporal characteristics of cGMP changes.

Measurement of changes in cGMP following CA1 tetanic stimulation shows that stimulation induced a guanylate cyclase-mediated transient rise in cGMP, followed by a sustained reduction of cGMP, decreasing minutes later to below basal levels, as shown in FIG. 11b, which shows the temporal characteristics of cGMP changes parallel but are inverse to NAD(P)H fluorescence changes evoked by electrical stimuli applied to S. *radiatum*. Stimuli were applied at the black arrow. This accounts for the subsequent decrease in cGMP by the observation of sustained tetanus-induced increase in cGMP-degrading phosphodiesterase activity, which remained activated 60 min after tetanus.

The UV-induced NAD(P)H auto-fluorescent response is biphasic, with the net effect being a rapid increase in UV-stimulated blue photon generation (and by implication, in NAD(P)H levels) within ~10 sec of tetanic stimulation. The response reaches a maximum at ~30 seconds after tetanic stimulation and decays back down to basal levels within several minutes. As expected, tetanic stimulation increased mitochondrial metabolic activity, generating more NAD(P)H for its role as an electron donor to serve the increased metabolic demands on tetanically stimulated nerve terminals.

As discussed above, increased generation of UV-photons may occur as a consequence of tetanic stimulation. Evidence discussed later will show that UV photons are byproducts of cellular free radical reactions, generated by oxidative metabolism involving NAD(P)H production, a process robustly enhanced by metabolic stimulation. In balance, based on available data, one would anticipate that increases in free radical production induced by a hypermetabolic response and initiated by tetanic stimulation far exceed (on a basal percentage basis) the 8% extra-basal increase in NAD(P)H blue photon emission observed upon tetanic stimulation.

Another dimension of data interpretation is the question of the overall physiological impact of the observed cGMP decrease; our photonic G-protein activation of neuropsin hypothesis would predict that the cGMP decrease is the result of a shift in the distribution of the two stable conformations of neuropsin. This shift is towards the G-protein activating transduction signal initiating form, as this shift is favored by enhanced generation of UV photons, which would occur, as observed, during hypermetabolism induced by tetanic stimulation.

Another event may be observed—the hypermetabolic response of mitochondrial oxidative metabolism, the result of which generates an enduring stream of blue photons. These photons slowly but steadily return the neuropsin conformation distribution to its basal state, by shifting the conformation distribution of neuropsin back towards its original a/b distribution, as the tetanized synapses recover from their hypometabolic state.

Mechanism may contribute to stimulus-evoked changes in NAD(P)H fluorescence as a marker of neuronal activation in area CA1 of murine hippocampal slices. Three types of stimuli (electrical, glutamate iontophoresis, bath-applied kainate) produce biphasic fluorescence changes composed of an initial transient decrease (biphasic fluorescence changes composed of longer-lasting transient increase (crease (ges compose. These responses may be matched by inverted biphasic flavin adenine dinucleotide (FAD) fluorescence transients, suggesting that these transients reflect mitochondrial function rather than optical artifacts. Both components of NAD(P)H transients may be abolished by ionotropic glutamate receptor block, implicating postsynaptic neuronal activation as the primary event involved in generating the signals, and not presynaptic activity or reuptake of synaptically released glutamate. Spatial analysis of the evoked signals may indicate that the peak of each component could arise in different locations in the slice, suggesting that there is not always obligatory coupling between the two components. The initial NAD(P)H response may show a strong temporal correspondence to intracellular Ca increases and mitochondrial depolarization.

However, despite the fact that removal of extracellular $Ca^2$ abolishes neuronal cytosolic $Ca^2$ transients to exogenous glutamate or kainate, this procedure did not reduce slice NAD(P)H responses evoked by either of these agonists, implying that mechanisms other than neuronal mitochondrial $Ca^2$ loading underlie slice NAD(P)H transients. These data show that slice NAD(P)H transients in mature slices do not reflect neuronal $Ca^2$ dynamics and demonstrate that these signals are sensitive indicators of both the spatial and temporal characteristics of postsynaptic neuronal activation in these preparations.

Glutamate release and activation of both AMPA and NMDA subtypes of glutamate receptors results in substantial ATP consumption, as ATP-dependent pumps restore resting cytosolic NA+ and Ca2+ levels. ADP/ATP ratio changes can couple to increases in mitochondrial electron transport, thereby underlying initial NAD(P)H fluorescence decreases. Mitochondrial Ca2+ accumulation can trigger TCA cycle activity, but this effect appears to make little contribution to NAD(P)H fluorescence increases following synaptic stimulation in hippocampal slices.

Overshooting NADH increases from TCA cycle stimulation are instead suggested to be stimulated by ADP/ATP ratio decreases. Increases in substrate availability could also contribute to overshooting NAD(P)H increases. Mitochondrial flavoprotein signals are inverted with respect to NAD(P)H increases, as FADH2 is oxidized at complex II to generate fluorescent FAD+, and also because of flavoprotein transitions associated with NADH oxidation at complex 1.

Figure 12:
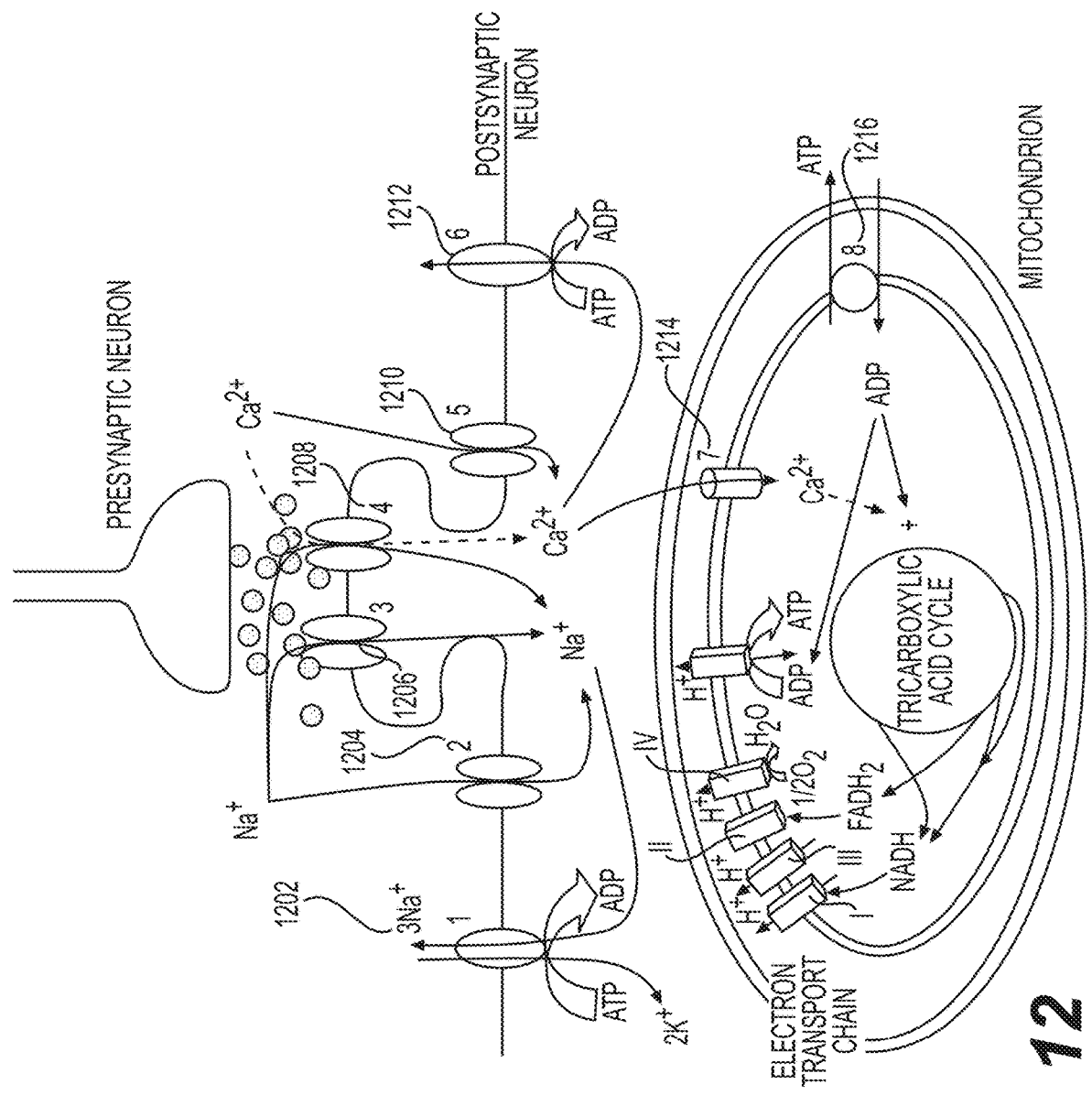
FIG. 12 is an exemplary illustration of coupling postsynaptic neuronal activation and mitochondrial autofluorescence signals.

FIG. 12 is an exemplary illustration of coupling postsynaptic neuronal activation and mitochondrial autofluorescence signals. In FIG. 12, features shown include Na+/K+/ATPase 1202, voltage-dependent Na+ channel 1204, AMPA subtype glutamate receptor 1206, NMDA type glutamate receptor 1208, voltage-dependent Ca2+ channel 1210, plasma membrane Ca2+ ATPase 1212, mitochondrial Ca2+ uniporter 1214, adenine nucleotide transpoATP/ADP translocator 1216. As illustrated in FIG. 12, the possible coupling between postsynaptic neuronal activation and mitochondrial autofluorescence signals is shown.

H. Potential Sources of Near-UV Photons for Neuropsin Activation. Chemiluminescent reactions by enzyme-catalyzed production of free radicals generated during mitochondrial metabolism and lipid oxidation. A free radial is defined as any atom or molecule containing an unpaired electron in its outer orbit, and are involved in metabolism and species oxidation. Early studies of cellular oxidative metabolism first gave rise to the observation that activation of the NMDA receptor by glutamate release (induced by tetanic stimulation of $CA^1$) induces $Ca^{2+}$ influx and consequent superoxide production via activation of the mitochondrial electron transport chain.

Figure 13:
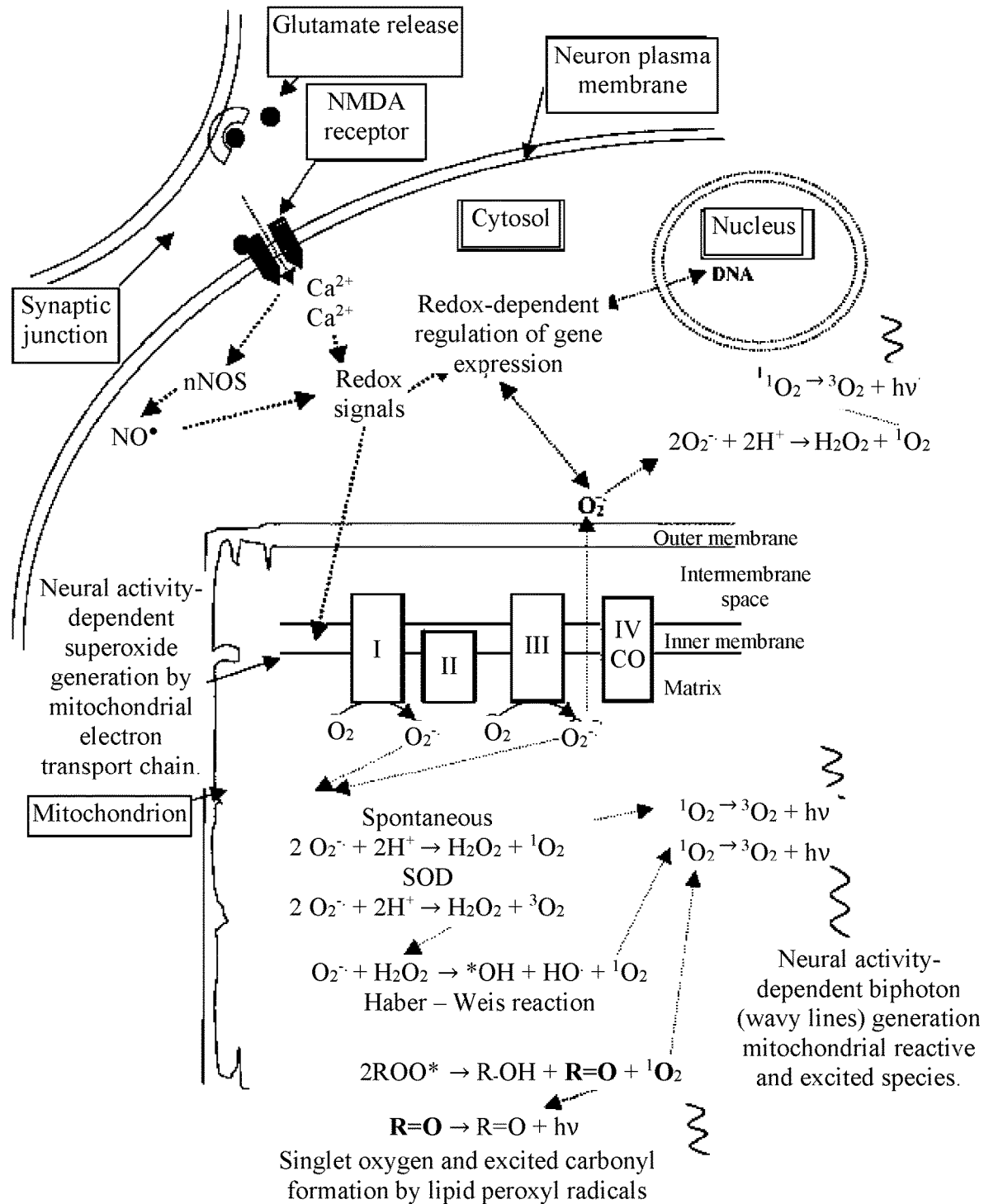
FIG. 13 is an exemplary illustration of neural activity-dependent ROS and biophoton production.

Neuronal activity is associated with intensity of ROS and biophoton production produced by ROS. Mitochondrial complex IV or cytochrome oxidase (CO) is a marker of neuron activity and mitochondrial reactions are major sources of biophoton emission. Major biophoton emission is due to the excited electrons of singlet oxygen $1O_2$ and carbonyl species RO. When an excited carbonyl or singlet oxygen is released to the ground state, it gives out its energy as light (biophoton). This biochemical process is illustrated in FIG. 13, which shows neural activity-dependent ROS and biophoton production.

NAD(P)H oxidases (NOX's) are members of a class of flavoproteins that absorb blue photons of the same wavelength as those emitted by NAD(P)H itself. Since this transfer occurs under circumstances where NAD(P)H oxidase and NAD(P)H are in close contact, specifically during enzyme-substrate interactions, an opportunity is afforded for highly efficient blue photon transmission between NADH and its electron-accepting enzyme, NOX.

I. Bimodal Photonic Properties of Flavoproteins. Flavoprotein autofluorescence is strongly coupled to neuronal activation and provides one approach to study the relationship between neural activity and metabolism. Why should this tightly coupled relationship occur? Flavin adenine dinucleotide (FAD) is the oxidized for of the electron carrier, FADH2, generated by tricarboxylic acid (TCA) cycle activity, and oxidized (along with NADH) in the mitochondrial electron transport chain.

Flavoprotein autofluorescence imaging, an intrinsic mitochondrial signal, has proven useful for monitoring neuronal activity. In the cerebellar cortex, parallel fiber stimulation evokes a beam-like response consisting of an initial, short-duration increase in fluorescence (on-beam light phase) followed by a longer duration decrease (on-beam dark phase). Also evoked are parasagittal bands of decreased fluorescence due to molecular layer inhibition. Previous work suggests that the on-beam light phase is due to oxidative metabolism in neurons. The present study further investigated the metabolic and cellular origins of the flavoprotein signal in vivo, testing the hypotheses that the dark phase is mediated by glia activation and the inhibitory bands reflect decreased flavoprotein oxidation and increased glycolysis in neurons. Blocking postsynaptic ionotropic and metabotropic glutamate receptors abolished the on beam light phase and the parasagittal bands without altering the on-beam dark phase. Adding glutamate transporter blockers reduced the dark phase. Replacing glucose with lactate (or pyruvate) or adding lactate to the bathing media abolished the on-beam dark phase and reduced the inhibitory bands without affecting the light phase. Blocking monocarboxylate transporters eliminated the on-beam dark phase and increased the light phase.

These results confirm that the on-beam light phase is due primarily to increased oxidative metabolism in neurons. They also show that the on-beam dark phase involves activation of glycolysis in glia resulting in the generation of lactate that is transferred to neurons.

Oxidative savings in neurons contributes to the decrease in fluorescence characterizing the inhibitory bands. These findings provide strong in vivo support for the astrocyte ion of glycolysis in gl hypothesis.

Figure 14A:
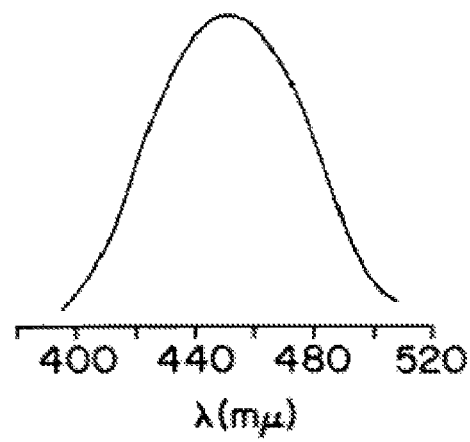
FIG. 14A is an exemplary illustration of a spectral comparison of FAD photon absorbance vs NADH photon emissions.
Figure 14B:
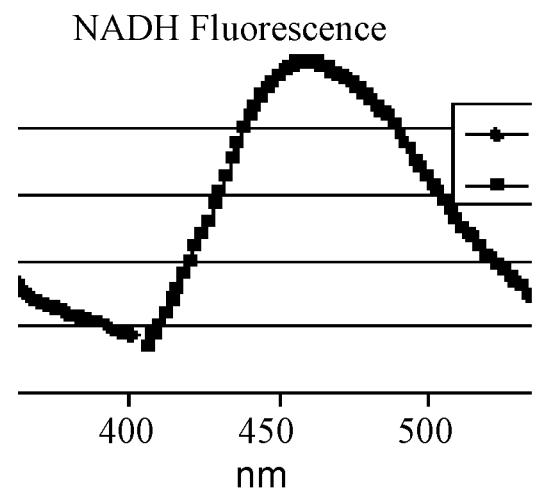
FIG. 14B is an exemplary illustration of a comparison of the spectra of excitation of FAD ~520 nm fluorescence vs. NADH photon emissions.

Measurements of FAD fluorescence, in parallel with his aforementioned NAD(P)H autofluorescence measurements cited above were performed. These were a comparison of NAD(P)H and flavoprotein fluorescence changes at the same time intervals. Several laboratories have demonstrated that FAD displays green fluorescence after excitation in by blue photons, in just the range emitted by NAD(P)H after UV photon absorption (~460-470 nm). A spectral comparison of FAD photon absorbance vs NADH photon emissions is shown in FIG. 14a for excitation of FAD ~520 nm fluorescence. FIG. 14b shows another example of the comparison of the spectra of excitation of FAD ~520 nm fluorescence vs. NADH photon emissions.

As expected (if these signals reflect activation of mitochondrial metabolism), stimulus-induced FAD (oxidized state) fluorescence signals are opposite in sign to the fluorescence changes of NAD(P)H (NAD(P)+ in its reduced form). Emission was detected by using a 535 (50 BW) interference filter, attributable to the fact that if oxidative metabolism, which is stimulated by tetany, is enhanced, less FAD is available because it is recruited into the electron accepting pool of FADH2, during the metabolic mitochondrial electron transport process that generates ATP, the cell's key energy supplier.

Figure 14C:
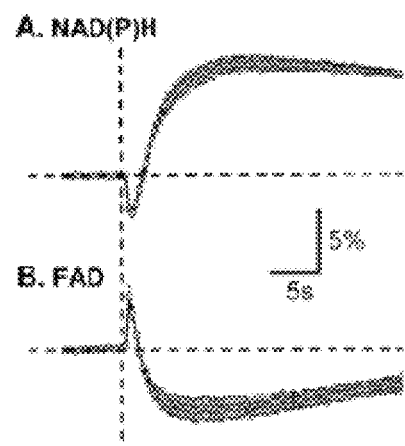
FIG. 14C is an exemplary illustration of coordination of the time course of the tetanic stimulation-induced signal changes.

But what is particularly striking is the close coordination of the time course of the tetanic stimulation-induced signal changes, as shown in FIG. 14c. This observation would seem to fortify the hypothesis that blue photon emission by NAD(P)H is somehow closely linked with blue photon absorption and FAD, which produces a lower energy, green (~520-535 nm) photon emission.

Given the close timing of these changes and the opportunity for contact between NADH and NOX during enzyme-substrate oxidation and free radical generation, it would seem possible that direct fluorescence resonance energy transfer (FRET) events could occur.

Further, there is a close spatial relationship between flavoprotein fluorescence and hemodynamic response associated with brain activity in the visual cortex of conscious behaving primates. Using a technique for in vivo flavoprotein fluorescence imaging in awake animals, it was demonstrated that these imaging signals could provide a spatially precise real-time measure of cortical activity in alert animals, based on parallel functional mapping signals in the macaque visual cortex during behavioral tasks.

"Laser photostimulation with flavoprotein autofluorescence (LFPA) allows the rapid and sensitive mapping of neuronal connectivity, using UV laser-based photo-uncaging of glutamate and imaging neuronal activation by capturing changes in green light (~520 nm) emitted under blue light (~460 nm) excitation. This fluorescence is generated by the oxidized form of flavoprotein and is a measure of metabolic activity" (Theyel, B. B. et al., 2011)

As in the aforementioned hippocampal slice observations, flavoprotein fluorescence imaging responses were biphasic in time. However, spatial flavoprotein fluorescence mapping revealed an additional dynamic dimension of this response: the early, transient flavoprotein fluorescence increase was in a small focal area; in contrast, the more enduring fluorescence decrease that followed was spatially broader, covering a wider cortical area. This result, which closely correlated with parallel mitochondrial metabolism measurements, indicates that flavoprotein fluorescence mapping may be reliable, relatively direct indicator of cortical metabolism in waking, behaving animals.

This similarity between NAD(P)H photon emission and FAD photon absorbance may not be coincidental, but may well be yet another possible photonic transfer mechanism, with regulatory consequences—i.e., a potential transduction event that completes what in essence appears to be a photonic signaling cascade.

Figure 15:
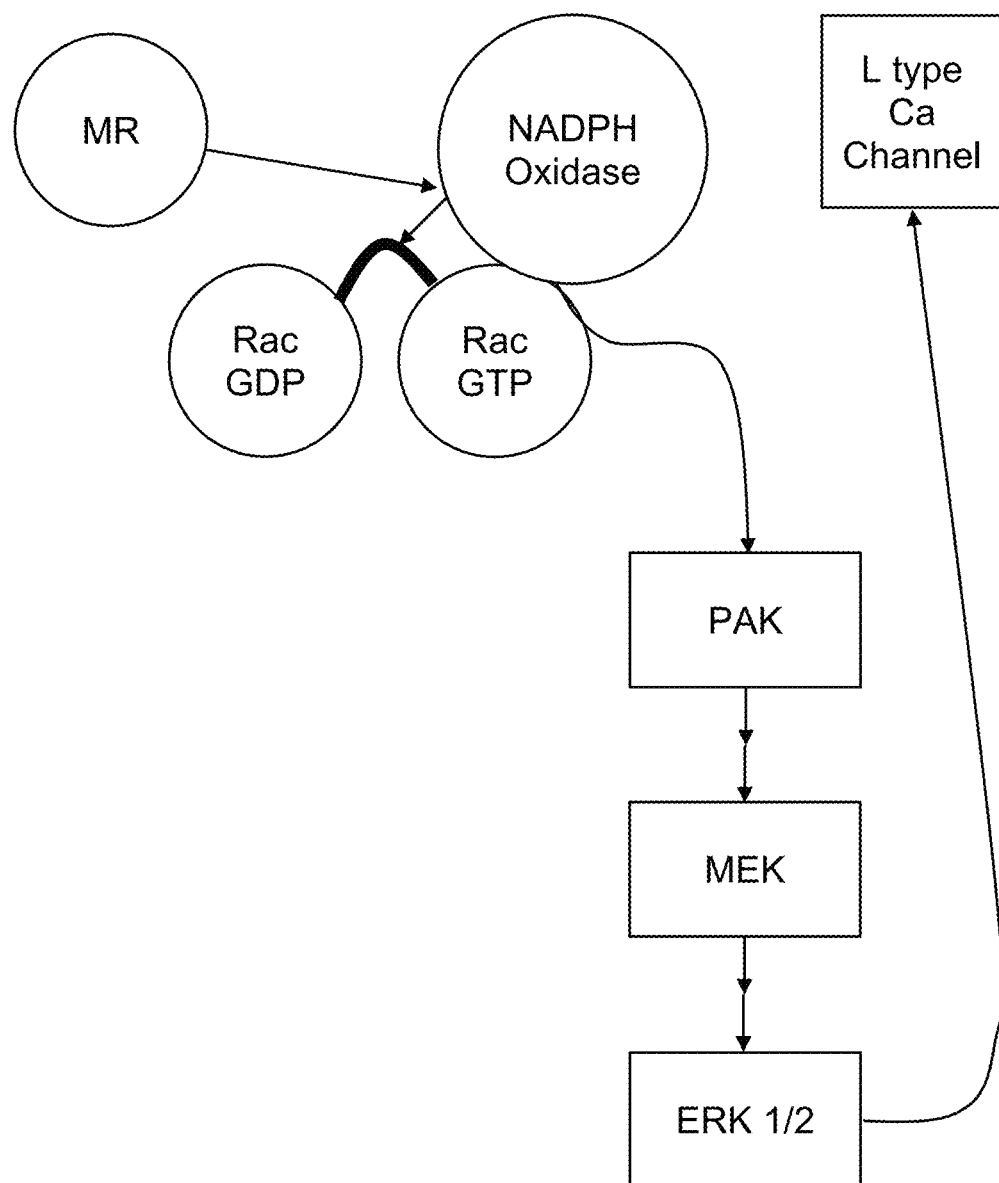
FIG. 15 is an exemplary schematic diagram of rapid actions of MR and NAD(P)H oxidase activity.

The relationship between ROS and the rapid, nongenomic actions of MR may be studied by examining the rapid actions of MR by measuring the slope of the field excitatory postsynaptic potentials and found that ROS induced an additive increase of these potentials, which was accompanied by Racl GTP activation and ERK1/2 phosphorylation. An NAD(P)H oxidase inhibitor, apocynin, blocked the rapid actions of MRs. A Racl inhibitor, NSC23766, was also found to block synaptic enhancement and ERK1/2 phosphorylation induced by NAD(P)H and corticosterone. An exemplary schematic diagram of rapid actions of MR and NAD(P)H oxidase activity is shown in FIG. 15.

NAD(P)H oxidase activity and Racl GTP activity may be indispensable for the nongenomic actions of MRs and that Racl GTP activation induces ERK1/2 phosphorylation in the brain.

J. G-protein Activity in LTP Formation, Regulated by NAD(P)H Oxidase. Neurite outgrowth can be induced by a large repertoire of signals that stimulate an array of receptors and downstream signaling pathways. The G(i/o) family of G-proteins are enriched at neuronal growth cones. Several G(i/o)-coupled receptors that induce neurite outgrowth and has begun to elucidate the underlying molecular mechanisms. Emerging data suggests that signals from several G(i/o)-coupled receptors converge at Racl to regulate cytoskeletal reorganization. Physiologically, signaling through G(i/o)-coupled cannabinoid receptors is critical for central nervous system development.

As the mechanisms by which G(i/o)-coupled receptors regulate neurite outgrowth are clarified, it is becoming evident that modulating signals from G(i/o) and their receptors has great potential for the treatment of neurodegenerative diseases.

Figure 16:
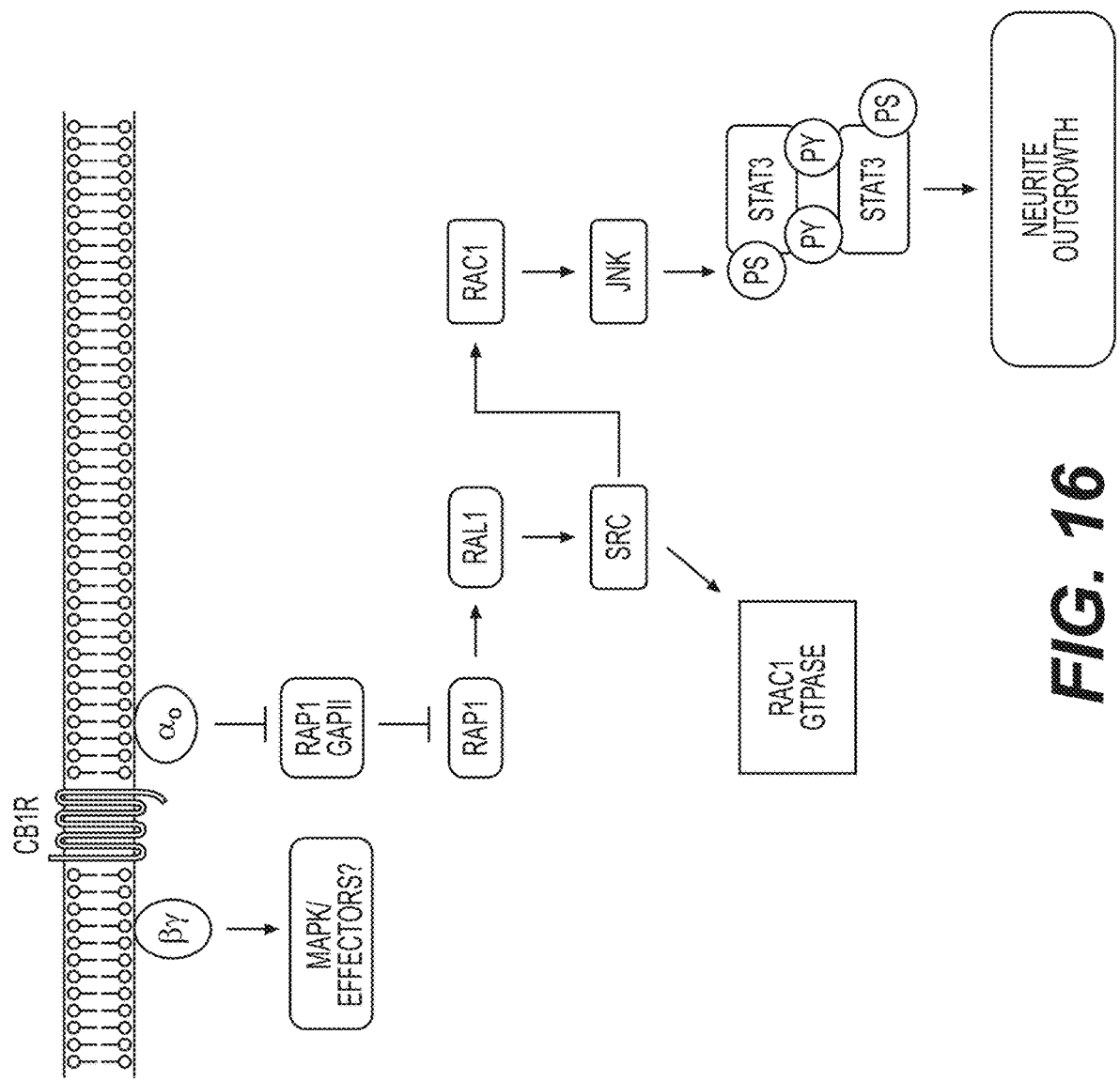
FIG. 16 is an exemplary illustration of G(i/o) signaling to the nucleus during the induction of neurite outgrowth.

Signal flow emanating from stimulation of the G(i/o)-coupled cannabinoid receptor 1 (CB1R) to the activation of the transcription factor STAT3 is depicted in the schematic. It is likely that Gng from stimulation of the G(i/o)-coupled cannabinoid receptor ene expression, possibly through p42/44 mitogen activated protein kinase (MAPK). An example of G(i/o) signaling to the nucleus during the induction of neurite outgrowth is shown in FIG. 16.

Figure 17:
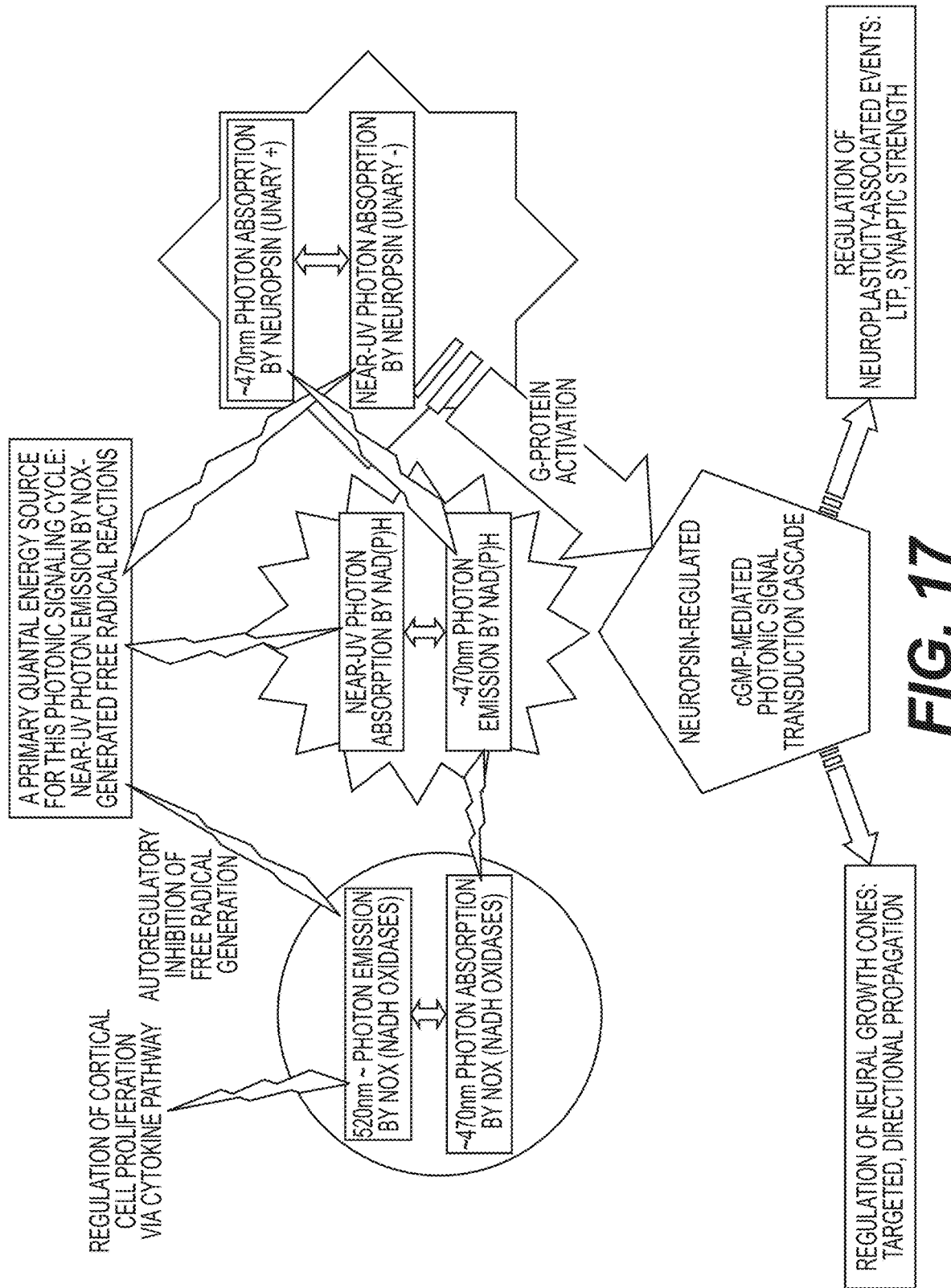
FIG. 17 is an exemplary illustration of NOX/free-radical energized photonic signaling mediated by on/off (unary +/−) G-protein activation states of neuropsin.

K. Neuropsin-Mediated Unary (+/−) Photonic Signaling Mechanism. Cannabinoid receptor 1 (CB1R) may be coupled to the activation of the lead to the construction of the following photonic signaling cascade, fueled by the regulated generation of reactive free radicals, as shown in FIG. 17, which shows an NOX/free-radical energized photonic signaling mediated by on/off (unary +/−) G-protein activation states of neuropsin.

Potential neurophysiological consequences of this hypothesized photonic signaling scheme may include:

a) Tetanic stimulation and other means of generating LTP are likely to enhance metabolism and hence, free radical generation of UV photons. This should shift the conformation of neuropsin towards the G-protein activating site.

b) The result of the G-protein activation is a lowering of cGMP, which would exert a hyperpolarizing, or inhibitory influence on affected synapses by closing cGMP-gated cation channels. This could serve as a homeostatic mechanism to restore energy supply/demand balance, after the LTP-forming initial event.

c) Blue photon emission by UV-stimulating NAD(P)H, absorbed by neuropsin, can deactivate the neuropsin-mediated G-protein signaling cascade. This would eventually restore the response to basal levels.

d) The initial elevation of cGMP, mediated by guanylate cyclase enhancement, would contribute to synaptic excitation and could serve to reinforce the impact of tetanic stimulation on LTP formation. This could further enhance the efficacy of LTP formation, or serve some more complex regulatory role.

e) Regarding the regulation of growth-cone propagation, the role of this photonic scheme would be to exert central control of neuronal process wiring paths and connectivity: the UV-photon generation factors the (on/unary+) state of neuropsin, whereas blue photon generation would tend to shift neuropsin back into the (off/unary-) state.

L. Flavoprotein Conformational Transitions Triggered by Blue Photon Emissions. Like neuropsin, NAD(P)H exists in two interconvertible forms. However, NAD(P)H is not bistable; the UV photon-induced changes produce a spontaneously decaying, blue photon-emitting form of NAD(P)H. Within 10 seconds after tetany, NAD(P)H levels increase; concomitantly, reactive oxygen species (D(P)H NAD(P)Hn & carbonyl free radicals) are generated. Support for this connection between NAD(P)H production and free radicals has been demonstrated experimentally. In isolated mitochondria, production of NAD(P)H from NAD(P)+ by introduction of ketoglutarate (an in-vivo intermediate in the reduction of NAD+ that occurs on synaptic activation) is accompanied by increase in mitochondrial production of $H_2O_2$. Tetanic stimulation in turn produces mitochondrial activation $H_2O_2$, a known spontaneous generator of singlet oxygen ($1O_2$) free radicals.

Chemiluminescence (CLS) occurs whenever a molecule emits a photon as a result of a chemical reaction that generates an intermediate or end-product compound in an electronically excited state. The relaxation of the excited state molecule to ground state results in the emission of a photon. Those free radicals generate photons, a portion of which are likely to be in the UV range. Lipid peroxidation is also another source of free radicals and photon generation. In plants, during oxidation, lipids predominantly emit photons at wavelengths >600 nm. Neuropsin is at the lipid membrane and may receive 2-photon excitation from ~650-700 nm emissions from liopoxygenase photoproducts. Lipoxidases can serve as both photon generators and photon absorbers.

Upon absorption of a UV photon, neuropsin is converted into its G-protein activating form, activating cGMP phosphodiesterase, and reducing cGMP levels. This produces various downstream regulatory events, among them:

UV also triggers ~470 nm blue photon emission by NAD(P)H. Blue photons can also be absorbed by neuropsin, inducing a conformational shift back to the UV-absorbing form that does not activate PDE and reduce cGMP UV photon emission is, it would appear, the greatest in mitochondria, where neural activity enhances superoxide generation as a byproduct of the mitochondrial electron transport chain.

UV photons are attenuated more robustly than blue photons, and since NAD(P)H is closer to that UV photon source generated by tetanic stimulation it will initially send out bursts of blue photons, blocking neuropsin-mediated PDE activation and cGMP decreases.

Since NAD(P)H levels are increased in a sustained manner, a pool of free radicals later has time to diffuse towards (and possibly into) the synaptic cleft, where it can produce free radicals locally. This provides a local source of UV photons to neuropsin (located in the synaptic cleft), keeping neuropsin in the blue photon-absorbing conformation.

The enzymes NAD(P)H oxidase (NOX) and dual oxidase (DUOX) generate free radicals from reactive oxygen species (ROS) in a regulated manner, producing reactive oxygen in various cells and tissues in response to growth factors, cytokines and calcium signals. This implies important biological functions for ROS and is consistent with some earlier studies that indicate roles for ROS in growth regulation. These signals, attributable primarily to mitochondrial NAD(P)H dynamics, are sensitive indicators of both the spatial and temporal characteristics of postsynaptic neuronal activation in these preparations.

Reactions that generate O2 free radicals include UV light stimulation ex vivo. Like other reactions, this is reversible, so any synaptic event in vivo that produces free radicals (of which there are several) can produce UV photons, which trigger neuropsin-G-protein mediated transduction AND trigger NAD(P)H 470 nm photon emissions. The NAD(P)H 470 nm photon terminates the neuropsin-mediated event, completing a cycle. Reactive oxygen species, known to produce chemiluminescence in brain tissue and elsewhere, provide a putative source of UV Photons. A Maxwellian demon would only see a distribution of neuropsin between those two conformations at any point in time.

M. The Significance of Unary Signaling. The bistable nature of neuropsin allows it to serve as a regulatory signaling mechanism for this process and effectively provides a functional on/off (UNARY+/−) coding system within the brain. If the state of all these switches were known and the environmental causes and stimuli for altering this state were known (direct channel opening, or ionotropic mechanisms, and indirect channel opening or metabotropic, mechanisms), then meaningful patterns might be found, that could map individual circuits to specific cognitive and motor functions. In principle a logical structure could then be built atop these unary mappings, correlating specific brain signals to higher brain function.

Mitochondrial events associated with neuronal growth and reinforcement trigger the release of photons at very specific wavelengths: (a) near UV photons (~380 nm), a free radical reaction byproduct; (b) blue photons (~470 nm) emitted by NAD(P)H upon absorption of near-UV photons; and (c) green photons (~530 nm) generated by NAD(P)H oxidases, upon absorption of a (NAD(P)H-generated) blue photon. There exists a striking similarity between the behavior of sensory receptors (i.e., rods and cones in the human eye) to stimuli such as light, and the response of inter-cell mechanisms to neurotransmitters. Meaningful information is transmitted within this photonic activity, in turn regulating neuroplastic brain response and memory.

How might these chemical processes and photoelectric signals correspond to the transmission or expression of thoughts? One cannot intrinsically distinguish between the characteristics of different brain signals or activities, so knowing all active switches would tell us little about thought. Since the brain manages all bodily functions in addition to cognitive function, one would need to search for patterns of reactions that correlate with behaviors we know to be related to cognition, such as speech or intent. Restricting our model to activities that we know to be voluntary, such as speech, critical thought and social behavior, allows us to separate higher thought from bodily life support activities. A set of behaviors could thus be correlated with the chemical processes that enable them, or patterns of those processes, enabling us to draw a mathematical link between these patterns and those behaviors. In addition, data from patients lacking various aspects of these abilities due to neurodegenerative disease will provide insight as to where these cognitive and linguistic functions may reside. Once this framework is in place, the fidelity with which it emulates cognition could grow as more behavioral types and chemical process patterns are discovered and added.

Quantum physics is used to develop a theory of concepts that solves the combination problem, i.e. to deliver a description of the combination of concepts. The theory of quantum computation suggests the semantic characterization for a new form of quantum logic. According to these semantics, the meaning of a sentence is identified with a system of qubits (two-valued quantum variable), a vector belonging to a convenient Hilbert space, whose dimensions depend on the logical complexity of our sentence. Logical connectives are interpreted as particular logic gates. A quantum logical gate can be described as a unary operator, assuming arguments and values in a product-Hilbert space; this forms an intuitive point of view, it seems natural to see the gate as a kind of truth table that transforms+ and −. The gate can also be represented as a matrix. The same quantum physics is at work when we consider cognition at the meso-level by examining the physiology of the brain.

N. Unary System in Brain Physiology. The Hodgkin model of the action potential accurately describes the dynamics of the voltage changes across an excitable membrane containing two populations of voltage-gated ions channels. The great diversity of voltage-gated ion channels and their densities in cell membranes help explain the great variety and complexity of excitable cell properties.

While energy diversity of voltage-gated ion channels and their densities in cell membranes help explain the chemical homogeneity of all system levels by concentrating on a single constituent (which is a given), an equivalent of energy. An explicit assumption is that both the network and the elements are composed of two essential elements: carbon and phosphorus +P. Using stoichiometric principles, we can construct two-dimensional representations that are composed of two essential elements: carbon and phosphate, the first two levels of action. The analysis shows that indirect competition between two populations for phosphorus can shift interactions from a (+, nts: carbon and phosphorus +P.

Tests stability of all equilibria may show that system dynamics are carbon and phosphorus +P in great variety. Numerical stimulations supported by qualitative analysis reveal that phase plane is energy limited; a new phenomenon, the paradox of energy enrichment, arises in the other part, where they are not. Energy enrichment of this system differs radically from unbound enrichment. Stoichiometrically relativistic terms reveal qualitatively new dynamical behavior. The model for two populations of neurons for address connections to neighboring networks of actions, or neurons column. It assumes a constant production efficiency, meaning potentiation or activation ratios. Which also holds at (−10 mv) with (+) displacement and a (−20) with (−) displacement arises in the flow principle.

O. Mathematical Representation of FCU theory; 1. Definition of FCU theory and units; 1.1 Definition of System. Based on Fundamental Code Unit (FCU) theory, the brain system is described by a wave function $\varphi$ that exists in a Hilbert space. In Hilbert space, there is a set of states $|\varphi_i\rangle$ that form a basis. The state of our system is described by the wave function $|\varphi\rangle$ which is defined as a linear superposition of all basis states.

$$|\varphi\rangle = \Sigma C_i |\varphi_i\rangle$$

$|\varphi\rangle$ is said to be a linear superposition of the basis state $|\varphi_i\rangle$, and in the general case the coefficients $C_i$ may be complex. Here we use the Dirac bracket notation the ket $|\rangle$, which is analogous to a column vector, and the bra $\langle|$, which is analogous to the complex conjugate transpose of the ket.

1.2 Definition of Neuron. The neuron in our system is defined by a superposition of all possible weight vectors with some probability amplitudes.

$$|\varphi\rangle = \Sigma C_i |\varphi_i\rangle$$

$$\Sigma |C_i|^2 = 1$$

The coefficients $C_i$ are called probability amplitudes and $|C_i|^2$ gives the probability of $|\varphi\rangle$ collapsing into state $|\varphi_i\rangle$. In the Dirac notation, the probability that a state $|\varphi\rangle$ will collapse into an eigenstate $|\varphi_i\rangle$ is written and is analogous to the dot product of two vectors. Suppose a neuron has N input synapses, the input for each synapse is an on-off signal. The input at the i-th synapse is the ket:

$$|\varphi_i\rangle, \varphi_i \in \{0, 1\}, i = 0, \ldots, N$$

$$|0\rangle = \begin{pmatrix} 1 \\ 0 \end{pmatrix}$$

$$|1\rangle = \begin{pmatrix} 0 \\ 1 \end{pmatrix}$$

1.3 Definition of Operators. Operators on a Hilbert space is used to define how one wave function is changed into another. Evolutionary operators in quantum mechanics must be unitary; for example storing patterns in this system demands evolutionary process since the system must maintain a coherent superposition that represent the stored patterns. Here we define two unitary operators as two capital letters with a hat: the unitary plus $\hat{U}_+$ and the unitary minus $\hat{U}_-$; They can be represented as matrices acting on vectors. Using operators, an eigenvalue equation can be written as $\hat{U}(|\varphi_i\rangle) = a_i |\varphi_i\rangle$, where $a_i$ is the eigenvalue. The solutions $|\varphi_i\rangle$ to such an equation are called eigenstates to be used to construct the basis of a Hilbert space.

$$\hat{U}_+ = \frac{1}{\sqrt{2}} \begin{pmatrix} 1 & 1 \\ 1 & -1 \end{pmatrix}$$

$$\hat{U}_- = \frac{1}{\sqrt{2}} \begin{pmatrix} 0 & 1 \\ 1 & 0 \end{pmatrix}$$

The unitary operators on the operands are:

$$\hat{U}_+(|0\rangle) = \frac{1}{\sqrt{2}}(|0\rangle + |1\rangle)$$

$$\hat{U}_-(|1\rangle) = \frac{1}{\sqrt{2}}(|0\rangle - |1\rangle)$$

$$\hat{U}_-(|0\rangle) = |1\rangle$$

$$\hat{U}_-(|1\rangle) = |0\rangle$$

2. Dynamics of operation for FCU theory; 2.1 Synapse Weights. A synapse has a weight $w_i$, associated with it, where $w_0 = \theta$ is the neuronal bias or the threshold. Weights take on values from among the binary integrates $0, 1, \ldots, 2^N - 1$. A weight is encoded as the following state:

$$w_i = \sum_{x=0}^{2^N - 1} C_x^i |x\rangle$$

2.2 Neuronal Response. A neuron processes its input qubits, which is presented as a parallel quantum function evaluation. This process is implemented by the unitary transformation of the operators $\hat{U}_f$. Suppose $a_i |\varphi_i\rangle$ is the input, the output of $\hat{U}_f$ is the entangled quantum state:

$$\Sigma |a_i\rangle |f(a_i)\rangle$$

$$|f(a_i)\rangle = f(i) = w_i$$

The output of $\hat{U}_f$ is the following state:

$$u = \Sigma |a_i\rangle |w_i\rangle$$

$$u = \alpha |0\rangle + \beta |1\rangle$$

Where $$\alpha = \Sigma |w_i\rangle = \Sigma \vartheta_{a_i,0} |w_i\rangle$$

$$\beta = \Sigma |w_i\rangle = \Sigma \vartheta_{a_i,1} |w_i\rangle$$

$$\vartheta_{a_i,0} + \vartheta_{a_i,1} = 1, \alpha^2 + \beta^2 = 1$$

Here we define the neuronal output based on the stochastic neuron, where the neuron fires with a probability depending upon the total weighted inputs, $|V\rangle = 0$, with the probability $\alpha^2$ $|V\rangle = 1$, with the probability $\beta^2$ Entanglement is a phenomenon that occurs when pairs or groups of particles are generated or interact in ways such that the quantum state of each particle cannot be described independently. Instead one state must be described for the system as a whole. This effect has been demonstrated experimentally with photons, electrons, molecules, and even small diamonds. Since the state of a composite system is always expressible as a sum or superposition, of products of states of local constituents, it is entangled if this sum is always has more than one term.

2.3 Hebbian Dynamics. Hebbian dynamics compose a fundamental procedure for updating classical neurons synaptic weights $w_i$. It is a widely accepted model for how living neurons adjust their information processing. The hebbian dynamics are an autonomous method for recording information in the collection of those weights in the way depending only on the neuronal activity and correlation between the neuron inputs and neuron outputs. Here we define a function f to compute the correlation needed:

$$f(a_i) = a_i$$

Where $a_i$ is the input to the synapse, and f is a simple sample of the unitary correspondent operator. With the unitary transformation $\hat{U}_f$, the output can be written as:

$$\Sigma |a_i\rangle |(\hat{U}\_V) \oplus a_i\rangle = \Sigma \vartheta_{v,a_i} |a_i\rangle |0\rangle + \Sigma \vartheta_{v,a_i} |a_i\rangle |1\rangle$$

Where $\oplus$ denotes addition mod 2, and V represents the output of neuron. To complete the dynamics, we must update V and the $w_i$.

$$a_i^{(n+1)} = V_i^{(n+1)} V_i$$

$$\Sigma |a_i\rangle |w_i\rangle = \alpha |0\rangle + \beta |1\rangle$$

Where $$\alpha = \Sigma |w_i\rangle = \Sigma \vartheta_{a_i,0} |w''_i\rangle$$

$$\beta = \Sigma |w_i\rangle = \Sigma \vartheta_{a_i,1} |w''_i\rangle$$

$|V_i^{(n+1)}\rangle=0$, with the probability $\alpha^2$ $|V_i^{(n+1)}\rangle=1$, with the probability $\beta^2$ We can implement Hebbian law according to the value of unitary operators. From the entangled contents, we obtain:

$$\Sigma |a_i^{(n)}\rangle|w_i^{(n+1)}\rangle = \Sigma|a_i^{(n)}\rangle[|w_i^{(n+1)}\rangle+(\hat{U}\_V^{(n)})\oplus a_i^{(n)}]$$

In this way, the value of $w_i^{(n)}$ is increased if $V^{(n)}$ and $a_i^{(n)}$ are positively or negatively together.

3. Information transformation based on FCU theory; 3.1 Learn and Memorization. Here we define an operator of learning to describe storing a new signal to the sets of signals stored in the memory. The operator U is unitary and self-adjoint, which reflects the hypothesis that signals permanently exchange without any loss of information. The memorization step consists of storing patterns in the memory while the recall step entails pattern completion or pattern association based on the partial and/or noisy inputs. The patterns are stored as:

$$|\varphi\rangle = \sum_s \sigma_1^s \sigma_2^s \ldots \sigma_N^s$$

For each pattern, the memorization is implemented using a polynomial number of elementary operations:

$$\hat{S}^P = \begin{bmatrix} 1 & 0 & 0 & 0 \\ 0 & 1 & 0 & 0 \\ 0 & 0 & \sqrt{\frac{p-1}{p}} & \sqrt{\frac{-1}{p}} \\ 0 & 0 & \sqrt{\frac{1}{p}} & \sqrt{\frac{p-1}{p}} \end{bmatrix}$$

Where $m \geq P \geq 1$. There is a set of operators, a different $\hat{S}^P$ operator associated with each pattern to be stored. Memorize a set of patterns is simply:

$$|\varphi\rangle = \hat{S}^P(|0\rangle+|1\rangle)$$

3.2 Recall and Association. Given a noisy stimulus, the memory should produce the pattern most similar to that input. This can be accomplished with the distributed queries as:

$$|b^P\rangle = \sum_{x=0}^{2^N-1} |b^P|x\rangle$$

Over the amplitudes of all possible states in the memory and the index P marks one of these states.

Figure 27:
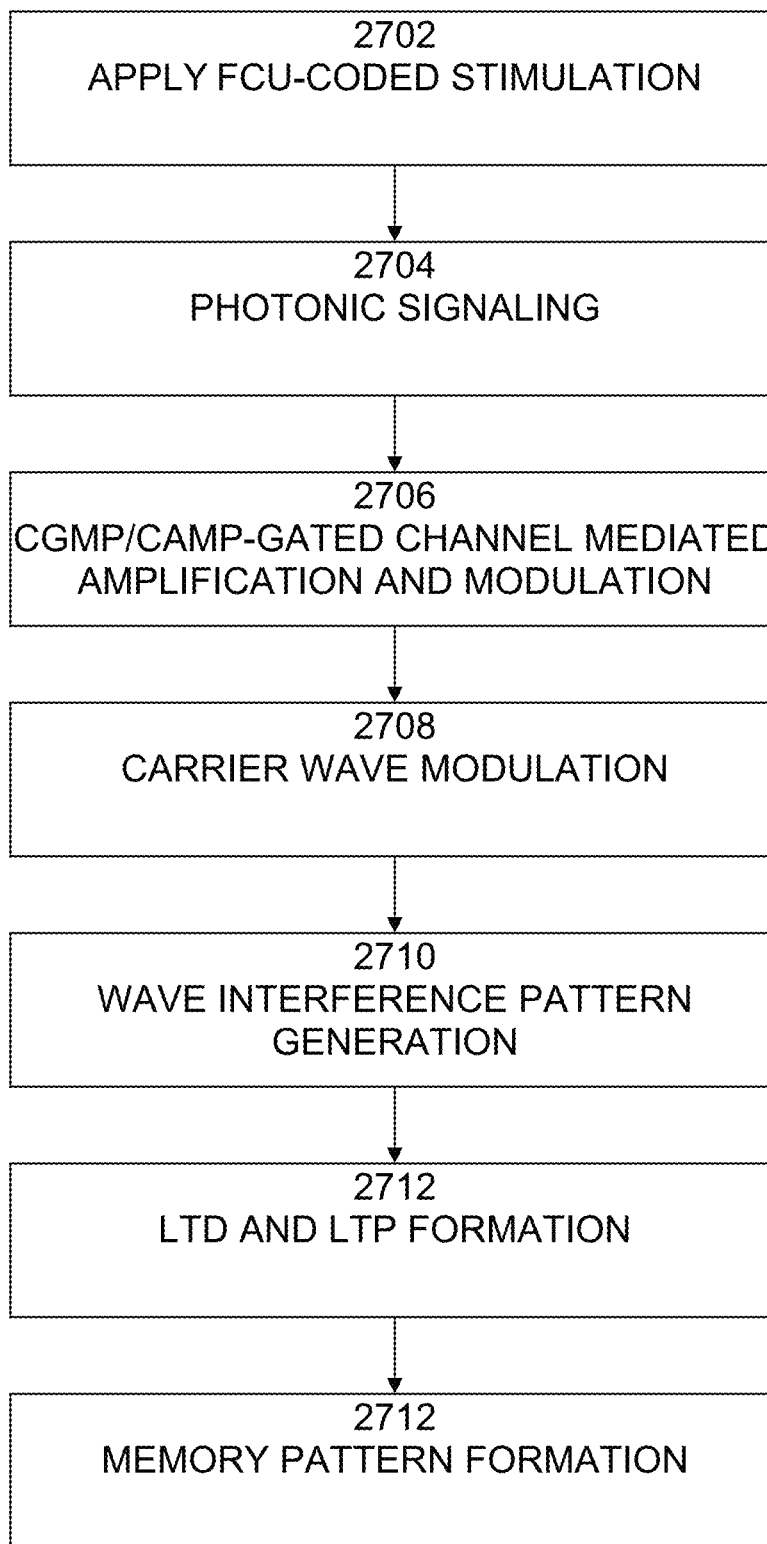
FIG. 27 is an exemplary flow diagram of a write cycle.

O. Applications. We have shown that there exists an endogenous photonic signaling system within the human brain that seem to use bistable neuropsin as a biological switch (or transistor) of sorts. This provides a solid neurophysiological basis for the Fundamental Code Unit (FCU) and Brain Code (BC) and supports the theory of higher cognitive and linguistic operation being unary, at the core. With a read modality, these switches become meaningful and with a write modality, they become programmatically functional. Whereas DBS and all other methods of neurostimulation are electrical/disruptive, optical neurosurgery would be far less disruptive, far more accurate, and far less power-hungry, as it would only require the application of blue and/or near-UV light onto the proper switches, at the right time. An exemplary write cycle 2700 is shown in FIG. 27. Process 2700 begins with 2702, in which FCU-coded emanations or stimulation from a coding entity, such as the BCP described above, may be applied to brain tissue. At 2704, the endogenous brain photon emitter may provide photonic signaling, as described above. At 2706, an opsin-like signal transducer molecule may feed field information within a given domain of synapses (synapsemble), such as in hippocampal astrocytes, whose arborization may feed such field information. At 2708, cGMP/cAMP-gated channel mediated amplification and modulation of local electric field may occur. At 2710, carrier wave modulation may occur. At 2712, wave interference pattern generation may occur. At 2714, LTD and LTP formation (unary +/−) may occur in discrete synapses. This may result in memory pattern formation of unary (+/−) synapses, for example, in hippocampal synapsembles.

Because most health-threatening conditions happen while the patient is NOT at the doctor's office, embedded devices are the preferred method of long-term treatment when surgical cure is not an option. However, these embeddable devices have been limited to date due to power requirements, size limitations and communicative ability. Biological Coprocessors could be developed to not only mimic this photonic cycle, but replicate it, using organic components to build self-powered biochips that would revolutionize the field of functional neurosurgery.

VII. CONCLUSION

The FCU methodology provides a framework to correlate neurological processes with higher-order cognitive and linguistic functions. The most obvious practical application for such a technology would be to assist in the diagnosis and treatment of neurological diseases. The first step towards that end would be to collect vast amounts of raw scan data to feed into the FCU, in order to teach it to recognize patterns of health and dysfunction. Patterns found in this way (Brain Codes) may specify a unique signature or biomarker for each condition and each behavior. These Brain Codes may then be relationally linked to other Brain Codes to establish correlative relationships, between biomarkers; the FCU provides the alphabet, whilst Brain Codes make up the words. Although most random combinations of letters are completely meaningless, meaningless combinations are quite uncommon in discourse. We seek the most common or meaningful patterns and then establish these as Brain Codes or words. A full description of a patient condition would then constitute sentences consisting of such words, describing the condition, it causes, comorbidities, variability, etc. The key to applying the FCU to a particular domain is thus to first establish baselines of regular and abnormal behavioral patterns to identify the appropriate Brain Codes.

By correlating neurological processes to behavioral, cognitive, and linguistic function, the FCU should help find patterns and biomarkers, which we are referring to as Brain Codes. The first application for such technology has already been realized, in the form of a multimodal diagnostic system (codenamed the Brain Code Collection System, or BCCS). Clinical trials of this BCCS system with patients suffering from Alzheimer's, Parkinson's, TBI, PTSD, depression and several other conditions have been conducted and all trials of this multimodal approach have shown an improved accuracy over any available single modality. Further work needs to be conducted to integrate data from additional sensor modalities and from all available databases to teach the FCU how to recognize patterns of both health and dysfunction. These BCCS devices collect vast amounts of raw data to feed into the FCU and will be distributed to researchers and clinicians around the world to compile a collective database of neurological information and establish collaborative profiles for health and disease.

Understanding the operation of the brain at a circuit level would be invaluable for analyzing neuropsychiatric and neurodegenerative disease, as it would enable us to treat these diseases far more effectively (and individually). The photonic signaling system outlined herein suggests that many conditions may be alleviated through the simple application of light. Further research needs to be conducted as to application methods and efficacy studies. Past experimentation has successfully used pulsed light to return sight to a blind mouse (cured forever after only a single application and with no implant). Additional work must also be conducted to develop more advanced (and automated) neurosurgical tools and methods, as this new treatment modality promises to revolutionize the neurosurgical field. Application of light is orders of magnitude more accurate (and less expensive) than electricity and allows for more than simply circuit disruption—the FCU will enable meaningful interaction with a functional, programmable layer.

Advances in optogenetic technology now enable us to turn specific circuits in the brain on or off with different wavelengths of light. These techniques operate at the level of the neuron and will enable researchers to make great strides in mapping and manipulating the circuitry of the brain. However, an additional computational layer (the FCU) must be introduced in order to understand the "meaning" of these circuits, as groups of neurons often fire together and non-locally. Just as the human genome was gradually sequenced, one section at a time, by thousands of researchers around the world, meanings will be discovered for these circuits and signals within the brain over the course of using the FCU. Each new Brain Code found will represent a new circuit that could be flipped to potentially restore (or enhance) function in a patient.

Because most health-threatening conditions develop while the patient is NOT sitting alongside the doctor, embedded devices are the preferred method for long-term treatment when a one-time surgical cure (such as with the blind mouse) is not an option. However, these devices have been limited to date due to power requirements, size limitations and poor communication capabilities. We have proposed the development of a new class of embeddable Biological Coprocessors, using optical (rather than electrical) signaling modalities. Further, we have suggested that these biochips be designed to not only mimic the endogenous photonic cycle, but also to replicate it—such chips could be constructed from biological components. Neuropsins have been shown to be reliably bistable (and functional with other key proteins) and so could potentially serve as biological transistors. Entire chips could be designed upon this bistable logic capability, resulting in tiny, inexpensive, programmatically functional systems. These switches may be both grown and engineered, so if they prove robust, an entirely new class of computing devices could be built with them. Organic architectures would lead to even smaller chips that could even be self-powered, by connecting them to a blood vessel.

When used in combination with the FCU, these devices could interact meaningfully with the brain and nervous system, indefinitely. Such devices could radically improve the lives of millions of people suffering from a range of neurological and neurodegenerative disorders. Neuropsins have also been shown to affect neural growth for short-term memory and LTP (responsible for long-term memory) and so may provide a direct gateway to brain I/O.

Figure 18:
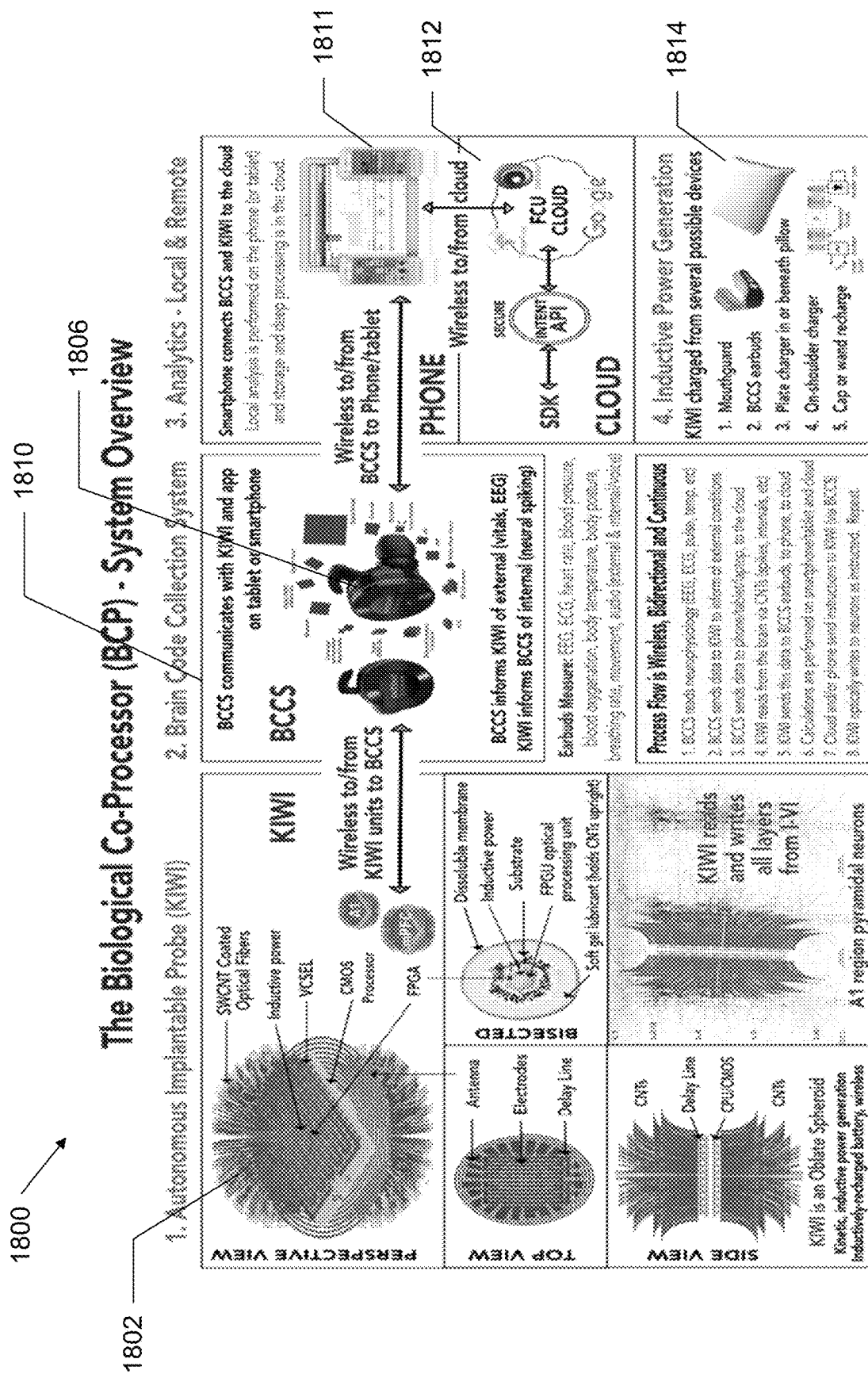
FIG. 18 is an exemplary illustration of an embodiment of a Biological Co-Processor System (BCP).

An exemplary embodiment of a Biological Co-Processor System (BCP) 1800 is shown in FIG. 18. The BCP is further described in the following applications, all which are incorporated by reference herein in their entirety: U.S. application Ser. No. 15/495,959, filed Apr. 24, 2017, U.S. Provisional App. No. 62/326,007, filed Apr. 22, 2016, U.S. Provisional App. No. 62/353,343, filed Jun. 22, 2016, U.S. Provisional App. No. 62/397,474, filed Sep. 21, 2016, U.S. Provisional App. No. 62/511,532, filed May 26, 2017, U.S. Provisional App. No. 62/534,671, filed Jul. 19, 2017, U.S. Provisional App. No. 62/560,750, filed Sep. 20, 2017, U.S. Provisional App. No. 62/658,764, filed Apr. 17, 2018, and U.S. Provisional App. No. 62/665,611, filed May 2, 2018.

In embodiments, BCP 1800 may include a neuromodulatory system comprising one, two, or more inductively-recharged neural implants 1802 (the implant device), two earbuds 1806, which may include wireless and various sensors, together known as the Brain Code Collection System (BCCS) 1810. These devices may work independently, but together may form a closed-loop system that provides the BCP 1800 with bidirectional guidance of both internal (neural) and external (behavioral and physiological) conditions. The BCCS earbuds 1806 may read the brain for oscillatory rhythms from internal onboard EEG and analyze their co-modulation across frequency bands, spike-phase correlations, spike population dynamics, and other patterns derived from data received from the implant devices 1802, correlating internal and external behaviors. The BCP may further comprise Gateway 1811, which may include computing devices, such as a smartphone, personal computer, tablet computer, etc., and cloud computing services, such as the Fundamental Code Unit (FCU) 1812 cloud computing services, which is a mathematical framework that enables the various BCCS 1810 sensor feeds and implant device 1802 neural impulses to be rapidly and meaningfully combined.

The FCU 1812 may provide common temporal and spatial coordinates for the BCP 1800 and resides in all components of the system (implants, earbuds, app, cloud) ensuring consistent mapping across different data types and devices. FCU 1812 algorithms may provide extremely high rates of data compression, association, and throughput, enabling the implant device 1802 to transcribe neural signals in high volume. Each implant device 1802 may have an embedded AI processor, optical neurostimulation capabilities and electrical recording capabilities. The implant device 1802 may consist of two types of microfabricated carbon nanotube (CNT) neural interfaces, a processor unit for radio transmission and I/O, a light modulation and detection silicon photonic chip, an inductive coil for remote power transfer and an independent receiver system, where the signal processing may reside. The BCP 1800 system may comprise four components: (1) the implant device 1802 implant(s), (2) the BCCS 1810 and (3) the cloud services (with API and SDK) and (4) an inductive power supply.

Figure 19:
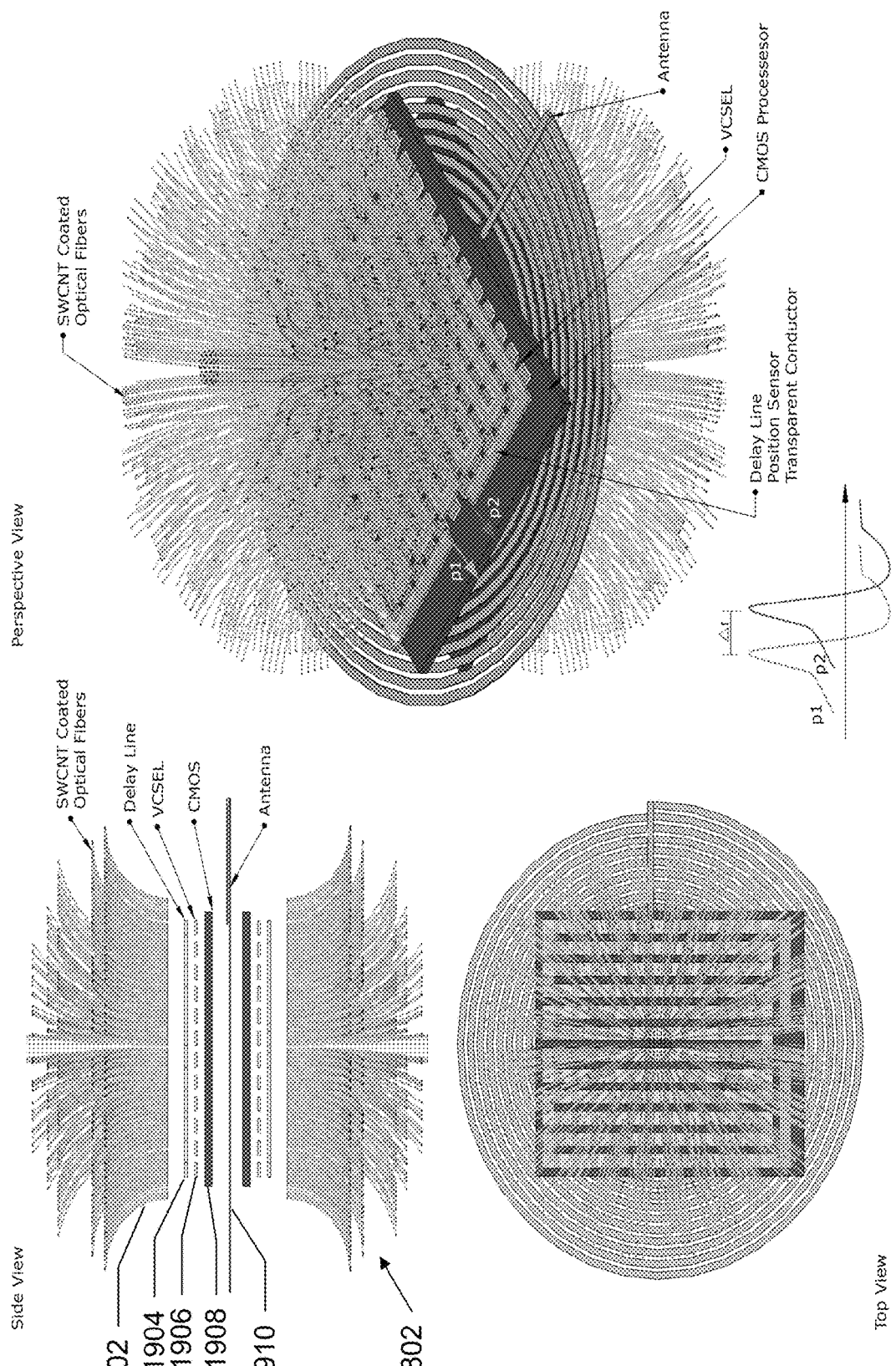
FIG. 19 is an exemplary illustration of an implant device.

The implant device, an example of which is shown in FIG. 19, may be an ultra-low power computing device with interconnects that can attach to nerve and/or brain tissue and read signals/voltages and/or stimulate those tissues with electrical or optical pulses. This multi-physics interaction between the implant device and the tissue may be performed through two back-to-back arrays of optic fibers coated with single wall carbon nanotubes (CNTs). The CNTs may be chosen due to their structure, which has been shown to readily attach to tissue and also due to their remarkable electrical properties. Effectively, the CNTs may serve as electrochemical and optical sensors and measurement/stimulation electrodes. The device may be implanted in the brain or other parts of the body to attach to the nervous system, although this document focuses on attaching to the brain to treat neurological disorders. The implant device may include a communication module to transmit data to a Gateway device such as cell phone or other nearby computer which can in turn analyze data, give input to the implant device, and/or send the data to the Cloud for deep analysis.

The implant device may provide a revolutionary brain-computer interface for research in Neuroscience and medicine, being a closed-loop neural modulator informed by internal and external conditions. The possible therapeutic applications are numerous. For example, the implant device could be used for treatment of chronic pain, spinal cord injury, stroke, sensory deficits, and neurological disorders such as epilepsy, Parkinson's, Alzheimer's, and PTSD, all of which have evidence supporting the efficacy of neurostimulation therapy.

Turning briefly to FIG. 19, each implant device 1802 implant may be, for example, an oblate spheroid (for example, 0.98×0.97×1.0 cm), a design inspired by the radial characteristics of an implant device 1802 fruit. In the center of the implant is a nucleus surrounded by a fleshy membrane. The nucleus may house the processing, transmitting, and receiving circuitry 1908, including an embedded processor for local preprocessing, read and write instructions, the modulation scheme, and an optical FPGA dedicated for real time optical modulation. It may also contain a CMOS dedicated integrated front-end circuit developed for a pre-amplification and multiplexing of the neural signals recorded, 4G-MM for offline storage, wireless transceiver, inductive power receiver, and an optical modulation unit. Covering the nucleus are, for example, 1 million fibers 1902 made of single walled carbon nanotubes (SWCNT) and, for example, 1100 geometrically distributed optical fibers coated with SWCNT, connected in the same manner as the SWCNT fibers, wrapping around a central primary processing nucleus. Fibers may be built on a flexible interface substrate and surrounded by a gel/flesh membrane. When implanted, the membrane casing will slowly dissolve, naturally exposing the probes to a cellular environment with limited risk of rejection. The lubrication of the CNT probes will attract neurons to the implant. The implant device 1802 implant will be able to record from pyramidal layers II-III down to layer VI of any brain cortex region. Also shown in FIG. 19 are delay line devices 1904, light sources, such as vertical-cavity surface-emitting lasers 1906 (VCSELs), and antenna 960.

Figure 20:
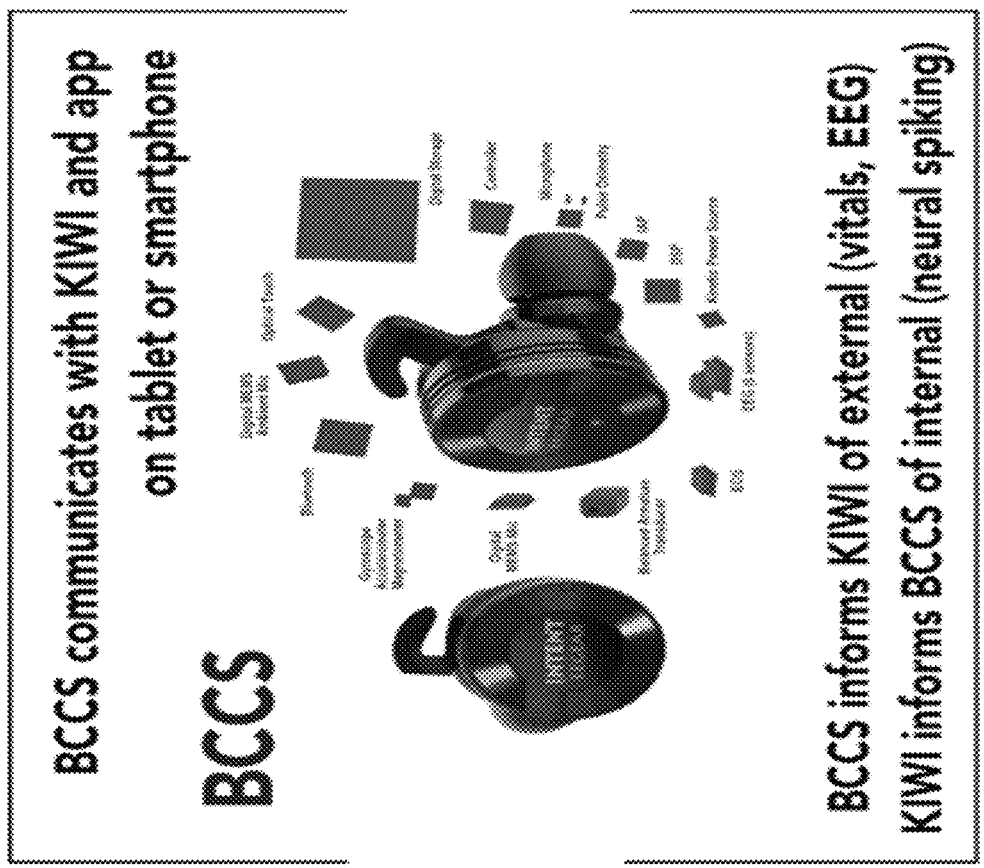
FIG. 20 is an exemplary illustration of a BCCS earbud.

Returning to FIG. 18, the BCCS earbud 1806, also shown in FIG. 20, wirelessly communicates with the implant device 1802. The earbud contains a signal amplifier and a relay for modulation schemes, algorithms, and instructions to and from the implant. The BCCS earbud 1806 also has additional functions, such as EEG and vestibular sensors, which will serve as crosscheck metrics to measure efficacy and provide global behavioral, physiological, and cognitive data along with neural data on the same timescale.

Figure 21:
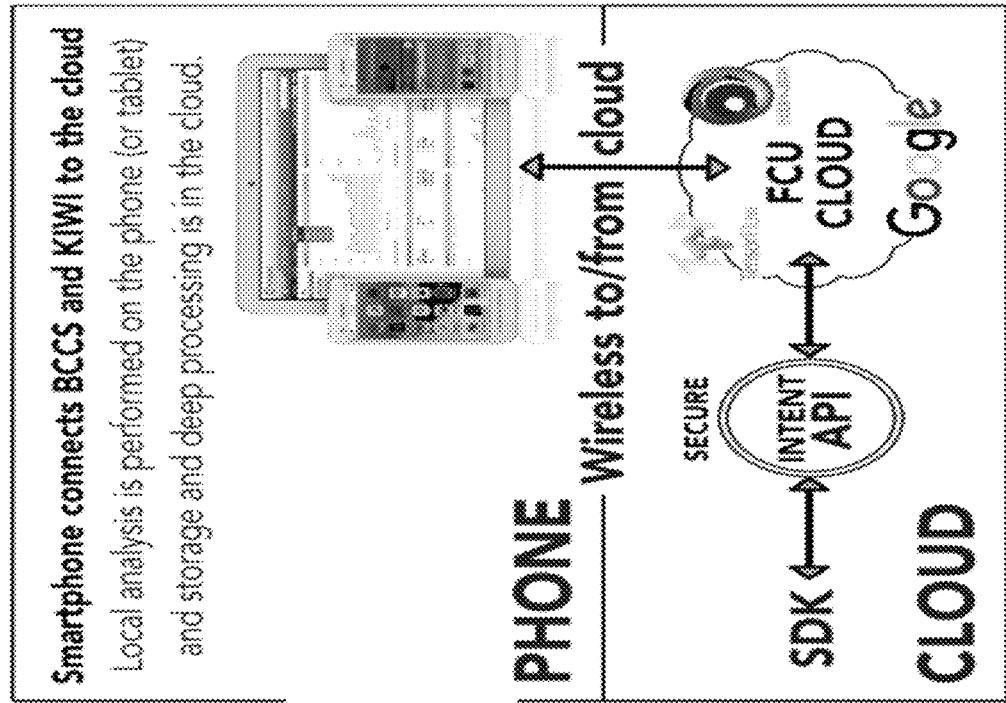
FIG. 21 is an exemplary illustration of a cloud platform.

A cloud platform 1812, also shown in FIG. 21, may include the parallel data flow and FCU 1812 analytic engine powered by neuro-computational algorithms and extreme machine learning. EEG, ECG, and other physiological data (external and internal) will be uploaded to the cloud wirelessly from the BCCS 1810 and implant device 1802. A suite of algorithms will analyze the aggregate datastream and formulate instructions for optimal electrical and/or optical neuromodulations in a closed loop feedback system. Integrated stimulation/control, recording/readout and modulated stimulation parameters will allow simultaneous optical and/or electrical recording and stimulation.

An inductive powering system 1814, also shown in FIG. 22, may be used to recharge the implant device 1802 implant (see FIG. 18). Various wearable and/or kinetic inductive power technologies may be utilized during the design phase, including a retainer/mouthguard, a head-mounted cap to be worn at night, or an under the pillow charging mat.

Combined electro and optogenetic approach enables precise (ON/OFF) control of specific target neurons and circuits. Unary controls in combination with rapid closed loop controls in the implant device's microchip will enable neural synapse firings with intensity, and frequency modulation.

Integrating SWCNT nanotechnology with optical fibers enables both optogenetic writing and electrical neurostimulation capabilities.

CNTs are biologically compatible, enabling the implant device to be stably implanted for long periods of time.

A dissolvable membrane, such as Dextrane, Gelatine, or Collicoat, will limit the risk of damaging sensitive surface tissue during surgery and minimize adverse tissue reactions following the implant insertion trauma. This will protect both the patient and the CNTs.

The implant device will be in the brain parenchyma, rather than tethering the implant to the skull, which can be a major contributor to adverse tissue reactions.

The implant device's open hardware architecture can record data from all pyramidal layers II-III down to layer VI offering several advantages in terms of data quality.

Closed loop architecture enables dynamic, informed response based on live internal and external conditions.

Big data approach utilizing smartphone apps, SDKs, and websites/APIs will provide visual, aggregate, and actionable real-time biofeedback and software modification capabilities.

Big data approach utilizing cloud API will provide storage to capture extremely large volumes of data. The cloud platform also provides the massive processing power required to analyze these huge data sets across subject profiles and a plurality of research databases (PPMI, PDRS, etc.).

Open software architecture SDK will allow the creation of new applications and different protocols for clinical and research use, by partners, researchers and third parties.

The BCCS will be able to synchronously capture EEG, ECG, PulseOx, QT intervals, BP, HR, RR, true body temperature, body posture, movement, skin conductance, vestibular data, and audio data to provide a rich set of multi-modal data streams to dynamically correlate internal states read by the implant device and external states observed by the BCCS, a process which will help to effectively map neural pathways and function.

A passive inductive power unit and the BCCS earbud amplifier will be used external to the cranium, allowing the implant device to be small, low power and of low energy consumption. Any design for an extended-use implant without such an external component would need to be considerably larger (and of a finite lifespan).

The BCP data flow (internal and external) allows machine learning, prior experience, and real time biofeedback to autonomously guide implant device neuromodulation. Eventually the BCP will achieve an advanced level of sensitivity and will be able to autonomously sense neuron activity and guide light and/or electrical stimulation as needed.

Autonomous stimulation will be guided by intuitive algorithms and operational self-monitoring during awake state and sleep. Personal profiles and personalized signatures of neural activity will be learned and coded over time.

The BCP system takes two distinct but complementary approaches: a direct approach by means of recording brain activity and an indirect approach deduced from the multimodal aggregate analysis of peripheral effectors such as temperature, cardiac activity, body posture and motion, sensory testing etc. This simultaneous and coupled analysis of the interplay between the brain "activities and functions" (including physiological, chemical and behavioral activities) and its peripheral effectors and the influence of the effectors on the brain "activities and functions" has never been done before.

Simultaneous brain recording and stimulation of the same region allows us to take account of the initial state of the neurons and their environment, enabling comprehension of the neurons properties and network as well as brain functions (as the data are only valid for the specific conditions in which they were obtained). Methods which are forced to ignore this initial state have limited potential for understanding the full system.

Implant device Development—in an embodiment, an approach to solving density challenges combines traditional photolithographic thin-film techniques with origami design elements to increase density and adaptability of neuronal interfaces. Compared to traditional metal or glass electrodes, polymers such as CNT are flexible, strong, extremely thin, highly biocompatible, highly conductive, and have low contact impedance, which permits bidirectional interfacing with the brain (Vitale et al., 2015). These properties are especially valuable for the construction of high-density electrode arrays designed for chronic and/or long-term use in the brain. Our approach to precision and accuracy supersedes the current state of the art (SOA), which is limited to only being able to fit certain regions of the brain. These limits are due both to the physical design of the interface inserted and also to the limits of tethered communication within deeper cortical areas. The implant device, on the other hand, is wireless and inductively powered, and so is implantable anywhere in the brain with a subdural transceiver, to allow reading of neurons both at the surface and in 3D. CNT fibers will allow for bidirectional input and output. CNTs will also enable more biocompatible, longer-lasting designs—current neural implants work well for short periods of time, but chronic or long-term use of neural electrodes has been difficult to achieve. The main reasons for this are: 1) degradation of the electrode, 2) using oversized electrodes to attain sufficient signal-to-noise ratio during recording, and 3) the body's natural immune response to implantation. Although there is a strong desire among neurologists to record chronic neural activity, electrodes used today can damage brain tissue and lose their electrical contacts over time (McConnell et al., 2009, Prasad et al., 2012). This is of particular concern in the case of deep cortical implants, so alternative materials, design principles, and insertion techniques are needed. CNT is a biocompatible material that has been studied for long-term use in the brain.

Optogenetics may be used to facilitate selective, high-speed neuronal activation; a technology in which light-sensitive ion channels are expressed in target neurons allowing their activity to be controlled by light. By coating optical fibers (~8 μm) with dense, thin (~1 μm) CNT conformal coatings, optical modulation units may be built within the nucleus of the implant device that can deliver light to precise locations deep within the brain while recording electrical activity at the same target locations. The light-activated proteins channelrhodopsin-2 and halorhodopsin may be used to activate and inhibit neurons in response to light of different wavelengths. Precisely-targetable fiber arrays and in vivo-optimized expression systems may enable the use of this tool in awake, behaving primates.

A suite of brain to digital and digital to brain (B2D:D2B) algorithms may be used for transducing neuron output into digital information. These algorithms may be theoretically-grounded computational models corresponding to the theory of similarity computation in Bottom-Up and Top-Down signal interaction. These neurally-derived algorithms may use mathematical abstractions of the representations, transformations, and learning rules employed by the brain, which will correspond to the models derived from the data and correspond to the general dynamic logic and mathematical framework, account for uncertainty in the data, as well as provide predictive analytical capabilities for events yet to take place. The BCP analytics may provide advantages over conventional systems in similarity estimation, generalization from a single exemplar, and recognition of more than one class of stimuli within a complex composition ("scene") given single exemplars from each class. This enables the system to generalize and abstract non-sensory data (EEG, speech, movement). Combined, these provide both global (brain-wide) and fine detail (for example, communication between and within cytoarchitectonic areas) modalities for reading and writing across different timescales.

The implant device may be a microfabricated carbon nanotube neural implant that may provide, for example, reading from ≥1,000,000 neurons, writing to ≥100,000 neurons, and reading and writing simultaneously to ≥1,000 neurons. The BCCS may include multisensory wireless inductive earbuds and behavioral sensors and provide wireless communication with implant device, inductively recharge implant device, provide Bluetooth communication with a secure app on smartphones, tablets, etc., and may provide interfacing with cloud—API, SDK and secure website for clinicians, patients (users)

The implant device and BCCS devices may be used in combination with FCU, BC and IA algorithms to translate audial cortex output, matching internal and external stimulus (for example, output) to transcribe thought into human readable text.

The BCP may provide advantages over conventional systems by providing a closed loop neural interface system that uses big data analytics and extreme machine learning on a secure cloud platform, to read from and intelligently respond to the brain using both electrical and optical modulation. The FCU unary framework enables extremely high-speed compression, encryption, and abstract data representation, allowing the system to process multimodal and multi-device data in real-time. This capability is of great interest and benefit to both cognitive neurosciences and basic comprehension of brain function and dysfunction because: (1) it combines high dynamic spatiotemporal and functional resolution with the ability to show how the brain responds to demands made by change in the environment and adapts over time through its multiple relationships of brain-behavior and brain-effectors; (2) it assesses causality because the data streams are exhibited temporally relative to the initial state and each state thereafter by integrating physiological and behavioral factors such as global synchrony, attention level, fatigues etc. and (3) data collection does not affect, interfere, or disrupt any function during the process.

The BCP may provide advantages over conventional systems by recording from all six layers of the primary A1 cortex and simultaneously from the mPFC, with very high spatial resolution along the axis of the penetrating probe by combining CNT with fiber optic probes that wrap around a central nucleus. By including the principal input layer IV and the intra columnar projection layers, as well as the major output layers V and VI, brain activity can be monitored with unprecedented resolution. The recording array will be combined with optogenetic stimulation fibers, which are considerably larger and stiffer than electrode arrays. CNT fibers will be used as recording electrodes at an unprecedented scale and within a highly dense geometry.

Carbon nanotubes address the most important challenges that currently limit the long-term use of neural electrodes and their unique combination of electrical, mechanical and nanoscale properties make them particularly attractive for use in neural implants. CNTs allow for the use of smaller electrodes by reducing impedance, improving signal-to-noise ratios while improving the biological response to neural electrodes. Measurements show that the output photocurrent varies linearly with the input light intensity and can be modulated by bias-voltage. The quantum efficiency of CNTs are about 0.063% in 760 Torr ambient, and becomes 1.93% in 3 mTorr ambient. A SWCNT fiber bundle can be stably implanted in the brain for long periods of time and attract neurons to grow or self-attaching to the probes. CNT and optical fibers will be an excellent shank to wrap a polymer array around.

Returning to FIG. 19, the optical fibers 1902 will be coated with SWCNTs and make electrical connections with the underlying delay line. The delay line 1904 will be transparent to allow light from the vertical-cavity surface-emitting lasers 1906 (VCSELs) to reach the optical fibers. The delay lines 1904 potentially make the electrical signal position-dependent by comparing the time between pulses measured at the outputs. Provided the pulses are of sufficient intensity and individual pulses are sufficiently separated in time (>1 µs or so), the difference between pulse arrival times could be related to the position on the array. Combining this with spatially controlled optical excitation (i.e., by turning on specific VCSELs 1906) would further help to quantify position, as VCSEL pulses excite a small region at the end of the adjacent fiber. These pulses are measured at a position on the delay line close to this fiber, so if neighboring neurons fire, they are sensed by nearby fibers (i.e., the SWCNTs on the fibers) and would generate additional pulses that could then be tracked over time with the delay line, mapping out the path. The SWCNT coated fiber array 1902 would be randomly connected to the underlying VCSEL array as we will not have control over the fiber locations in the bundle. The substrate connectors will be graphitic nano joints to a single-walled carbon nanotube, we will also utilize the IBM CNT connect technique for other connectors.

Carbon nanotubes are ideal for integration into a neural interface and the technical feasibility of doing so is well documented. The use of CNT allows for one unit to function as recording electrodes and stimulating optical fibers. The optical transceivers will be integrated as a separate die on a silicon substrate, tightly-coupled to logic dice (a.k.a. "2.5D integration"). The choice of materials reflects the positive results of recent studies demonstrating the impact of flexibility and density of implanted probes on CNNI tissue responses. CNTs are not only biocompatible in robust coatings, but they are supportive to neuron growth and adhesion. It has been found that CNTs actually promote neurite growth, neuronal adhesion, and viability of cultured neurons under traditional conditions. The nanoscale dimensions of the CNT allow for molecular interactions with neurons and the nanoscale surface topography is ideal for attracting neurons. In fact, they have been shown to improve network formation between neighboring neurons by the presence of increased spontaneous postsynaptic currents, which is a widely accepted way to judge health of network structure. Additionally, functionalization of CNT can be used to alter neuron behavior significantly. In terms of the brain's immune response, CNT have been shown to decrease the negative impact of the implanted electrodes. Upon injury to neuronal tissue, microglia (the macrophage-like cells of the nervous system) respond to protect the neurons from the foreign body and heal the injury, and astrocytes change morphology and begin to secrete glial fibrillary acidic protein to form the glial scar. This scar encapsulates the electrode and separates it from the neurons. However, carbon nanomaterials have been shown to decrease the number and function of astrocytes in the brain, which in turn decreases the glial scar formation.

Optogenetic tools may be used to enable precise silencing of specific target neurons. Using unary controls in combinations and in rapid closed loop controls within the implant device will enable neural synapse firings with highly precise timing, intensity, and frequency modulation. Optical neuromodulation has many benefits over traditional electrode-based neurostimulation. This strategy will allow precision stimulation in near real time.

The implant device uses a 3D design (and dissoluble membrane), both of which may provide advantages over conventional systems. The dissoluble membrane protects both the patient and the implant during surgery and the lubricant and contraction encourages neural encroachment and adherence to CNTs upon dissolution. This design maximizes neural connectivity and adhesion, while minimizing implant size. implant device size is further reduced through inductive charging.

The BCP system aims at producing a significant leap in neuroscience research not only in scale but also in precision. The method of optical reading and writing at the same time, using SWCNT optrodes, can be combined with current cell marking techniques to guide electrodes and optic fibers to specific regions of the brain. One of the biggest challenges facing neuroscientists is to know for certain if they are hitting the right spot when performing in vivo experiments, whether it is an electrophysiological recording or an optogenetic stimulation. Cell marking techniques, on the other hand, have made a lot of progress during the past 20 years with the use of new viral approaches as well as Cre-Lox recombination techniques to express cell markers in specific sites of the brain. This has allowed, for example, the expression of fluorescent Calcium indicators in target locations without affecting surrounding regions, which is commonly used in in vivo Calcium imaging. Our technique of simultaneous optical reading and writing makes it possible to insert optrodes and guide them through brain tissue until they "sense" optical changes corresponding to the activity of target cells that express a Calcium indicator. This will reduce, to a great extent, the probability of off-target recordings and stimulations.

The synchronous connection between the implant device and BCCS will likely lead to rapid advances in understanding the key circuits and language of the brain. The BCP provides researchers with a more thorough (and contextual)

understanding of neural signaling patterns than ever before, enabling far more responsive brain-machine interfaces (for example, enabling a paralyzed patient to control a computer, quadcopter, or mechanical prosthetic). A wireless implanted device might allow a PD patient to not only quell tremors but actually regain motor capacity, even just minutes after receiving an implant. By combining these technologies with behavioral and physiological metrics, we hope to open up new horizons for the analysis of cognition. Our multimodal diagnostic and analysis allows for an approach of analyzing brain machinery at higher data resolution. The data method could be considered a first step in progressing medicine from snapshots of macro anatomo-physiology to continuous, in-vivo monitoring of micro anatomo-physiology. The in-vivo study of a brain's parcel may give us a real-time relationship of the different components and their functionality, from which the complex functional mechanism of the brain machinery could be highlighted. Giving rise to new medical approaches of diagnosis, treatment, and research. If the animal experiences of two implants prove efficacy and lack of any harm to animal or humans, the BCP may allow us to define a powerful new technique for brain-functional mapping which could be used to systematically analyze and understand the interconnectivity of each brain region, along with the functionality of each region.

Therapeutic aims may include use of the device as a brain stimulator, and indirect by data from recordings highlighting the mechanism(s) by which several diseases occur, owing to implant device's ability to record a basic global neuronal state of a brain region and the dynamic neuronal interplay. The modifications which occur during its normal activity enable us to understand the neuronal properties and the function of a given brain region. Our device is able to give us the dynamic continuum of the whole activity of the considered region and thus provide important insights into the fundamental mechanisms underlying both normal brain function and abnormal brain functions (for example, brain disease). The potential for these findings to be translated into therapies are endless because this device may be used in any region of the brain and represents the first synthesis of a closed-loop neural modulator informed by internal and external conditions. The BCP provides a large amount of information and could be used to explore any brain disease within a real dynamic, in vivo condition. If successful, the potential of this device for the diagnosis of organic brain diseases is enormous and it could be an important complement to MRI for the diagnosis of non-organic disease. The possible therapeutic use of this device may also include chronic pain, tinnitus, and epilepsy. The device could be used in focal epileptic zone owing to its optogenetic capacity to control excitability of a specific populations of neurons. Even if the device does not cure epilepsy, it may help to control otherwise refractory seizures and help to avoid surgery. Nonetheless optimizing the place of this device in therapy for epilepsy will require further study and clinical experience.

Recent demonstrations of direct, real-time interfaces between living brain tissue and artificial devices, such as with computer cursors, robots, and mechanical prostheses, have opened new avenues for experimental and clinical investigation of Brain Machine Interfaces (BMIs). BMIs have rapidly become incorporated into the development of 'neuroprosthetics,' which are devices that use neurophysiological signals from undamaged components of the central or peripheral nervous system to allow patients to regain motor capabilities. Indeed, several findings already point to a bright future for neuroprosthetics in many domains of rehabilitation medicine. For example, scalp electroencephalography (EEG) signals linked to a computer have provided 'locked-in' patients with a channel of communication. BMI technology, based on multi-electrode single-unit recordings, a technique originally introduced in rodents and later demonstrated in non-human primates, has yet to be transferred to clinical neuroprosthetics. Human trials in which paralyzed patients were chronically implanted with cone electrodes or intracortical multi-electrode arrays allowed the direct control of computer cursors. However, these trials also raised a number of issues that need to be addressed before the true clinical worth of invasive BMIs can be realized. These include the reliability, safety and biocompatibility of chronic brain implants and the longevity of chronic recordings, areas that require greater attention if BMIs are to be safely moved into the clinical arena. In addition to offering hope for a potential future therapy for the rehabilitation of severely paralyzed patients, BMIs can be extremely useful platforms to test various ideas for how populations of neurons encode information in behaving animals. Together with other methods, research on BMIs has contributed to the growing consensus that distributed neural ensembles, rather than the single neuron, constitute the true functional unit of the CNS responsible for the production of a wide behavioral repertoire (reference).

When designing an interface between a living tissue and an electronic device, there are important factors to consider. Particularly, the structural and chemical differences between these two systems; the electrode ability to transfer charge; and the temporal-spatial resolution of recording and stimulation. Traditional multi-electrode array (MEAs) for neuronal applications present several limitations: low signal to noise ratio (SNR), low spatial resolution (leading to poor site specificity) and limited biocompatibility (easily encapsulated with non-conductive undesirable glial scar tissue) which increases tissue injury and immune response. Neural electrodes should also accommodate for differences in mechanical properties, bioactivity, and mechanisms of charge transport, to ensure both the viability of the cells and the effectiveness of the electrical interface. An ideal material to meet these requirements is carbon nanotubes (CNTs). CNTs are well suited for neural electrical interfacing applications owing to their large surface area, superior electrical and mechanical properties, and the ability to support excellent neuronal cell adhesion. Over the past several years it has been demonstrated as a promising material for neural interfacing applications. It was shown that the CNTs coating enhanced both recording and electrical stimulation of neurons in culture, rats, and monkeys by decreasing the electrode impedance and increasing charge transfer. Related work demonstrated the single-walled CNTs composite can serve as material foundation of neural electrodes with chemical structure better adapted with long-term integration with the neural tissue, which was tested on rabbit retinas, crayfish in vitro and rat cortex in vivo.

Using long CNTs implanted into the brain has many advantages, for instance an optical fiber with CNTs protruding from it, but this technology has not been trialed in vivo or expanded to very large numbers of recording channels. Characterization in vitro showed that the tissue contact impedance of CNT fibers was lower than that of state-of-the-art metal electrodes, chronic studies in vivo in parkinsonian rodents also showed that CNT fiber microelectrodes stimulated neurons as effectively as metal electrodes. Stimulation of hippocampal neurons in vitro with vertically multiwalled CNTs electrodes suggested CNTs were capable of providing far safer and efficacious solutions for neural prostheses than metal electrode approaches. CNT-MEA chips proved useful for in vitro studies of stem cell differentiation, drug screening and toxicity, synaptic plasticity, and pathogenic processes involved in epilepsy, stroke, and neurodegenerative diseases. Nanotubes are a great feature for reducing adverse tissue reactions and maximizing the chances of high-quality recordings, but squeezing a lot of hardware into a small volume of tissue will likely produce severe astroglial reactions and neuronal death. At the same time, CNTs could extend the recording capabilities of the implant beyond the astroglial scar, without increasing the foreign body response and the magnitude of tissue reactions. Implantation of traditional, rigid silicon electrode arrays has been shown to produce a progressive breakdown of the blood-brain barrier and recruitment of an astroglial scar with an associated microglia response.

Neural implant geometry and design is highly dependent on animal model used, where larger animals will see a somewhat less dramatic deterioration in recording quality and quantity, so early trials in rats probably shouldn't be too focused on obtaining very long-term recordings on a very large number of channels. While loss of yield due to abiotic failures is a manufacturing process and handling problem, biotic failures driven hostile tissue reactions can only be addressed by implementing design concepts shown to reduce reactive astrogliosis, microglial recruitment and neuronal death (Prasad, A. et al., 2012; McGonnell, G C. et al., 2009).

Conventional thin film probes can fit hundreds of leads into one penetrating shank. Rolling up a planar design would come with several benefits: first, it would decrease the amount of tissue damage a wide 2D-structure would produce. This is essential for the very high densities we are aiming for. Second, it would stiffen the probe, making it easier to penetrate tissue. Thirdly, a round cross section is preferable for reducing the foreign body response in the brain parenchyma. Finally, this design allows for potentially extremely dense architectures, as by combining several of these probes into a 10×10 array of 1 $cm^2$, an implant using this technology could potentially deploy several tens of thousands of leads in a multielectrode array, and could be conceivably combined with optical fibers for stimulation within an electronic-photonic microarray implant. A design of an implantable electrode system may be a 3D electrode array attached to a platform on the cortical surface. Said platform would be used for signal processing and wireless communication.

Why coatings or composites with CNT? The unique combination of electrical, mechanical and nanoscale properties of carbon nanotubes (CNT) make them very attractive for use in NE. Recent CNT studies have tried different CNT coatings or composites on metal electrodes and growing full electrodes purely from CNT. Edward W. Keefer et al., (2008) was the first to do a recording study using different coatings made with CNT on electrodes. They found that CNT can help improve the electrode performance during recording by decreasing impedance, increasing charge transfer, and increasing signal-to-noise ratio. CNT may improve the biological response to neural electrodes by minimizing risk of brain tissue rejection.

Why ICA for analysis? ICA signal separation is performed on a sample by sample basis where no information about spike shape is used. For this reason, it is possible to achieve good performance of sorting accuracy in terms of misses and false positives, especially in cases where the background noise is not stationary but fluctuate throughout trials, which is the fact based on biophysical and anatomical considerations but is ignored by most current spike sorting algorithms One assumption underlying this technique is that the unknown sources are independent, which is the case under the assumption that the extracellular space is electrically homogeneous, pairs of cells are less likely to be equidistant from both electrodes. The other assumption of this approach is that the number of channels must equal or greater than the number of sources, which can yield advantages for large-scaled recordings.

Exemplary tables of advantages of aspects of technologies that may be utilized by embodiments are shown in FIGS. 23 and 24.

The two-implant devices may be implanted within the mPFC in addition to the A1 primary auditory cortex because this cortical area may be implicated in the pathogenesis of PTSD. Dopaminergic modulation of high-level cognition in Parkinson's disease and the role of the prefrontal cortex may be revealed by PET, as may widely distributed corticostriatal projections. The mPFC may also be implicated in psychiatric aspects of other disorders, for example deficits in executive functions, anxiety, and depression. By recording from the selected sensory areas and implanting two kiwis at same time, the chance of needing further surgical corrections may be reduced, and data recording may be increased. Knowledge may be extracted that may lead to corrections of associated cognitive deficit in conditions like PTSD but in general to cognitive decline as it occurs for many unknown indicators.

Figure 25:
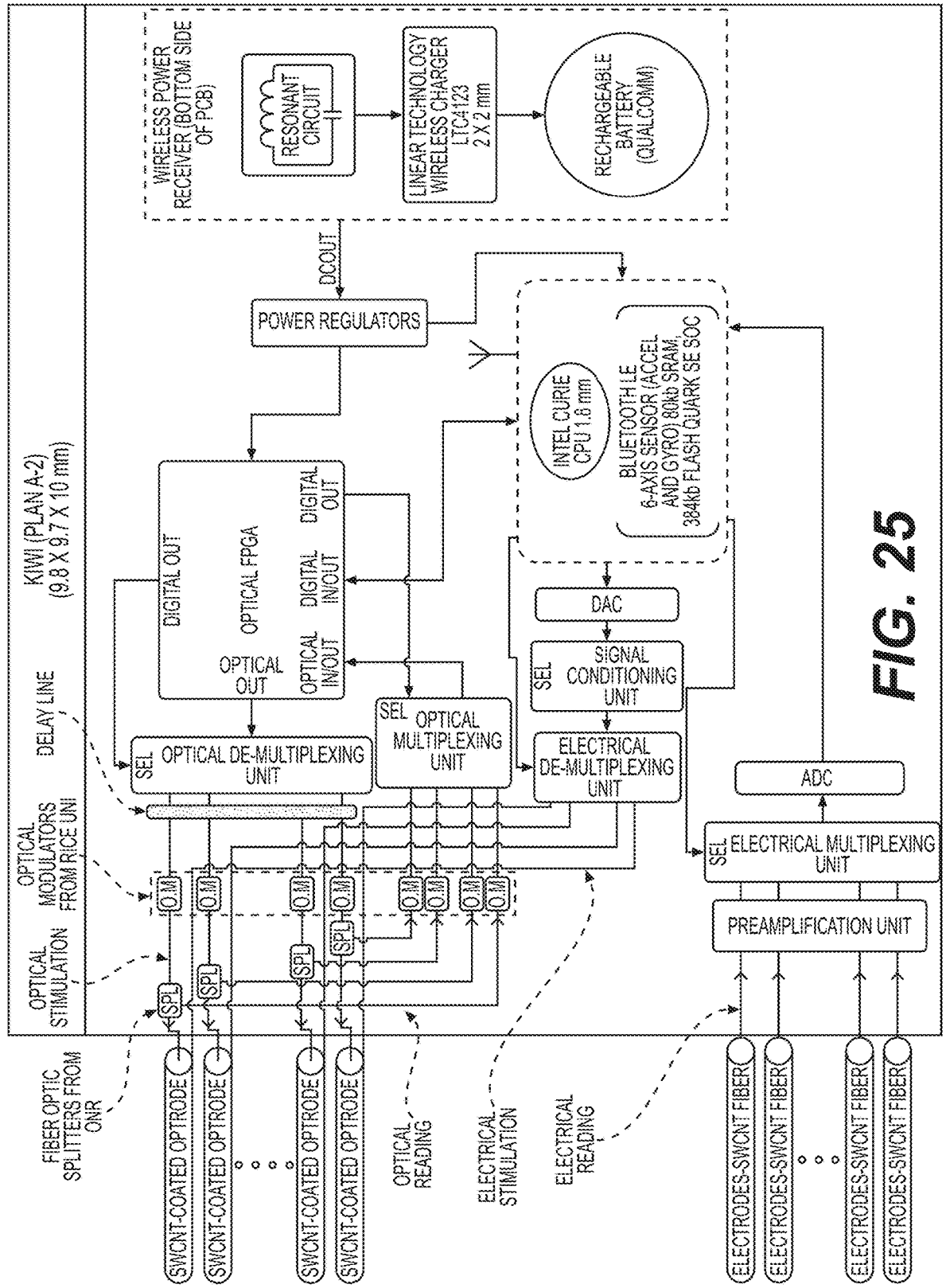
FIG. 25 is an exemplary block diagram of embodiments of an implant device.
Figure 26:
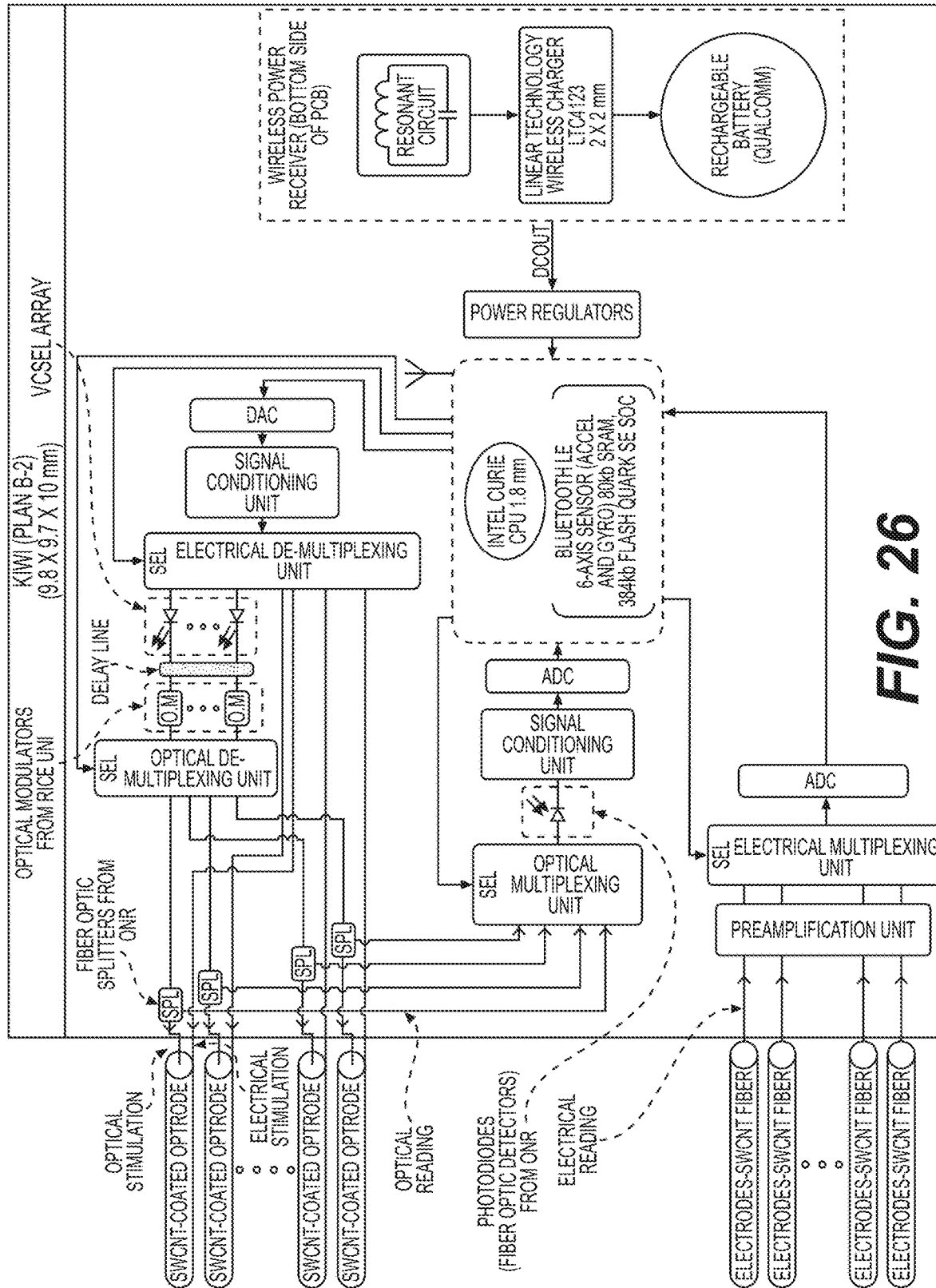
FIG. 26 is an exemplary block diagram of embodiments of an implant device.

In an embodiment, the BCP hardware may be fabricated using electronic components available on the market today. In an embodiment, the implant device may be made with a microfabricated carbon nanotube (CNT) neural interface, a light modulation and detection silicon photonic chip, and an independent Central Processing Unit (CPU) where all the processing will preside. RF communication between the implant device and BCCS may carried out either by making use of the processor's Bluetooth capability or by implementing an independent RF transceiver in each of the two devices. The BCCS device may be calibrated to and securely integrated with the implant device. Exemplary block diagrams of embodiments of an implant device 2500 is shown in FIGS. 25 and 26.

Figure 28:
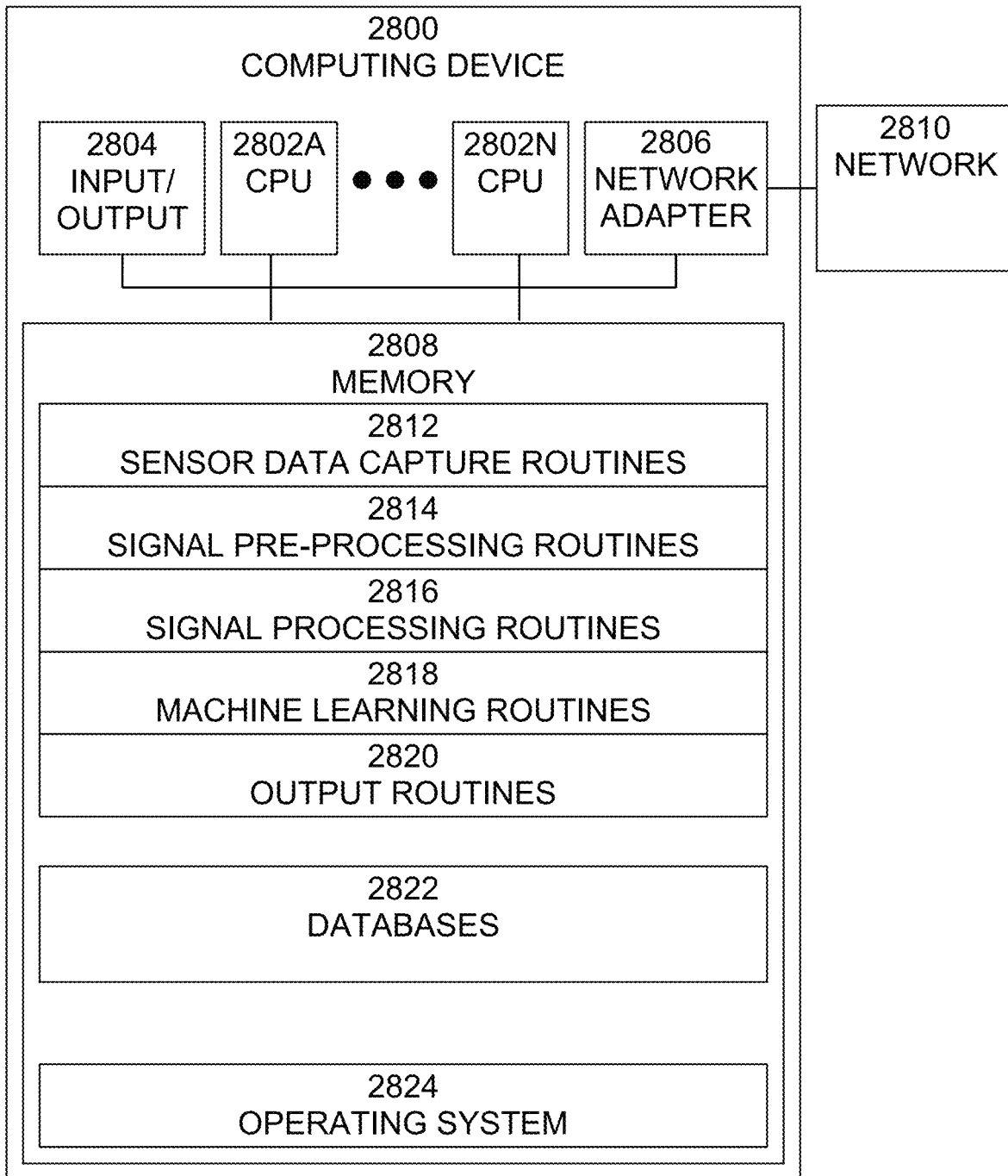
FIG. 28 is an exemplary block diagram of a computing device.

An exemplary block diagram of a computing device 2800, in which processes involved in the embodiments described herein may be implemented, is shown in FIG. 28. Computing device 2800 may be a programmed general-purpose computer system, such as an embedded processor, microcontroller, system on a chip, microprocessor, smartphone, tablet, or other mobile computing device, personal computer, workstation, server system, and minicomputer or mainframe computer. Computing device 2800 may include one or more processors (CPUs) 2802A-2802N, input/output circuitry 2804, network adapter 2806, and memory 2808. CPUs 2802A-2802N execute program instructions in order to carry out the functions of the present invention. Typically, CPUs 2802A-2802N are one or more microprocessors, such as an INTEL PENTIUM® processor. FIG. 28 illustrates an embodiment in which computing device 2800 is implemented as a single multi-processor computer system, in which multiple processors 2802A-2802N share system resources, such as memory 2808, input/output circuitry 2804, and network adapter 2806. However, the present invention also contemplates embodiments in which computing device 2800 is implemented as a plurality of networked computer systems, which may be single-processor computer systems, multi-processor computer systems, or a mix thereof.

Input/output circuitry 2804 provides the capability to input data to, or output data from, computing device 2800. For example, input/output circuitry may include input devices, such as keyboards, mice, touchpads, trackballs, scanners, etc., output devices, such as video adapters, monitors, printers, etc., and input/output devices, such as, modems, etc. Network adapter 2806 interfaces device 2800 with a network 2810. Network 2810 may be any public or proprietary LAN or WAN, including, but not limited to the Internet.

Memory 2808 stores program instructions that are executed by, and data that are used and processed by, CPU 2802 to perform the functions of computing device 2800. Memory 2808 may include, for example, electronic memory devices, such as random-access memory (RAM), read-only memory (ROM), programmable read-only memory (PROM), electrically erasable programmable read-only memory (EEPROM), flash memory, etc., and electro-mechanical memory, such as magnetic disk drives, tape drives, optical disk drives, etc., which may use an integrated drive electronics (IDE) interface, or a variation or enhancement thereof, such as enhanced IDE (EIDE) or ultra-direct memory access (UDMA), or a small computer system interface (SCSI) based interface, or a variation or enhancement thereof, such as fast-SCSI, wide-SCSI, fast and wide-SCSI, etc., or Serial Advanced Technology Attachment (SATA), or a variation or enhancement thereof, or a fiber channel-arbitrated loop (FC-AL) interface.

The contents of memory 2808 may vary depending upon the function that computing device 2800 is programmed to perform. For example, as shown in FIG. 1, computing devices may perform a variety of roles in the system, method, and computer program product described herein. For example, computing devices may perform one or more roles as end devices, gateways/base stations, application provider servers, and network servers. In the example shown in FIG. 28, exemplary memory contents are shown representing routines and data for all of these roles. However, one of skill in the art would recognize that these routines, along with the memory contents related to those routines, may not typically be included on one system or device, but rather are typically distributed among a plurality of systems or devices, based on well-known engineering considerations. The present invention contemplates any and all such arrangements.

In the example shown in FIG. 28, memory 2808 may include sensor data capture routines 2812, signal pre-processing routines 2814, signal processing routines 2816, machine learning routines 2818, output routines 2820, databases 2822, and operating system 2824. For example, sensor data capture routines 2812 may include routines that interact with one or more sensors, such as EEG sensors, and acquire data from the sensors for processing. Signal pre-processing routines 2814 may include routines to pre-process the received signal data, such as by performing band-pass filtering, artifact removal, finding common spatial patterns, segmentation, etc. Signal processing routines 2816 may include routines to process the pre-processed signal data, such as by performing time domain processing, such as spindle threshold processing, frequency domain processing, such as power spectrum processing, and time-frequency domain processing, such as wavelet analysis, etc. Machine learning routines 2818 may include routines to perform machine learning processing on the processed signal data. Output routines 2820 may include software routines to generate stimulus commands to provide stimulus waveforms so as to perform Fundamental Code Unit Unary signaling as described above. Databases 2822 may include databases that may be used by the processing routines. Operating system 2824 provides overall system functionality.

As shown in FIG. 28, the present invention contemplates implementation on a system or systems that provide multi-processor, multi-tasking, multi-process, and/or multi-thread computing, as well as implementation on systems that provide only single processor, single thread computing. Multi-processor computing involves performing computing using more than one processor. Multi-tasking computing involves performing computing using more than one operating system task. A task is an operating system concept that refers to the combination of a program being executed and bookkeeping information used by the operating system. Whenever a program is executed, the operating system creates a new task for it. The task is like an envelope for the program in that it identifies the program with a task number and attaches other bookkeeping information to it. Many operating systems, including Linux, UNIX®, OS/2®, and Windows®, are capable of running many tasks at the same time and are called multitasking operating systems. Multi-tasking is the ability of an operating system to execute more than one executable at the same time. Each executable is running in its own address space, meaning that the executables have no way to share any of their memory. This has advantages, because it is impossible for any program to damage the execution of any of the other programs running on the system. However, the programs have no way to exchange any information except through the operating system (or by reading files stored on the file system). Multi-process computing is similar to multi-tasking computing, as the terms task and process are often used interchangeably, although some operating systems make a distinction between the two.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device.

The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry (such as that shown at 208 of FIG. 2) may include, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

Although specific embodiments of the present invention have been described, it will be understood by those of skill in the art that there are other embodiments that are equivalent to the described embodiments. Accordingly, it is to be understood that the invention is not to be limited by the specific illustrated embodiments, but only by the scope of the appended claims. Further, it is to be noted that, as used in the claims, the term coupled may refer to electrical or optical connection and may include both direct connection between two or more devices and indirect connection of two or more devices through one or more intermediate devices.

What is claimed is:

1. A computer-implemented method for affecting living neural tissue comprising:
    receiving at least one signal from at least one read modality, the signal representing release of photons from the living neural tissue, the read modality comprising at least one read modality neural interface implanted in the living neural tissue;
    computing at least one signal to effect alterations to the living neural tissue based on the received input signal, the computed signal adapted to cause transmission of photons to the living neural tissue; and
    delivering the photons to the living neural tissue to effect alterations to the living tissue using at least one write modality neural interface implanted in the living neural tissue;
    wherein the at least one read modality neural interface and the at least one write modality neural interface comprise at least one optic fiber coated with single wall carbon nanotubes.

2. The method of claim 1, wherein the at least one read modality neural interface and the at least one write modality neural interface comprise the same read/write apparatus.

3. The method of claim 2, wherein the released photons and the delivered photons comprise at least one of near ultraviolet photons, blue photons, or green photons.

4. The method of claim 3, wherein the near ultraviolet photons are a free radical reaction byproduct from mitochondria of the living neural tissue, the blue photons are emitted by NAD(P)H upon absorption of near-UV photons, and the green photons are generated by NAD(P)H oxidases, upon absorption of a (NAD(P)H-generated) blue photon.

5. The method of claim 4, wherein the near ultraviolet photons have a wavelength of about 380 nm, the blue photons have a wavelength of about 470 nm, and the green photons have a wavelength of about 530 nm.

6. The system of claim 5, wherein the delivered photons cause formation of at least one memory pattern in the neural tissue and wherein the computed signal is computed so as to cause the delivered photons to cause formation of at least one memory pattern in the neural tissue.

7. A system for affecting living neural tissue comprising:
 at least one photonic read modality adapted to receive photons from living neural tissue and generating a signal representing the released photons, wherein the at least one photonic read modality comprises at least one read modality neural interface adapted to be implanted in the living neural tissue;
 at least one photonic write modality adapted to deliver photons to the living neural tissue to effect alterations to the living tissue based on at least one computed signal, wherein the at least one photonic write modality comprises at least one write modality neural interface adapted to be implanted in the living neural tissue;
 wherein the at least one photonic read modality and the at least one photonic write modality comprise at least one optic fiber coated with single wall carbon nanotubes; and
 computing circuitry comprising a processor, memory accessible by the processor, and computer program instructions stored in the memory and executable by the processor to compute the at least one signal.

8. The system of claim 7, wherein the at least one read modality neural interface and the at least one write modality neural interface comprise the same read/write apparatus.

9. The system of claim 8, wherein the released photons and the delivered photons comprise at least one of near ultraviolet photons, blue photons, or green photons.

10. The system of claim 9, wherein the near ultraviolet photons are a free radical reaction byproduct from mitochondria of the living neural tissue, the blue photons are emitted by NAD(P)H upon absorption of near-UV photons, and the green photons are generated by NAD(P)H oxidases, upon absorption of a (NAD(P)H-generated) blue photon.

11. The system of claim 10, wherein the near ultraviolet photons have a wavelength of about 380 nm, the blue photons have a wavelength of about 470 nm, and the green photons have a wavelength of about 530 nm.

12. The system of claim 11, wherein the delivered photons cause formation of at least one memory pattern in the neural tissue and wherein the computed signal is computed so as to cause the delivered photons to cause formation of at least one memory pattern in the neural tissue.

13. A non-transitory computer program product for affecting living neural tissue, the non-transitory computer program product comprising a non-transitory computer readable storage having program instructions embodied therewith, the program instructions executable by a computer, to cause the computer to perform a method comprising:
 receiving at least one signal from at least one read modality, the signal representing release of photons from the living neural tissue, the read modality comprising at least one read modality neural interface implanted in the living neural tissue;
 computing at least one signal to effect alterations to the living neural tissue based on the received input signal, the computed signal adapted to cause transmission of photons to the living neural tissue; and
 delivering the photons to the living neural tissue to effect alterations to the living tissue using at least one write modality neural interface implanted in the living neural tissue;
 wherein the at least one read modality and the at least one write modality comprise at least one optic fiber coated with single wall carbon nanotubes.

14. The computer program product of claim 13, wherein the at least one read modality neural interface and the at least one write modality neural interface comprise the same read/write apparatus.

15. The computer program product of claim 14, wherein the released photons and the delivered photons comprise at least one of near ultraviolet photons, blue photons, or green photons.

16. The computer program product of claim 15, wherein the near ultraviolet photons are a free radical reaction byproduct from mitochondria of the living neural tissue, the blue photons are emitted by NAD(P)H upon absorption of near-UV photons, and the green photons are generated by NAD(P)H oxidases, upon absorption of a (NAD(P)H-generated) blue photon.

17. The computer program product of claim 16, wherein the near ultraviolet photons have a wavelength of about 380 nm, the blue photons have a wavelength of about 470 nm, and the green photons have a wavelength of about 530 nm.

18. The computer program product of claim 17, wherein the delivered photons cause formation of at least one memory pattern in the neural tissue and wherein the computed signal is computed so as to cause the delivered photons to cause formation of at least one memory pattern in the neural tissue.

* * * * *